US007129229B2

(12) United States Patent
Raddatz et al.

(10) Patent No.: US 7,129,229 B2
(45) Date of Patent: Oct. 31, 2006

(54) HYDRAZIDE BUILDING BLOCKS AND HYDRAZIDE MODIFIED BIOMOLECULES

(75) Inventors: Stefan Raddatz, Wiesbaden (DE); Jochen Müller-Ibeler, Diez (DE); Markus Schweitzer, Frankfurt am Main (DE); Christoph Brücher, Eschborn (DE); Norbert Windhab, Hofheim (DE); John R. Havens, Arlington, MA (US); Thomas J. Onofrey, Poway, CA (US); Charles H. Greef, Boulder, CO (US); Daguang Wang, Vista, CA (US)

(73) Assignee: Nanogen Recognomics GmbH, Frankfurt am Main (DE)

( * ) Notice: Subject to any disclaimer, the term of this patent is extended or adjusted under 35 U.S.C. 154(b) by 426 days.

(21) Appl. No.: 10/344,092

(22) PCT Filed: Aug. 10, 2001

(86) PCT No.: PCT/US01/41663

§ 371 (c)(1),
(2), (4) Date: Aug. 15, 2003

(87) PCT Pub. No.: WO02/14558

PCT Pub. Date: Feb. 21, 2002

(65) Prior Publication Data

US 2004/0087807 A1    May 6, 2004

(30) Foreign Application Priority Data

Aug. 11, 2000  (US) .................................. 00/22205

(51) Int. Cl.
*A61K 31/66* (2006.01)
*C07F 9/02* (2006.01)

(52) U.S. Cl. ..................... 514/114; 558/70; 558/166; 558/162; 558/185

(58) Field of Classification Search .................. 558/70, 558/166, 162, 185, 183, 181, 180, 116, 117; 514/114, 115
See application file for complete search history.

(56) References Cited

U.S. PATENT DOCUMENTS

| | | | |
|---|---|---|---|
| 5,476,665 A | 12/1995 | Dennison | 424/484 |
| 5,543,054 A | 8/1996 | Charkoudian et al. | 210/638 |
| 5,605,662 A | 2/1997 | Heller et al. | 422/68.1 |
| 5,807,522 A | 9/1998 | Brown et al. | 422/50 |
| 5,830,655 A | 11/1998 | Montforte | |
| 5,837,859 A | 11/1998 | Teoule et al. | 536/25.3 |
| 5,869,466 A | 2/1999 | Westwood et al. | |
| 5,929,208 A | 7/1999 | Heller et al. | 530/333 |
| 5,986,076 A | 11/1999 | Rothschild et al. | 536/22.1 |
| 6,011,020 A | 1/2000 | Gold et al. | 514/44 |
| 7,034,015 B1 * | 4/2006 | Ottosen et al. | 514/114 |

FOREIGN PATENT DOCUMENTS

| | | |
|---|---|---|
| EP | 0361768 | 4/1990 |
| EP | 0816368 | 1/1998 |
| WO | WO 85/05638 | 12/1985 |
| WO | WO 90/03401 | 4/1990 |
| WO | WO 00/29373 | 5/2000 |
| WO | WO 01/07657 | 2/2001 |
| WO | WO 01/09385 | 2/2001 |
| WO | WO 01/51689 | 7/2001 |

OTHER PUBLICATIONS

Beier, M., et al. "Versatile derivatisation of solid support media for covalent bonding on DNA-microchips." Nucleic Acids Research 27(9): 1970-77 (1999).
Raddatz, S., et al. "Hydrazide Oligonucleotides: new chemical modification for chip array attachment and conjugation." Nucleic Acids Research 30(21): 4793-4802 (2002).
Ghosh, S.S., et al., "Synthesis of 5' Oligonucleotide Hydrazide Derivatives and Their Use In Preparation of Enzyme-Nucleic Acid Hybridization Probes," Analytical Biochemistry, vol. 178, No. 1, 1989, pp. 43-51.
Anderson & Kaplan, "Enzymatic Studies With Analogues of Diphosphopyridine Nucleotide," Journal of Biological Chemistry, vol. 234, No. 5, 1959, pp. 1226-1232.
Vogel, K.W., et al., "A Reversed Thioester Analogue of Acetyl-Coenzyme A: An Inhibitor of Thiolase and a Synthon for Other Acyl-CoA Analogues," Journal of the American Chemical Society, Apr. 15, 1998, United States, vol. 120, No. 14, pp. 3275-3283.
Guzaev, A., et al., "Solid Support Synthesis of Ester Linked Hydrophobic Conjugates of Oligonucleotides," Tetrahedron, Elsevier Science Publishers, Amsterdam, NL, vol. 55, No. 30, Jul. 23, 1999, pp. 9101-9116.
Fehlhaber, H-W, et al., "Moenomycin A A Structural Revision and New Structure-Activity Relations," Tetrahedran, vol. 46, No. 5, 1990, pp. 1557-1568.
Raddatz Stefan et al., "Hydrazide Oligonucleotides: New Chemical Modification for Chip Array Attachment and Conjugation," Nucleic Acids Research, vol. 30, No. 21, Nov. 1, 2002, pp. 4793-4802.
Timofeev, et al., "Regioselective Immobilization of Short Oligonucleotides to Acrylic Copolymer Gels," Nucleic Acid Research, vol. 24, No. 16, 1996, pp. 3142-3148.
PCT Search Report for PCT/US00/22205, dated Oct. 26, 2000.
PCT Search Report for PCT/US01/41663, dated Mar. 19, 2002.
European Supplementary Search Report for EP 00955498.1, dated Jan. 18, 2005.
European Examination Report for EP 00955498.1, dated May 5, 2005.

* cited by examiner

*Primary Examiner*—Sabiha N. Qazi
(74) *Attorney, Agent, or Firm*—O'Melveny & Myers LLP

(57) ABSTRACT

This invention relates to attachment chemistries for binding macromolecules to a substrate surface or to other conjugation targets. More particularly, this invention relates to attachment chemistries involving branched or linear structures having one or more hydrazide attachment moieties for binding the macromolecules to a substrate surface, or for other conjugation reactions. Novel modifying reagents are provided for the introduction of protected hydrazide attachment moieties or precursor forms of such hydrazides to the macromolecule, either as a single hydrazide or as multiple hydrazides.

13 Claims, 42 Drawing Sheets

Scheme 1

Scheme 2

Scheme 3

HYDRAZIDE BUILDING BLOCKS AND HYDRAZIDE MODIFIED BIOMOLECULES

This is a national stage application of international application PCT/US01/41663, filed Aug. 10, 2001, which in turn claims priority to international application PCT/US00/22205, filed Aug. 11, 2000, which in turn claims priority to U.S. provisional application Ser. No. 60/175,550, filed on Jan. 11, 2000. All of the above applications are expressly incorporated herein by reference.

FIELD OF THE INVENTION

This invention relates to attachment chemistries for binding macromolecules to a substrate surface or to other conjugation targets. More particularly, this invention relates to attachment chemistries involving branched or linear structures having one or more hydrazide attachment moieties for binding the macromolecules to a substrate surface, or for other conjugation reactions. Novel modifying reagents are provided for the introduction of protected hydrazide attachment moieties or precursor forms of such hydrazides to the macromolecule, either as a single hydrazide or as multiple hydrazides.

BACKGROUND OF THE INVENTION

The following description provides a summary of information relevant to the present invention. It is not an admission that any of the information provided herein is prior art to the presently claimed invention, nor that any of the publications specifically or implicitly referenced are prior art to the invention.

The immobilization of oligonucleotides on substrates is an important and necessary step for many applications such as DNA chip technology, surface plasmon resonance experiments, or other bio-sensor applications. Classically, oligonucleotides are immobilized onto substrates by modification of the 3'- or 5'-end with one reactive group. Oligonucleotides have been modified with a terminal amine, thiol or aldehyde (for covalent attachment) or a group capable of forming stable complexes e.g. biotin, phenylboronic acid etc. (for noncovalent attachment). The modified oligonucleotides are then placed at the location where the immobilization is desired and reacted with an appropriate functional group on the substrate, such as an aldehyde, maleimide, etc., or complexed with a binding molecule such as streptavidin, etc. Placing at specific locations on a substrate can be done by mechanical spotting or spraying (pin or drop deposition), by electronic addressing, or by a variety of other processes. In some cases the reaction for the immobilization is slow and requires long (overnight) incubation of the oligonucleotides on the substrate. These immobilization reactions may also be reversible, resulting in the release of the macromolecule over time.

In other contexts, dendrimeric structures on macromolecules has been described (e.g., WO 99/10362, WO 96/19240, and WO 99/43287). However, these uses of dendrimeric structures have focused on providing signal sites, such as for detection, while the macromolecule itself is simply attached to any substrate present by using classical means.

SUMMARY OF THE INVENTION

In contrast thereto, the present invention describes an improved process for immobilization of macromolecules, particularly oligos containing multiple reactive sites, i.e. nucleophiles, electrophiles, and Lewis acids or bases. The advantage of this approach is a higher rate of immobilization, a higher stability of the attachment, and the potential to obtain higher amounts of immobilized oligo onto the substrate surface in less time. These gains are independent of the approach used for the immobilization. Oligos with multiple attachment moieties can be obtained with both covalent and noncovalent attachment chemistries. However, as described below, hydrazide attachment chemistries for covalent attachment of oligos or macromolecules to surfaces (such as permeation layers or other assay immobilization formats) are preferred for use in the methods and compositions of the invention.

Furthermore the present invention describes the preparation of oligos containing one or more hydrazides, which can be utilized for conjugation to surface binding moieties, or for solution conjugations with other macromolecules, labeling moieties, etc. Hydrazides are nucleophilic reactive groups that can be used for a wide variety of conjugation reactions, as show in FIG. 18. They can react, for example, with electrophilic aldehydes forming hydrazones (which can be further stabilized by reduction) and with active esters forming stable covalent linkages, see FIG. 18. This chemistry can be used for attaching fluorophores, proteins or peptides, reporter groups and other oligomers to oligos. The reactions of hydrazides can also advantageously be used for the immobilization of macromolecules onto substrates, as demonstrated in the examples. The immobilization of oligos by hydrazides shows a marked increase immobilized molecules per mole reagent, as compared to more traditional amino modifications. Such hydrazide modified oligos have not been previously described.

The advantages of these aspects of the invention are numerous. For example, the multi-site attachment moiety modified macromolecules require a short reaction time for immobilization, allow for multiple binding sites per bound entity, provide for stability over a relatively broad pH range, and provide for the capability of attachment under both anhydrous or aqueous conditions thereby providing an improved method for attaching molecules to any solid phase surface for any applicable use.

The methods and compositions of the invention are useful in conjunction with solid phase synthesis and/or synthesis of small molecule libraries such as macromolecules including, but not limited to, DNA, RNA, PNA, p-RNA (pyranosyl-RNA), and peptides. The preferred embodiments are particularly useful in conjunction with traditional phosphoramidite chemistry synthesis techniques.

The invention is also useful for producing immobilized macromolecular components for analytical techniques that require an immobilized reagent such. As oligonucleotides with multiple attachment moieties and/or hydrazide modification may be readily made with the invention, assays such as nucleic acid hybridization based assays, SNP assays, STR assays, gene sequence quantification and identification, and the like may readily incorporate immobilized reagents produced in the invention. In addition, the methods and compounds described may be readily adapted to produce immobilized reagents for antigen or antibody diagnostics.

In a first embodiment of the invention, macromolecules are provided having a branched or dendrimeric structures connecting functional or reactive attachment moieties to the macromolecule. These modifications of the macromolecule are ideal for binding to a substrate surface which comprises binding groups which can react with or non-covalently bind to the attachment moieties on the macromolecule.

The use of oligos with multiple reactive sites or complexing agents within one oligo offers significant advantages for immobilization. First, it increases the speed of the immobilization process. One reason for this effect is that the probability for an initial productive contact between the attachment partners by diffusion is higher when one macromolecule, e.g., an oligo, bears multiple reactive sites. Additionally, the oligo can be immobilized via secondary, multiple covalent or noncovalent linkages which are formed after (or simultaneous with) the primary linkage. The formation of these secondary linkages after the primary linkage is an intramolecular process, which is kinetically favored after the intermolecular primary linkage formation because of the increased proximity (local concentration) of the reaction participants.

Second, the overall stability of the attachment increases as multiple linkages are formed between the oligo and the substrate. Simply, the energy need to completely dissociate the immobilized oligo from the substrate increases with each bond (covalent or non-covalent) which must be broken. This effect is independent of the approach used to bring the macromolecule into contact with the substrate. However, the effect with regard to a reversible covalent linkage, hydrazone formation between a hydrazide and an aldehyde, is demonstrated quite dramatically in the examples.

The formation of multiple noncovalent complexes results in a higher overall stability of the complex between the oligo and the substrate allowing the use of relatively low affinity complexing moieties to produce a stable immobilization. Some of the frequently applied immobilization chemistries for oligos are reversible in aqueous solution (e.g. the Schiff's base formation between amines and aldehydes) and require a subsequent stabilization step e.g. by reduction with NaCNBH$_3$. For these reversible reactions, the immobilization via multiple linkages is beneficial because of the higher stability of the intermediates formed prior to the stabilization reaction. In some cases the gain in stability is great enough that the stabilization reaction becomes unnecessary. In fact, this is demonstrated in the examples for the hydrazide reagents immobilized on various aldehyde-moiety containing substrates.

Third, the use of oligos with multiple attachment sites allows the production of substrates with higher oligo loading. Usually the reactive binding moieties on the substrate are in large molar excess as compared the oligos, and the improved attachment due to multiple attachment moieties can lead to better use of the available sites on the substrate through more efficient and stable oligo-substrate interactions.

Thus, in another aspect of the invention, methods are provided where the multiplicity of reactive attachment moieties provided on the macromolecules allow the macromolecules to bind, either in a covalent or a noncovalent manner, to the substrate surface. As a product of these methods, another aspect of the invention, novel substrates with macromolecules bound thereto through multiple attachment moieties, is provided. These novel modified substrates have the general structure of:

Sub-[-A$_1$-A$_2$-]$_m$-L$_b$-M$_a$ wherein the substrate (Sub) has covalently attached thereto multiple attachment moieties A$_1$ which are bound (covalently or non-covalently) to attachment moieties A$_2$, which are covalently attached to a macromolecule M$_a$ through a branched linker moiety L$_b$. Preferably, A$_1$ is bound to A$_2$ through a covalent linkage, and more preferably through a diacyl hydrazine linkage.

In embodiments where noncovalent binding is utilized, the multiplicity of attachment moieties may comprise chemical moieties such as biotin, streptavidin, phenyl boronic acid (PBA), and salicyl hydroxamic acid (SHA). In embodiments utilizing covalent attachment, any suitable reactive moiety may be utilized, e.g., those listed in table 1. A preferred moiety for use is the hydrazide moiety. Such structures may be either branched or unbranched thereby allowing for great versatility in the level of possible attachment moieties available. Thus, not only are the macromolecules provided with dendritic branching structures, but the reactive attachment moieties themselves may also be branched such that each branch has a reactive hydrazide element for use in attachment the macromolecule to a substrate surface.

In another embodiment of the immobilized macromolecule aspect of the invention, the multiplicity of attachment moieties on the macromolecule provides a means whereby macromolecules attached to a substrate surface comprising an electronically addressable microchip are protected from inadvertent removal from the attachment site on the microchip. Such removal may result from the high localized voltage and current resulting from electronic biasing of the microchip electrode. Thus, in a preferred embodiment, the multiple attachment scheme of the current invention provides for binding of macromolecules to the substrate so that the immobilization is capable of withstanding current densities of at least 4 mA/cm$^2$.

In still another embodiment, the invention provides for a method of adding reactive attachment moieties to the dendritic structures attached to the macromolecules, or to the macromolecules themselves. These reactions may occur in a single reaction step, such as, for example, by the in situ generation of hydrazides from multiple ester-precursors by hydrazine treatment, or by the addition of a branched phosphoramidite containing multiple protected hydrazines.

In still another aspect, the invention provides novel compositions of matter for the modification of macromolecules, including oligos, to add hydrazine attachment moieties. These novel modification reagents generally comprise a phosphate-bearing reactive group for biomolecular synthesis covalently attached to an aliphatic or aromatic linker moiety, which is further covalently attached to one or more protected hydrazide moieties or a hydrazide-precursor ester. In one set of embodiments of this aspect of the invention, the regents comprise at least one protected aromatic hydrazide, and have the general structure:

P$_r$—O-L$_a$-Bz-(CONHNH—P$_{Ga}$)$_m$ wherein:

Bz is a benzene ring,

L$_a$ is a branched or unbranched hydrocarbon of 1 to 12 carbons, and L$_a$ may optionally include 1 to 4 ether or amide linkages between the carbons, more preferably (CH$_2$)$_n$ wherein n is an integer between 1 and 12;

P$_r$ is a phosphorous bearing reactive group for biomolecular synthesis, preferably

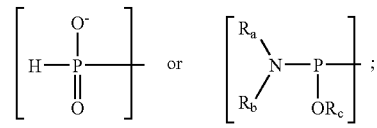

$R_a$ and $R_b$ are branched or unbranched hydrocarbons with 1 to 12 carbons, more preferably independently selected from the group consisting of methyl, ethyl, propyl, isopropyl, butyl, isobutyl, and t-butyl;

$R_c$ is selected from the group consisting of 2-cyanoethyl, allyl, methyl ethyl, and other alkyl moieties;

each $P_{Ga}$ is, independently, any protecting group suitable to protect the hydrazide during synthesis and deprotection steps, more preferably selected from the group consisting of trityl, methyltrityl, monomethoxytrityl, and dimethoxytrityl; and m is 1, 2, or 3. In preferred embodiments, m is 1 or 2.

Preferred embodiments of this set include:

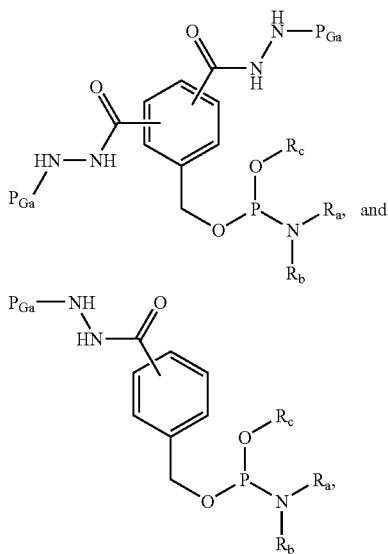

particularly where $P_{Ga}$ is monomethoxytrityl.

In another set of embodiments of this aspect, the reagents comprise one or more protected aliphatic hydrazides, and have the general formula:

$P_r$—O-$L_a$-(CONHNH—$P_{Ga}$)$_m$ wherein:

$L_a$ is a branched or unbranched hydrocarbon of 1 to 12 carbons, further wherein $L_a$ is branched if m>1, and $L_a$ may optionally include 1 to 4 ether or amide linkages between the carbons;

$P_r$ is a phosphorous bearing reactive group for biomolecular synthesis, preferably

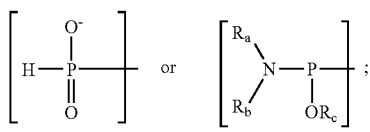

$R_a$ and $R_b$ are branched or unbranched hydrocarbons with 1 to 12 carbons, more preferably independently selected from the group consisting of methyl, ethyl, propyl, isopropyl, butyl, isobutyl, and t-butyl;

$R_c$ is selected from the group consisting of 2-cyanoethyl, allyl, methyl ethyl, and other alkyl moieties;

each $P_{Ga}$ is, independently, any protecting group suitable to protect the hydrazide during synthesis and deprotection steps, more preferably selected from the group consisting of trityl, methyltrityl, monomethoxytrityl, and dimethoxytrityl, and is most preferably trityl;

and m is 1, 2, 3, or 4. In preferred embodiments, m is 1. In other preferred embodiments, m>1.

Preferred embodiments of this set include

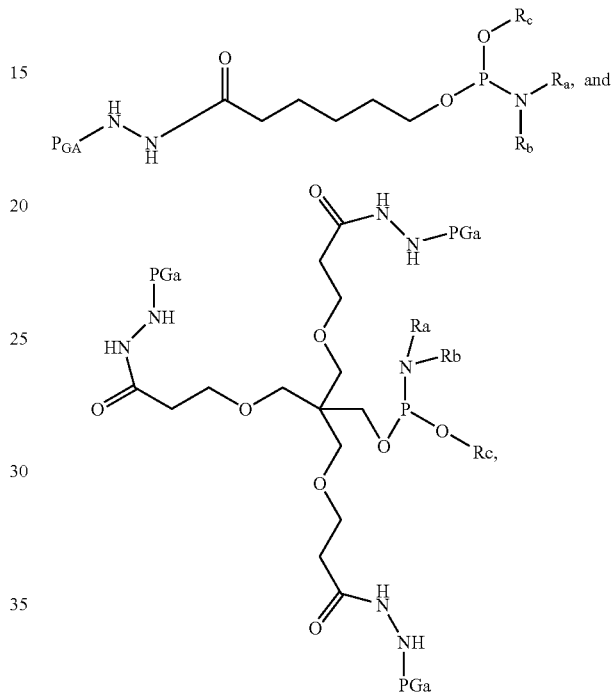

particularly where $P_{Ga}$ is trityl.

In another set of embodiments of this aspect, the reagents have three or more protected aromatic hydrazides, with the general formula:

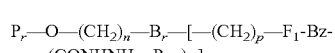

$P_r$—O—(CH$_2$)$_n$—B$_r$—[—(CH$_2$)$_p$—F$_1$-Bz-(CONHNH—P$_{Ga}$)$_m$]$_q$ wherein:

$B_r$ is a branching moiety, preferably carbon, nitrogen, or a benzene ring;

Bz is a benzene ring;

$F_1$ is a functional linkage, preferably an ether or amide linkage;

$P_r$ is a phosphorous bearing reactive group for biomolecular synthesis, preferably

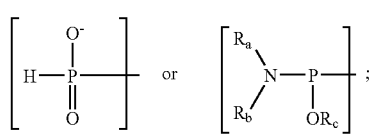

$R_a$ and $R_b$ are branched or unbranched hydrocarbons with 1 to 12 carbons, more preferably independently selected from the group consisting of methyl, ethyl, propyl, isopropyl, butyl, isobutyl, and t-butyl;

$R_c$ is selected from the group consisting of 2-cyanoethyl, allyl, methyl ethyl, and other alkyl moieties;

each $P_{Ga}$ is, independently, any protecting group suitable to protect the hydrazide during synthesis and deprotection steps, more preferably selected from the group consisting of trityl, methyltrityl, monomethoxytrityl, and dimethoxytrityl, most preferably trityl;

n and p are, independently, an integer between 0 and 12;

m is, independently, 1, 2, or 3; and q is 1, 2, or 3.

Preferred embodiments from this set include:

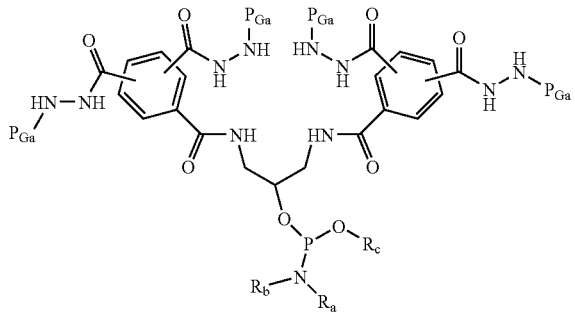

and

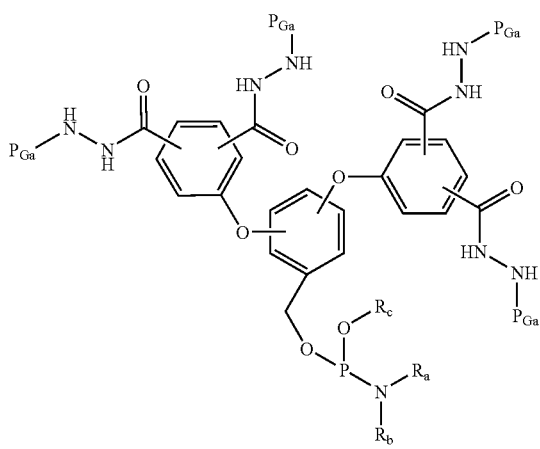

In another set of embodiment of this aspect of the invention, the reagents comprise an aromatic hydrazide-precursor ester, and have the general structure:

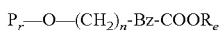

wherein:

Bz is a benzene ring, $P_r$ is a phosphorous bearing reactive group for biomolecular synthesis, preferably

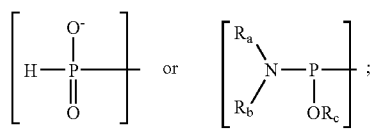

$R_a$, $R_b$, and $R_e$ are, independently, branched or unbranched hydrocarbons with 1 to 12 carbons, more preferably independently selected from the group consisting of benzyl, methyl, ethyl, propyl, isopropyl, butyl, isobutyl, and t-butyl;

$R_c$ is selected from the group consisting of 2-cyanoethyl, allyl, methyl ethyl, and other alkyl moieties; and n is an integer between 1 and 12.

Preferred embodiments of this set include:

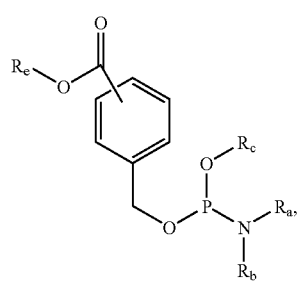

particularly those where $R_e$ is methyl.

In another set of embodiment of this aspect, the reagents have three or more aromatic hydrazides precursor esters, and have the general formula:

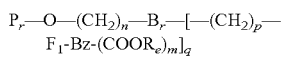

wherein:

$B_r$ is a branching moiety, preferably carbon, nitrogen, or a benzene ring;

Bz is a benzene ring;

$F_1$ is a functional linkage, preferably an ether or amide linkage;

$P_r$ is a phosphorous bearing reactive group for biomolecular synthesis, preferably

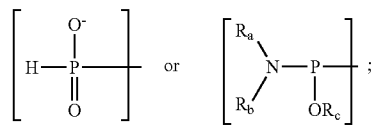

$R_a$, $R_b$, and $R_e$ are, independently, branched or unbranched hydrocarbons with 1 to 12 carbons, more preferably independently selected from the group consisting of benzyl, methyl, ethyl, propyl, isopropyl, butyl, isobutyl, and t-butyl;

$R_e$ is selected from the group consisting of 2-cyanoethyl, allyl, methyl ethyl, and other alkyl moieties;

n and p are, independently, an integer between 0 and 12;

m is, independently, 1, 2, or 3; and q is 1, 2, or 3.

Preferred embodiments of this set include

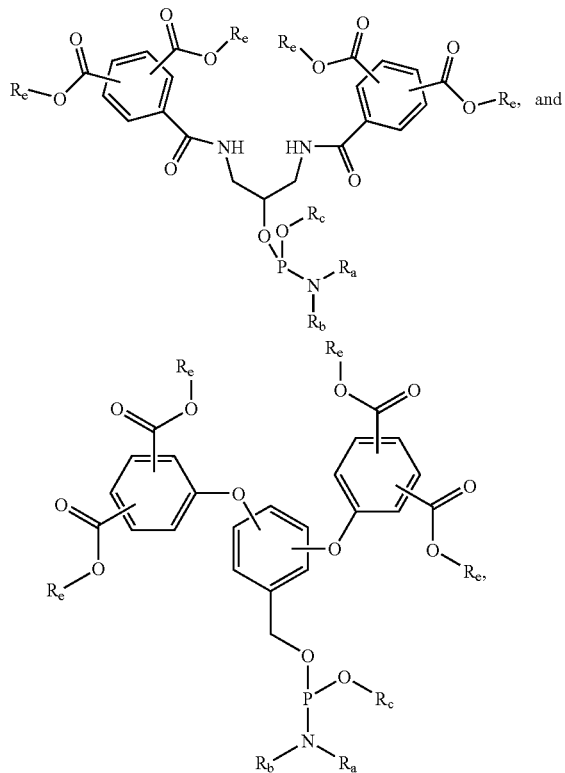

particularly where $R_e$ is methyl.

In another set of embodiments of this aspect, the reagents comprise at least one aromatic hydrazide precursor ester, as well as a protected alcohol moiety which can be used for further additions by solid-phase phosphoramidite chemistry, and have the general formula:

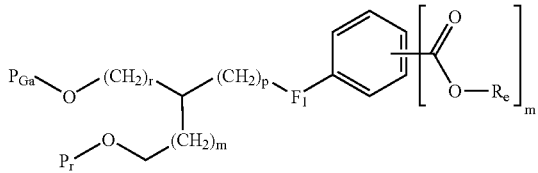

wherein:
- $B_r$ is a branching moiety, preferably carbon, nitrogen, or a benzene ring;
- $F_1$ is a functional linkage, preferably an ether or amide linkage;
- $P_r$ is a phosphorous bearing reactive group for biomolecular synthesis, preferably

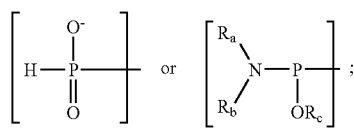

- $R_a$, $R_b$, and $R_e$ are, independently, branched or unbranched hydrocarbons with 1 to 12 carbons, more preferably independently selected from the group consisting of benzyl, methyl, ethyl, propyl, isopropyl, butyl, isobutyl, and t-butyl;
- $R_c$ is selected from the group consisting of 2-cyanoethyl, allyl, methyl ethyl, and other alkyl moieties;
- $P_{Ga}$ is any protecting group suitable to protect the alcohol during synthesis and deprotection steps, more preferably selected from the group consisting of trityl, methyltrityl, monomethoxytrityl, and dimethoxytrityl;
- n, p, and r are, independently, an integer between 0 and 12; and
- m is 1, 2, or 3.

In another aspect, the invention also provides novel macromolecules, preferably oligos, which have been modified with any of the above reagents to contain one or more hydrazides or hydrazide-precursor esters. These hydrazides comprise reactive groups and can be used for the conjugation of oligos to fluorophores or other small molecules, to peptides, proteins or antibodies, or to substrate surfaces.

Thus, in yet another aspect of the invention, modified macromolecules linked through their hydrazide attachment moieties to a substrate surface are provided by the present invention. These novel modified substrates have the general structure of:

$$\text{Sub-[-R}_H\text{—N(H)}_n\text{NHOC-]}_m\text{-L-P}_L\text{-M}_a$$

wherein the substrate (Sub) has covalently attached thereto a linkage moiety $R_H$ comprising a hydrazide-reactive center.

In preferred embodiments, $R_H$ comprises a reactive center covalently attached to the hydrazide selected from the group consisting of carbonyl (—CO—), —CH$_2$—, —CH=, —CHOH—, and

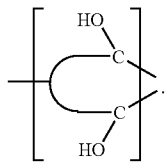

In more preferred embodiments, $R_H$ comprises a carbonyl reactive center. $R_H$ is covalently attached to at least one hydrazide, wherein n=0 if the hydrazide is attached to $R_H$ by two bonds, and n=1 if the hydrazide is attached to $R_H$ by a single bond. The hydrazide is covalently attached to a branched or unbranched linker moiety $L_H$. $L_H$ is a branched or unbranched, substituted or unsubstituted, aromatic or aliphatic, hydrocarbon linker moiety containing 1 to 50 carbon atoms and optionally containing 1 to 10 heteroatoms in functional linkages, wherein the heteroatoms are selected from the group consisting of O, N, S, and P, and wherein $L_H$ is branched if m>1. $L_H$ is covalently attached to a phosphate-linker group $P_L$ (which is a phosphate which may or may not be charged or comprise an alkyoxy or cyanoalkyoxy group), which is covalently attached to a modified macromolecule $M_a$, preferably an oligo.

In still another aspect of the invention, the attachment scheme can be applied to surface synthesis of macromolecules and analytical applications requiring surface immobilization of compounds.

BRIEF DESCRIPTION OF THE DRAWINGS

FIG. 9C shows a scheme wherein the hydrazide-labeled oligo can react with an activated-ester monomer and used to form a substrate for immobilization of macromolecules.

FIG. 25B are the actual fluorescent photo images of the oligomers bound to the glass slide, their binding levels are displayed graphically in FIG. 25A.

FIG. 26B are the actual fluorescent photo images of the oligomers bound to the glass slide, their binding levels are displayed graphically in FIG. 26A.

DETAILED DESCRIPTION OF THE PREFERRED EMBODIMENTS

Figure 1:
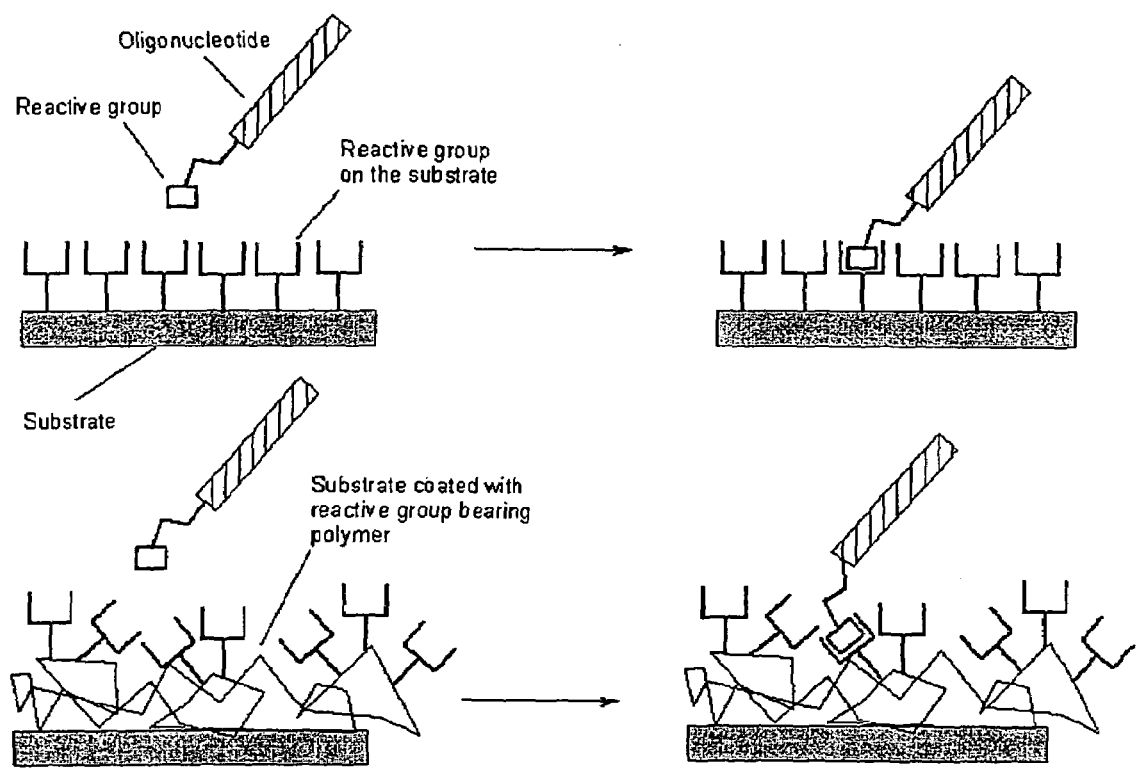
FIG. 1 is a schematic depicting the classic approach for immobilizing oligos on planar substrates. Generally, a single reactive group is used to bind the oligomer to the substrate surface.

Referring now to the specific embodiments of the invention, macromolecules are provided having a multiplicity of substrate surface attachment moieties.

By "macromolecule" is meant a relatively large organic molecule. These include biologically relevant molecules that is used to contact molecular entities in a test sample, i.e., those that can interact with other macromolecules derived from a biological source, such as, for example, nucleic acids, antigens, antibodies, and enzymes. Generally, these include, at least in part, molecules such as nucleic acids, including oligonucleotides and polynucleotides, DNAs, RNAs, or chemically modified nucleic acid mimics such as p-MeNAs (methyl or methoxy phosphate nucleic acids), peptide nucleic acids (PNAs), and locked nucleic acids (LNAs). Macromolecules also include unnatural or synthetic molecules structurally derived from the naturally occurring molecules such as CNAs (cyclohexyl nucleic acids), p-RNAs (pyranosyl RNAs), p-DNAs (pyranosyl DNAs), and other molecules which are complex polymeric structures which do not interact with biologically derived nucleic acids or other molecules, but which share structural complexity. For convenience, all such polymeric type molecules comprising chemically linked monomer units consisting of bases covalently bonded to sugar rings, including natural/biologically active oligonucleotides (e.g., DNA, RNA, PNA, etc.) and non-biologically active molecules such as p-RNA, p-DNA, and CNA, are included in the term "oligos" as used herein. This is a modification of the common usage as a shortened form of "oligonucleotides", as technically the monomeric units of the synthetic macromolecules are not nucleosides. Oligos may be advantageously modified with attachment moieties for binding the macromolecule to a substrate surface.

Macromolecules also include proteins, peptides, enzymes, and antibodies, which may also be modified with attachment moieties for binding the macromolecule to a substrate surface.

Having such an attachment moiety, macromolecules may also be referred to as "derivatized" or "modified" macromolecules. Such macromolecules therefore also include oligonucleotides containing oxidized ribose, amine terminations, or any entity of the well known bioconjugate pairs as outlined by Hermanson (Hermanson, G. T. *Bioconjugate Techniques* copyright 1996, Academic Press, San Diego, Calif.) herein incorporated by reference, and/or alternative non-nucleic acid structures such as pRNAs (in reference to pRNAs as described in co-pending application Ser. No. 09/374,338 filed Aug. 13, 1999 herein incorporated by reference).

Generally, attachment of the chemical moieties to the macromolecules comprises a covalent bond. With respect to attachment of derivatized macromolecules to a substrate surface, such attachment may use either a covalent or a noncovalent bond. As will be evident from the disclosure, the attachment moieties of the invention described explicitly herein are preferably covalently attached utilizing phosphoramidite linkage chemistry. Thus, phosphate-backbone nucleic acids such as DNA, RNA, p-MeNAs, etc., and phosphate-backbone non-nucleic acid polymeric structures such as pRNA and pDNA are somewhat preferred for use as macromolecules for modification with the disclosed attachment moieties, as the phosphoramidite attachment may be readily incorporated into standard techniques for their solid-phase synthesis. However, methods of utilizing phosphoramidite reagents for the modification of other biomolecules and synthetic structures (particularly through primary alcohols) are well known, and the person of ordinary skill would be able to make minor modifications to the disclosed procedures to couple the disclosed phosphoramidite attachment moiety molecules to non-phosphate backbone type macromolecules (e.g., PNA, CNA, peptides, etc).

By "attachment moiety" is generally meant any chemical moiety utilized in the attachment of macromolecules to a substrate surface. A attachment moiety may be contained on a macromolecule or contained on a substrate surface. Table 1 Attachment Moieties provides a list of attachment moieties used.

TABLE 1

Attachment Moieties

| Structure | Functional Group or Chemical Name |
|---|---|
| X—OH | Alcohol |
| X—O—R | Ether |
| X—NH$_2$ | Primary amine |

TABLE 1-continued

Attachment Moieties

| Structure | Functional Group or Chemical Name |
|---|---|
| X–NHR | Substituted amine |
| X–CH₂–N(H)–NH₂ | Hydrazine |
| X–SH | Sulfhydryl |
| (epoxide structure with X) | Epoxide |
| (aziridine structure with X) | Aziridine |
| CH₂=CR–X (R = C, N, O, P, S) | Vinyl |
| CH₂=CH–CH₂–R–X (R = C, N, O, P, S) | Allyl |
| X–C(=O)–H | Aldehyde |
| R–C(=O)–X | Ketone |
| X–CH(O–R)(O–R) | Acetal |
| R–S–S–X | disulfide |
| X–CH₂–C(=O)–OR | Ester |
| X–CH₂–C(=O)–OH | Carboxylic Acid |
| X–CH₂–C(=O)–NH₂ | Amide |
| X–CH₂–C(=O)–N(H)–R | Monosubstituted Amide |

TABLE 1-continued

Attachment Moieties

| Structure | Functional Group or Chemical Name |
|---|---|
| X–CH₂–C(=O)–N(R)(R₁) | Disubstituted Amide |
| X–N(H)–C(=O)–CH₂–Y (Y = Br, I) | Bromo- or Iodo-acetamide |
| X–C(=O)–N(H)–NH₂ | Hydrazide |
| R–S–C(=O)–X | Thioester |
| X–O–C(=O)–O–N(succinimidyl with Y) (Y = H, SO₃Na) | (sulfonated)-N-Hydroxy succinimidyl ester |
| (oxazolone structure with X) | Azlactone, an activated ester |
| X—N=C=O | Isocyanate |
| X—N=C=S | Isothiocyanate |
| X–C(=O)–N⁺≡N | Acyl azide |
| X–O–C(=O)–O–R | Carbonates |
| R₃–O–P(–O–R₂)(–N(R)(R₁)) | phosphoramidites |

Symbols: X = a macromolecule or substrate/solid support;
R, R₁, R₂, R₃ = organic carbon moieties unless otherwise indicated.

By "Lewis Base" is generally meant any chemical moiety capable of donating a pair of electrons to an electron deficient center. In a preferred embodiment, a Lewis Base is more specifically referred to as a "nucleophile" in which a reactive center donates a pair of electrons to carbon resulting in a covalent bond between the reactive center and the carbon as recognized by one skilled in the art (For an expanded definition see: Smith, M. B. *Organic Synthesis* copyright 1994 McGraw Hill Inc., New York, N.Y., or any organic chemistry textbook).

By "Lewis Acid" is generally meant any electron deficient chemical moiety capable of receiving a pair of electrons. In a preferred embodiment, a Lewis Acid is more specifically referred to as an "electrophile" which is a reactive center capable or receiving a pair of electrons from a nucleophile as recognized by one skilled in the art. (For an expanded definition see: Smith, M. B. *Organic Synthesis* copyright 1994 McGraw Hill Inc., New York, N.Y., or any organic chemistry textbook). In a preferred embodiment, as an example, salicylic hydroxamic acid is capable of acting as a Lewis base donating a pair of electrons to boron, a Lewis acid, of phenyl boronic acid resulting in a noncovalent linkage. In yet another preferred embodiment, as an example, a hydrazide moiety is capable of acting as a nucleophile donating a pair of electrons to the reactive carbon center of an NHS ester, an electrophile, forming a covalent linkage to said carbon center.

By "branched linking moiety" is generally meant any chemical species which is capable of coupling through a specific reactive moiety to a macromolecule and is also capable of further attachment to more than one molecule through alternative reactive centers. In a preferred embodiment, a branched linking moiety is a phosphoramidite, of which examples are shown in Table 2, Entries 1–4. In these examples, the phosphorus acts as the reactive moiety while the esters of entries 1, 2, and 3 and the protected alcohols of 4 are alternative reactive centers.

By "branched linking structure" is generally meant a macromolecule resulting from treatment of a macromolecule with a branched linking moiety. The alternative reactive centers of the branched linking moiety are now contained within the branched linking structure. In an exemplary embodiment, a branched linking structure is represented by entry 5 of Table 2 in which the macromolecule shown is the result of treating a macromolecule with a branched linking moiety, specifically the compound displayed in entry 4 of Table 2. In another preferred embodiment the branching linking structure is capable of being combined in a homogeneous series in which a macromolecule is modified with a branching linking moiety, which in turn is further modified by the same branched linking moiety through the alternative reactive centers of the resultant branched lining structure, generating a new branched linking structure. This construction of larger branched linking structures by means of a series of linkages of a branched linking moiety can be further continued as shown in Table 2, Entries 6–8 In yet another embodiment, the branching linking moieties are capable of being combined in a heterogeneous series in which a macromolecule is modified with a branching linking moiety, which in turn is further modified by a different branched linking moiety through the alternative reactive centers of the initial branched linking moiety, generating a new branched linking structure. This construction of larger branched linking structures by means of a series of linkages of branched linking moieties can be further continued as shown in Table 2, Entries 9–12.

TABLE 2

Branched Linking Moieties and Branched Linking Structures

| Entry | Chemical Structure | Name or class of compound |
| --- | --- | --- |
| 1 | 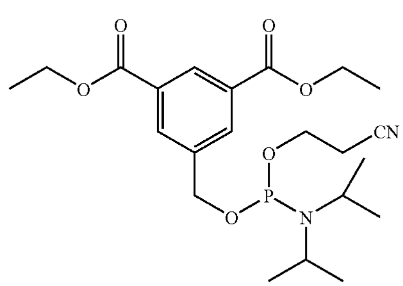 | Branched Linking Moiety: Diethyl 5-{[(2-cyanoethoxy)(diisopropylamino)phosphanyloxy]methyl}isophthalate; Compound 1c; a diester phosphoramidite |
| 2 | 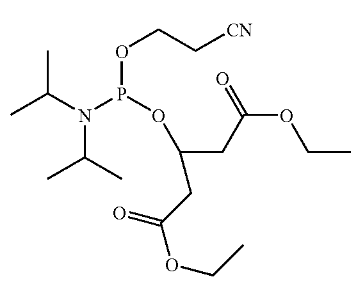 | Branched Linking Moiety: Diethyl 3-[(2-cyanoethoxy)(diisopropylamino)phosphanyloxy]glutarate; a branched diester phosphoramidite. |

TABLE 2-continued

Branched Linking Moieties and Branched Linking Structures

| Entry | Chemical Structure | Name or class of compound |
|---|---|---|
| 3 | 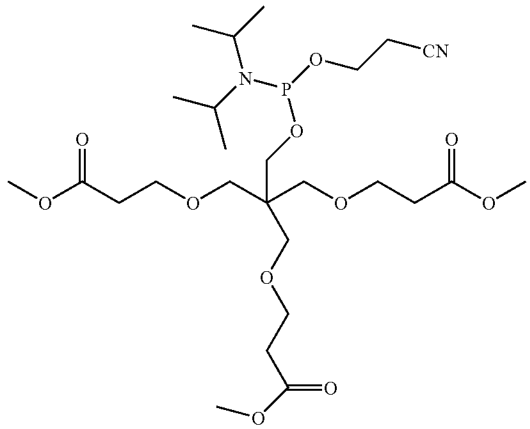 | Branched Linking Moiety: Dimethyl 3,3'-(2-{[(2-cyanoethoxy)(diisopropylamino)phosphanyloxy]methyl}-2-{[2-(methoxycarbonyl)ethoxy]methyl}propane-1,3-diylbisoxy)dipropionate; Compound 1d; a tri-ester phosphoramidite |
| 4 | 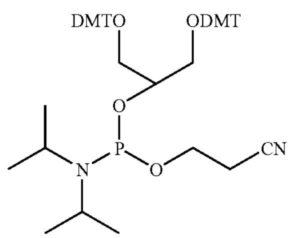 | Branched Linking Moiety: 1,3-bis-((di p-methoxyphenyl)-phenylmethoxy)-2-propyl O-2-cyanoethyl-N,N-diisopropylamino phosphoramidite; a symmetrically branched phosphoramidite. DMT = di-(p-methoxyphenyl)-phenylmethyl |
| 5 | 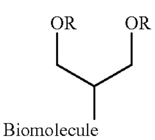 | First generation branched linking structure in which the alternative reactive species is an alcohol (R = H) or a protected alcohol (R = DMT). |
| 6 | 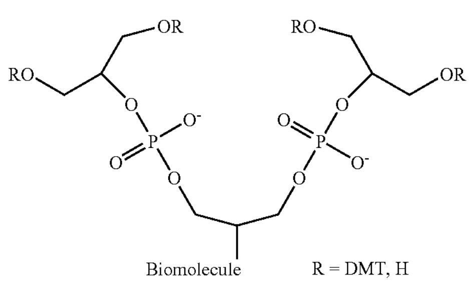 | Second generation homogeneous branched linking structure in which the alternative reacting species is an alcohol (R = H) or a protected alcohol (R = DMT). |

TABLE 2-continued

Branched Linking Moieties and Branched Linking Structures

| Entry | Chemical Structure | Name or class of compound |
|---|---|---|
| 7 | 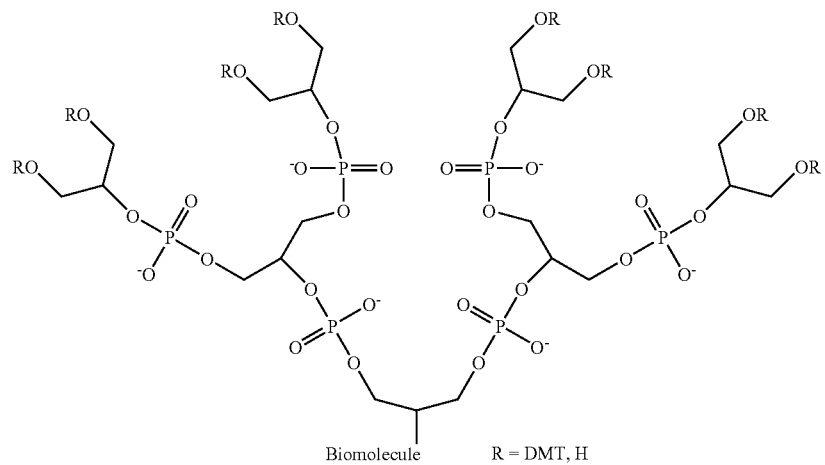 | Third generation homogeneous branched linking structure in which the alternative reacting species is an alcohol (R = H) or a protected alcohol (R = DMT). |
| 8 | 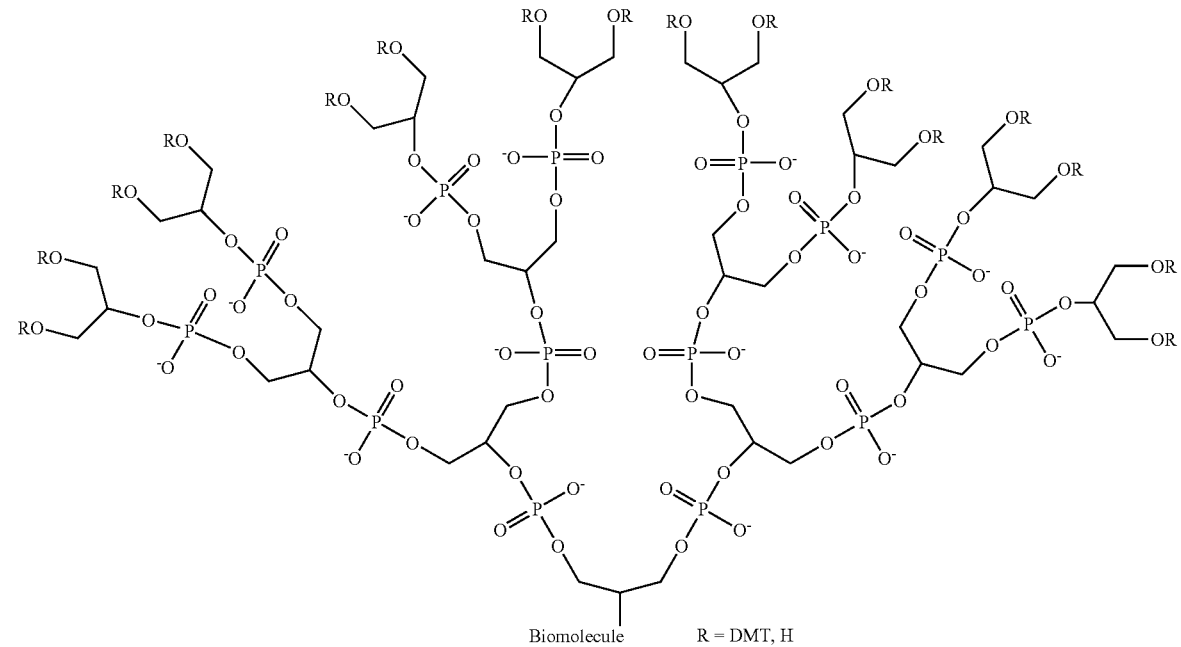 | Fourth generation homogeneous branched linking structure in which the alternative reacting species is an alcohol (R = H) or a protected alcohol (R = DMT). |

TABLE 2-continued
Branched Linking Moieties and Branched Linking Structures
| Entry | Chemical Structure | Name or class of compound |
|---|---|---|
| 9 | 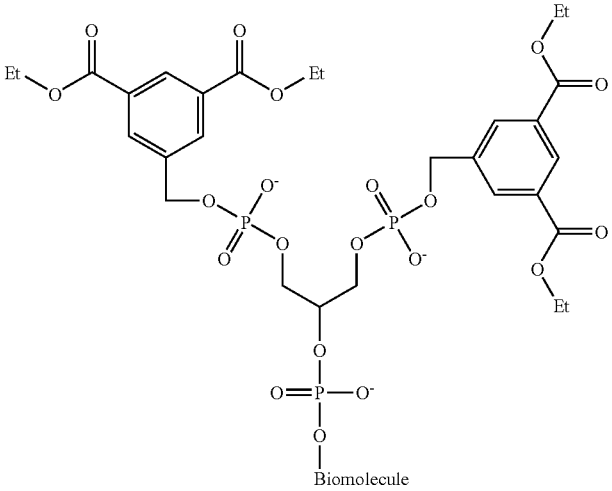 | Second generation heterogeneous branced linking structure. |
| 10 | 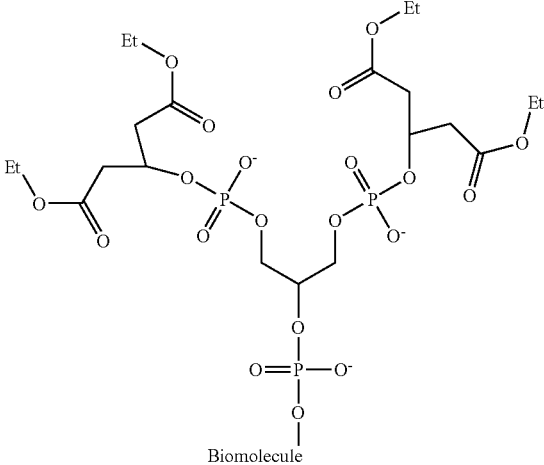 | Second generation heterogeneous branced linking structure. |

TABLE 2-continued

Branched Linking Moieties and Branched Linking Structures

| Entry | Chemical Structure | Name or class of compound |
|---|---|---|
| 11 | 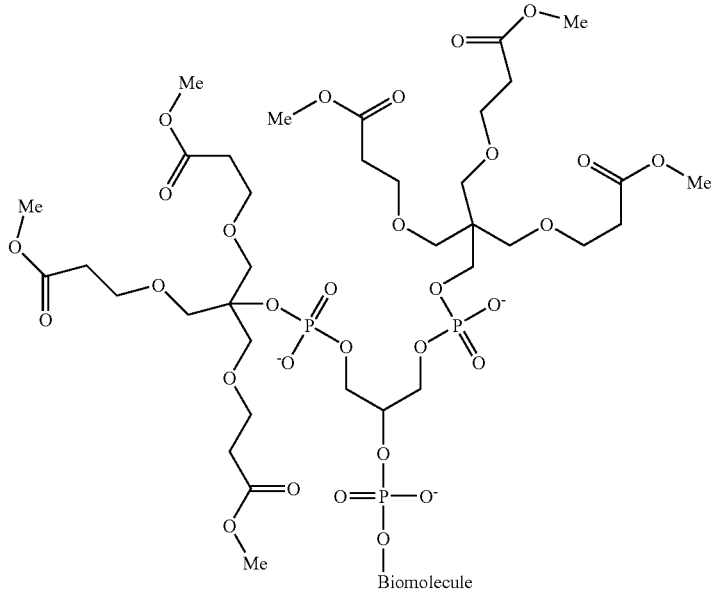 | Second generation heterogeneous branced linking structure. |
| 12. | 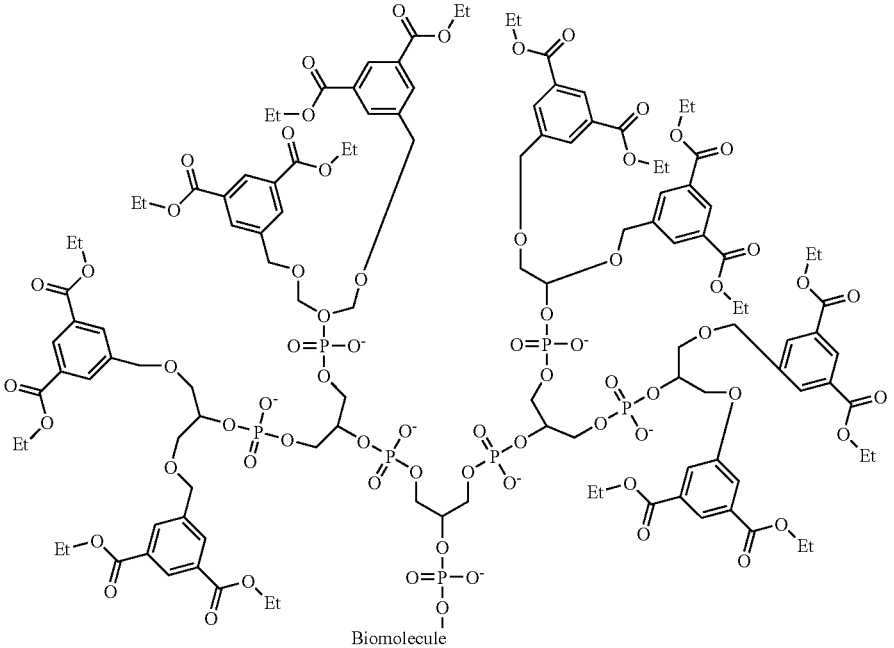 | Third generation heterogeneous branced linking structure. |

Figure 18:
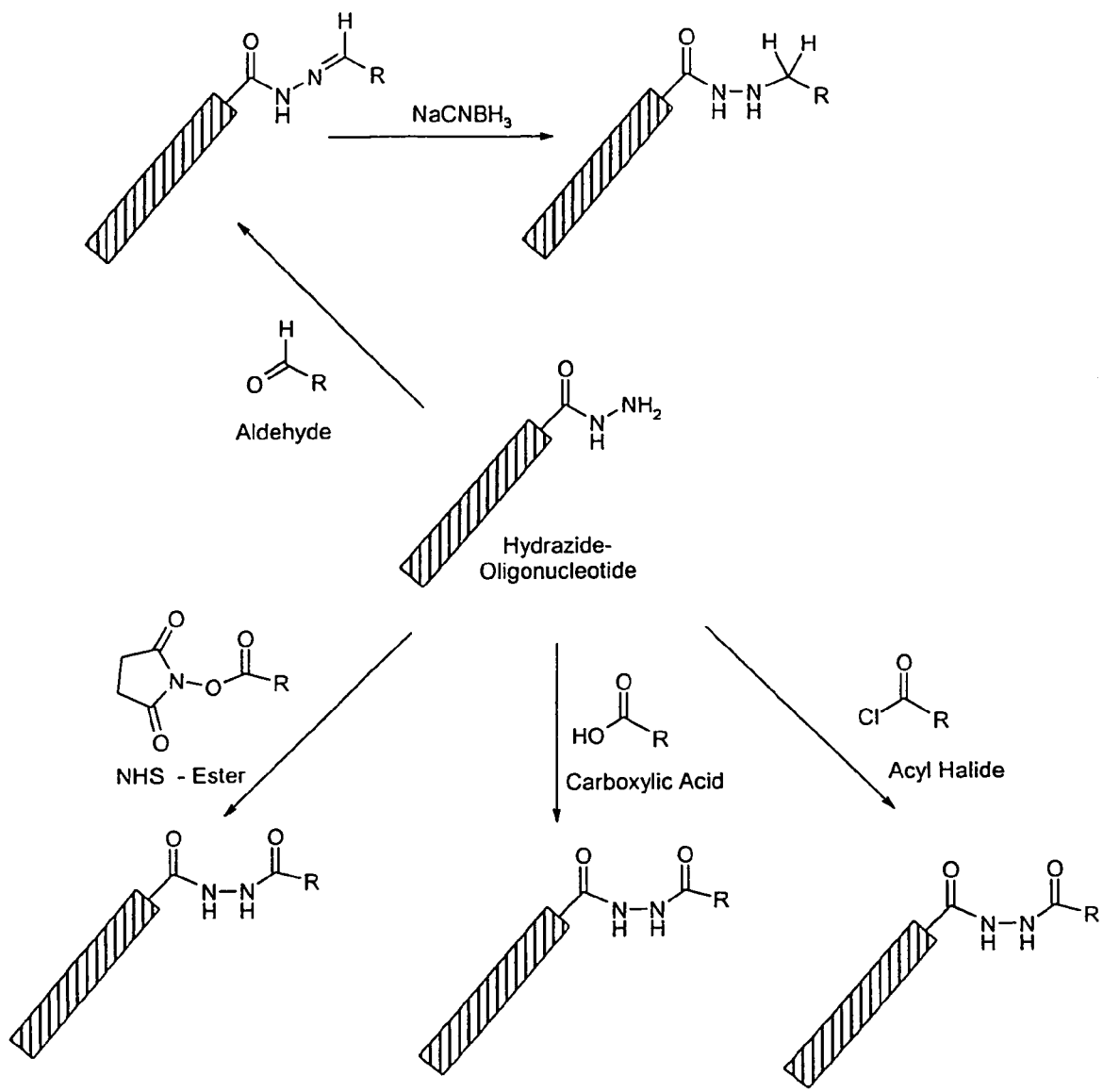
FIG. 18 shows a schematic illustrating the various functional groups which are capable of reacting with hydrazide modified oligomers.

By "substrate" is generally meant any material whose surface contains moieties with which the reactive attachment moieties of the macromolecules (e.g., single or multiple hydrazide attachment moieties) may couple. The substrates can be in any useful shape, including planar surfaces, microwells, dipsticks, beads, etc. Thus the substrate can be, among others, a glass slide, a functionalized glass slide, a chemically activated microchip surface, a surface covered with a single or multiple layers of reactive molecules, or a surface covered with a polymer or hydrogel (synthetic polymer or natural) having moieties with which the multiple reactive attachment moieties of the macromolecules may react. The substrate material to which the macromolecule is attached (i.e., that at the surface of the substrate) may be any suitable material, depending primarily on the use for the immobilized macromolecule. Exemplary substrate materials include silicon based materials (e.g., silicon, glass, functionalized glass, silicon nitride, ceramics, sol-gels, etc.) metals and metal silicilides (e.g., platinum, gold, titanium, aluminum, tungsten, alloys thereof, etc.), polymers and plastics (such as, for example, polycarbonates, polyalkylenes (e.g., polyethylenes, polypropylenes), polyesters, polyacrylates and polymethacrylates, nylon, polyvinyl halides, copolymers thereof, etc.), hydrogels (such as, for example, synthetic hydrogels like polyacrylamides or polymethacrylamides, polyepoxides, polyalkylene glycols; or carbohydrate based hydrogels, such as agarose), or naturally derived materials such as chitosan, cellulose, or even collagen matrices. In a preferred embodiment, a substrate surface is a permeation layer of an electronically addressable microchip. In particularly preferred embodiments, the permeation layer is comprised of a hydrogel which has been modified to comprise the reactive moieties on and/or within the hydrogel. Preferred hydrogels include synthetic polymer hydrogels such as polyacrylamide and polymethacrylamide. Another preferred group are carbohydrate hydrogels such as agarose. In a preferred embodiment, the functional, chemically active, or reactive moieties of a substrate are selected from (but not limited to) the functional groups listed in Table 1. In particularly preferred embodiments, the substrate reactive moieties are selected from aldehydes, N-hydroxy succinimidyl esters, sulfonated N-hydroxy succinimidyl esters, carboxylic acids, and acyl halides. These groups are particularly useful for reaction with hydrazide moieties as shown in FIG. 18.

By "precursor" is generally meant any reactive moiety which can be transformed to an alternative reactive moiety with treatment of one or more chemical reagents. In a preferred embodiment, as an example, the three ester moieties of 1d, (Entry 3 of Table 2) are precursors to hydrazides. They are transformed to a hydrazide moiety with the treatment of hydrazine.

Figure 9A:
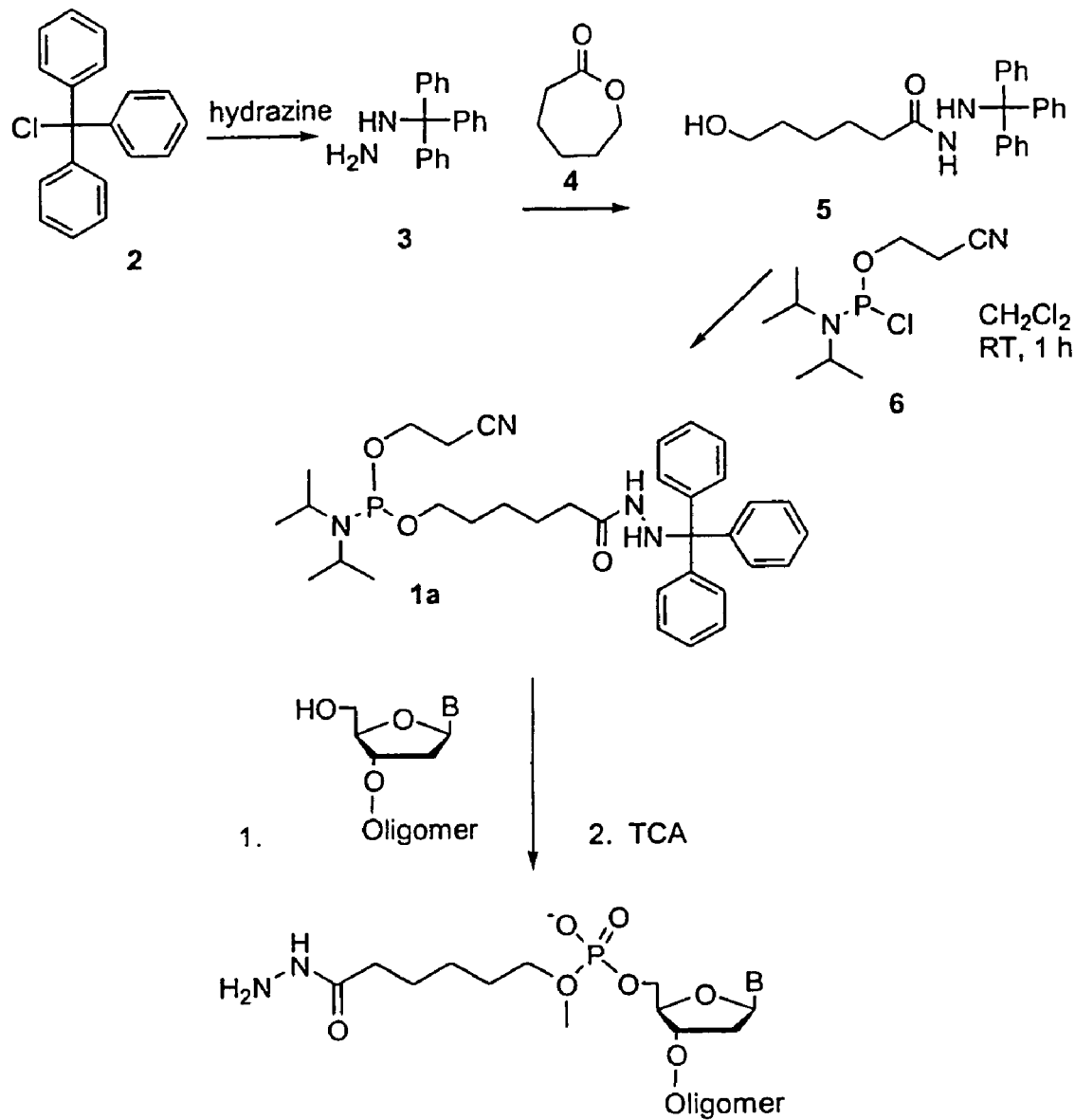
FIGS. 9A–C show three schemes of which A and B show steps for making a novel phosphoramidite for incorporation into an oligo macromolecule.

By "protected" is generally meant blocking the reactivity of a reactive moiety with one or more reagents while a chemical reaction can be carried out at an alternative reactive site of the same compound without obstruction or complication from the initial reactive moiety. Upon completion of the transformation at the alternative reactive site the protecting group of the reactive moiety can be removed, unblocking the reactive center. Preferred protective moieties include trityl, methyltrityl, monomethoxytrityl, and dimethodxytrityl. In particularly preferred embodiments, trityl is used rather than, e.g., dimethoxytrityl. Applicants have found that trityl is more stable during synthesis and purification steps than the other protecting groups. In a preferred embodiment, a protected moiety is a specific type of precursor. In yet another preferred embodiment, as an example, the hydrazide moiety of 1a of FIG. 9A is protected with a trityl group. Upon addition of 1a to a macromolecule, the trityl group is chemically removed deprotecting the hydrazide functionality.

By "activatable" is generally meant any functional group which is capable of undergoing a transformation to a reactive moiety when treated with one or more chemical reagents. By "activated" is meant a functional group which has undergone such a transformation to a reactive moiety. In a preferred embodiment, an activatable moiety can be a protected moiety or a precursor. In yet another preferred embodiment, the functional group is generally considered benign, unreactive, or incapable of binding to a substrate or macromolecule. Upon treatment with one or more chemical reagents, the functional group is transformed to a moiety capable of binding to a substrate or macromolecule. In a preferred embodiment, as an example, the ester groups of the compounds listed in Table 2 Entries 1–3 are transformed to hydrazides with treatment with hydrazine. In yet another preferred embodiment, as an example, a substrate containing acetal groups is generally considered to be unreactive. Upon treatment with an acidic source, the acetals are transformed to aldehydes which are capable of binding to hydrazide modified macromolecules.

By "microarray" is generally meant a geometric arrangement of a plurality of locations containing defined macromolecules, such individual locations being restricted to linear dimensions of 1 mm or less. Microarrays include an electronically addressable microarray such as an array designated the "APEX chip", or the "NanoChip™", and the structures described in U.S. Pat. Nos. 5,632,957, 6,254,827, 6,245,508, and 6,238,624, herein incorporated by reference in their entirety.

Overview

Figure 2:
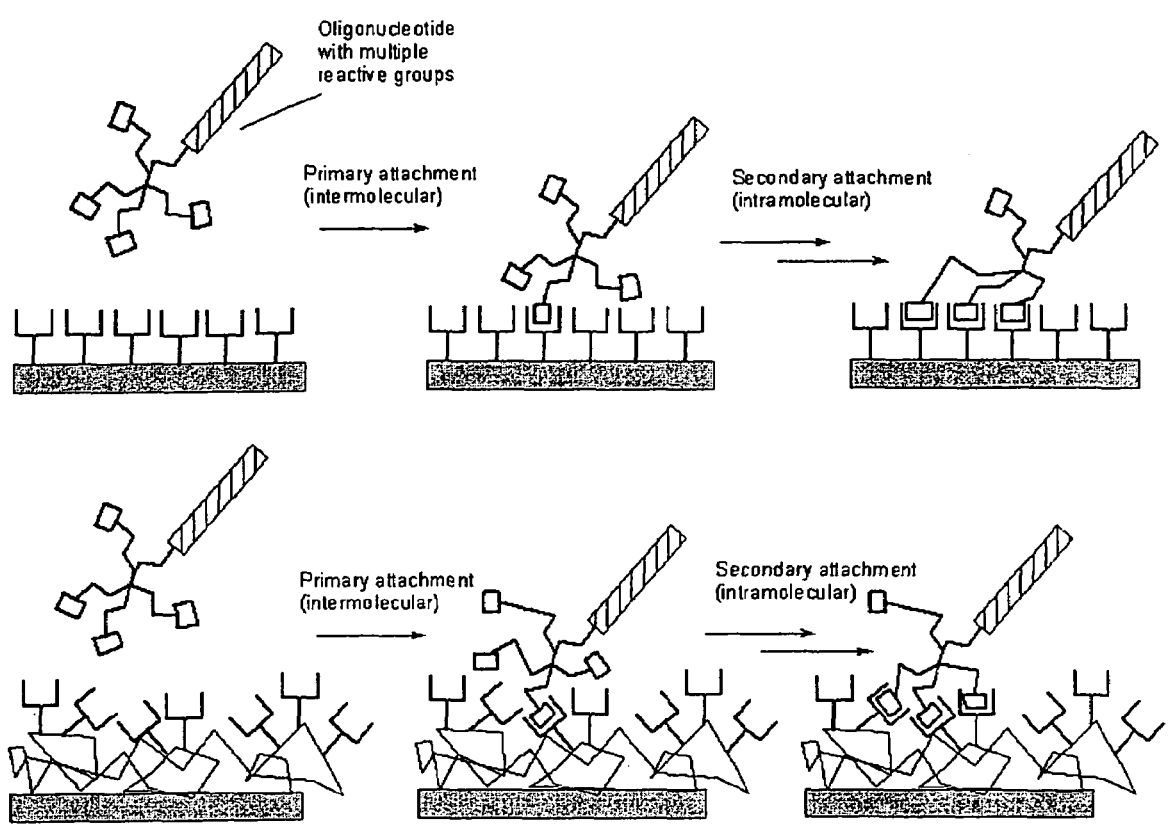
FIG. 2 is a schematic depiction of the immobilization approach of the invention wherein the macromolecule has a multiplicity of attachment or attachment moieties that can participate in the covalent or noncovalent binding of the macromolecule to the substrate.
Figure 3:
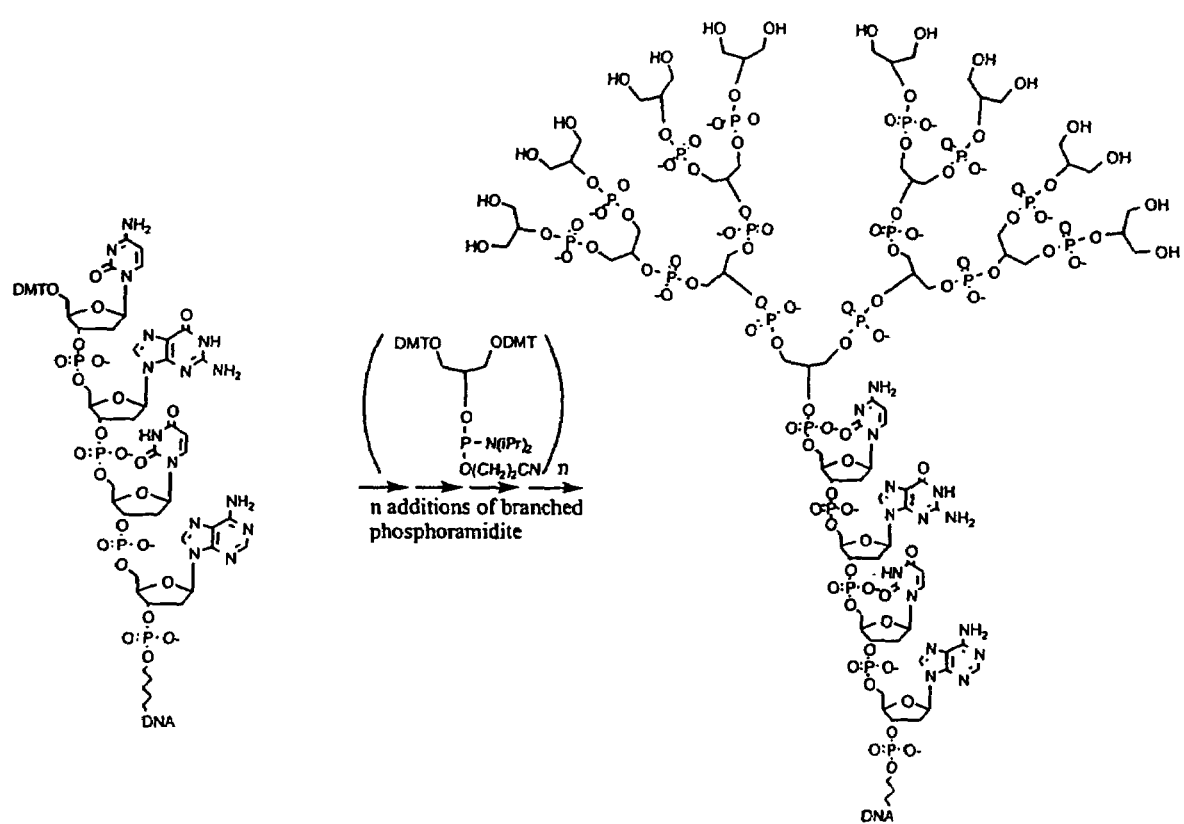
FIG. 3 is a more detailed view of one example of a nucleic acid strand attached to a multiplicity of reactive moieties for binding to a substrate surface. In this example, the chemical structures of branched phosphoramidites are added in multiple fashion to create a dendrimeric structure attached to the macromolecule.

FIG. 2 shows a basic schematic for immobilized macromolecules of the invention, wherein the macromolecules are bound to a substrate surface through a multiplicity of attachment moieties. The multiples of attachment moieties may be provided to a macromolecule using the following methods. Each of these approaches is compatible with standard solid phase synthesis of oligos, particularly using phosphoramidite chemistry techniques.

1. Preparation of Oligos with Multiple Attachment Sites 1.1 Oligo Synthesis with Branching Phosphoramidites:

Branched phosphoramidites are commercially available (Chemgenes, Ashland, Mass.; Glenn Research, Sterling, Va.), and oligonucleotides (DNA, RNA and chemically modified versions) may be ordered from commercial sources with branched phosphoramidites attached at the 3' or 5' end. After one or more consecutive couplings of such branching amidites in the solid-phase oligo synthesis (FIGS. 5A and B), oligos with two or more terminal hydroxyl groups are generated. Additional phosphoramidite building blocks introducing branches into the oligo can be applied here in a similar manner, or these hydroxyl groups can be reacted with a second type of phosphoramidite to generate the reactive group (i.e. the attachment moiety) for the attachment of the macromolecule to the substrate. This phosphoramidite can be chosen from several available amidites such as biotin amidites (e.g. Glenn Research, Cat No. 10595002), amino modifiers (e.g. Glenn Research, Cat. No. 10190602), thiol modifiers (e.g. Glenn Research, Cat. No. 10192602), phenylboronic acid amidites (Prolinx, Bothell, Wash.) and others.

In preferred embodiments, phosphoramidites containing hydrazides, in particular the novel hydrazide or hydrazide-precursor phosphoramidite reagents described herein, form (FIG. 9A) can be used. The result is an oligo having two or more (preferably 2 to 8) reactive groups, depending on the number of branching phosphoramidites and the type of attachment moiety phosphoramidite used. Phosphoramidites useful for introducing a single-hydrazide or precursor include:

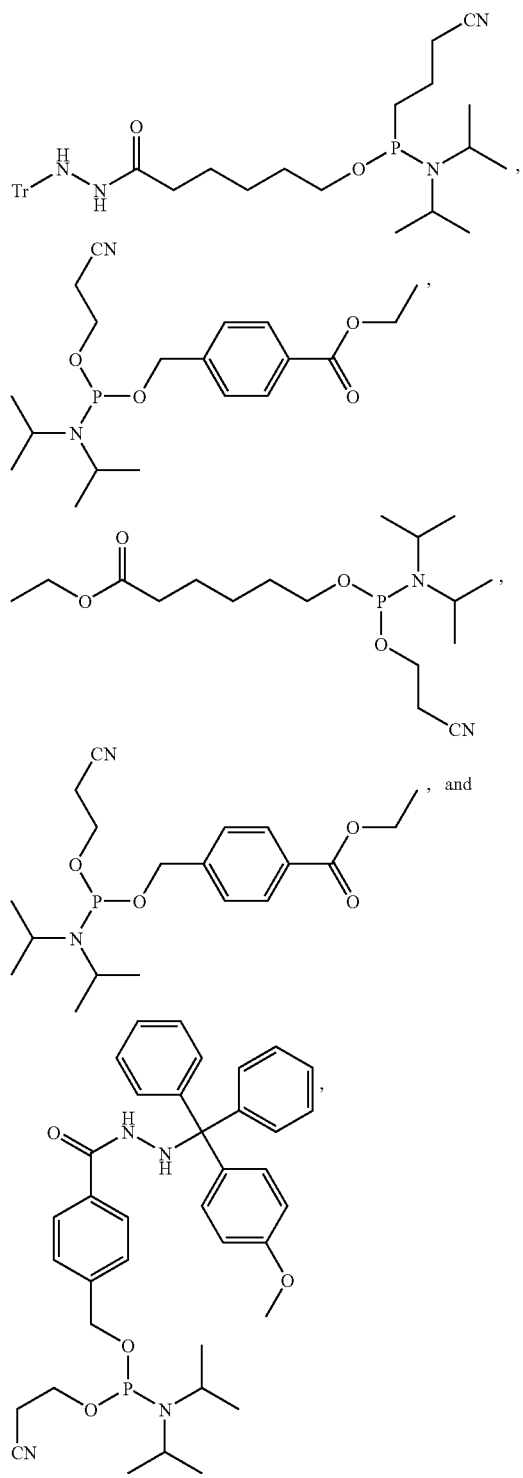

although any of the single protected hydrazide or hydrazide-precursor ester reagents described generally above may be used.

In alternative embodiments, a macromolecule or oligo which is synthesized on a solid phase may be reacted with one of the single-hydrazide or hydrazide-precursor ester reagents to produce, after deprotection or hydrazine treatment, a mono-hydrazide modified macromolecule. These modified macromolecules, including oligos, are desirable for use in non-substrate conjugation reactions (e.g., when a labeling moiety [such as, for example, fluorophores, colorigenic moieties, chemiluminescent moieties, quenchers, radioactive moieties, visible dye or particle moieties, magnetic or paramagnetic particles, and less preferably labeling enzymes, etc.] is to be attached to the macromolecule.) As discussed above, these methods are particularly adaptable to use in the synthesis of phosphate-backbone type oligos, but they may be easily adapted for the addition of the reactive-phosphate group reagents to any macromolecule having a free hydroxyl group.

1.2 Production of Oligos Having more than One Reactive Group for Attachment:

Although the above branching structure building process using branching phosphoramidite reagents is very flexible, and allows the production of complex, extended dendrimeric structures, the process has certain drawbacks for commercial production. Each level of structure development requires another round of phosphoramidite addition and deprotection in the synthesis process. In addition, the branching phosphoramidite reagents used are rather expensive for mass synthesis. Macromolecules with multiple attachment sites can also be obtained by the coupling of special phosphoramidites having in a protected or precursor form more than one reactive group for the immobilization at the substrate. The reactive group in branched amidites can be again one of the known functionalities such as amino groups, thiols, aldehydes, or hydrazides, and are preferably protected hydrazides.

Several of the building block reagents described which can introduce multiple (two, three) hydrazides with one coupling are hydrazide-precursor ester reagents. These biomolecules have to be deprotected with hydrazine to generate the active hydrazide moiety. Useful hydrazide-precursor ester reagents include

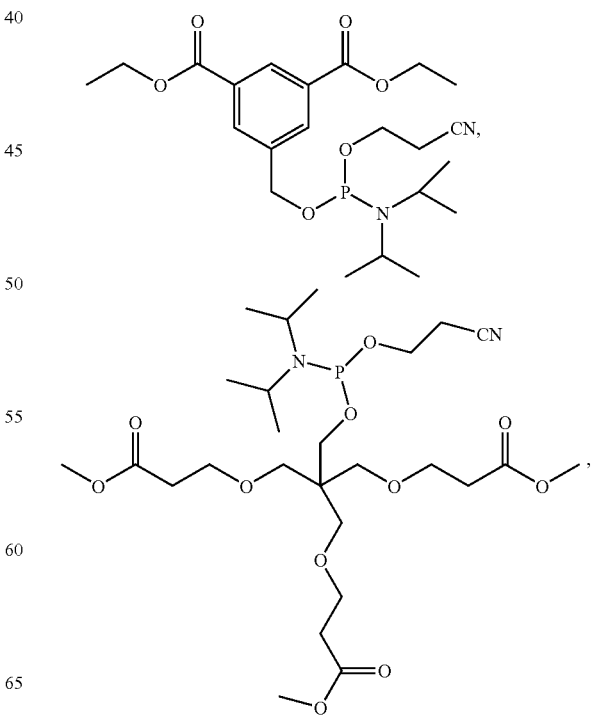

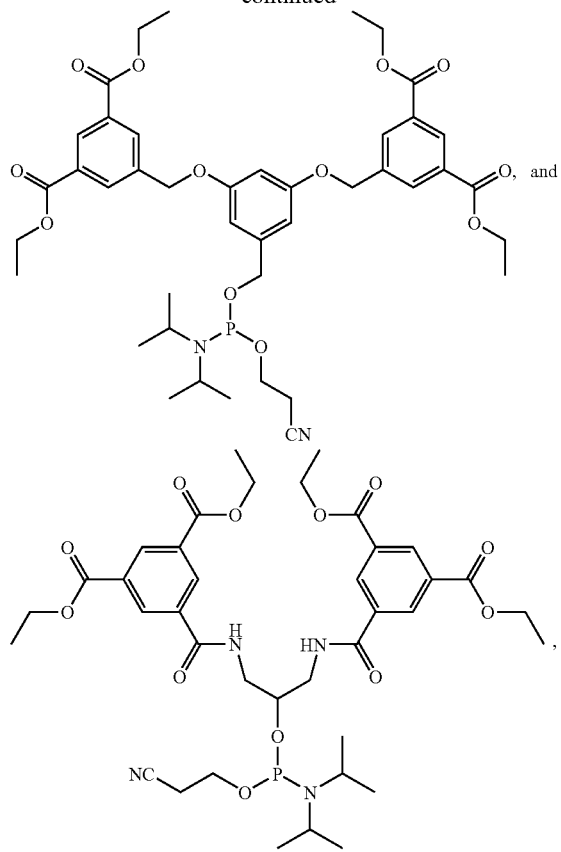

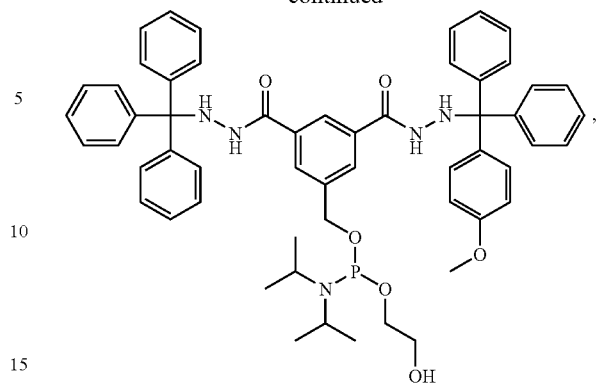

as well as the other multiple protected hydrazide reagents described generally above. Oligos modified with these reagents are readily purified utilizing standard HPLC processes.

Figure 8A:
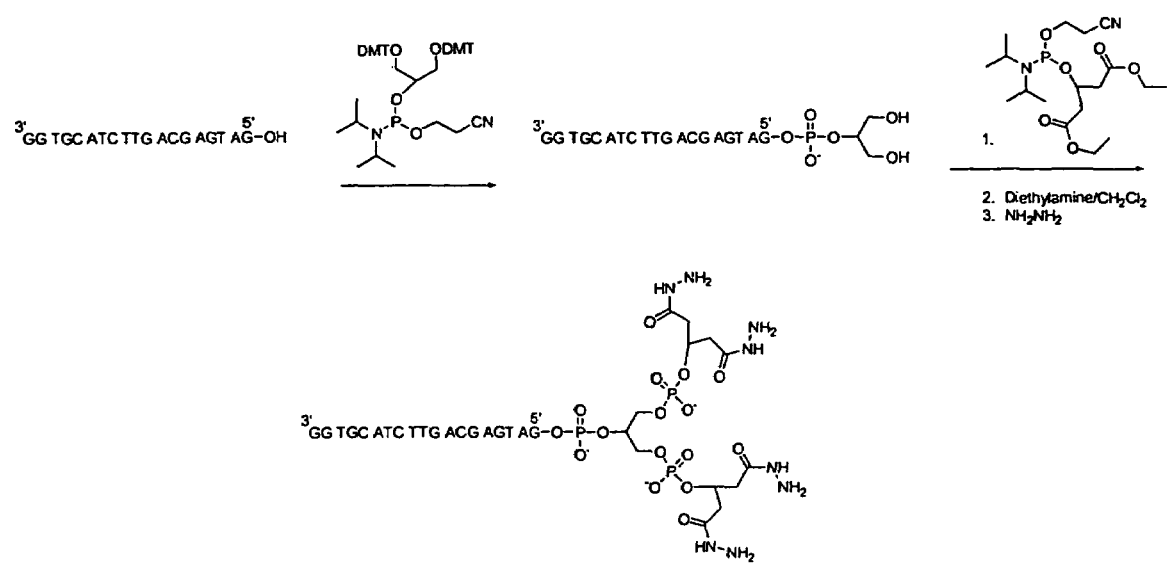
FIGS. 8A–D show chemical syntheses to produce structures having multiple attachment moieties. In (A) a branched phosphoramidite is added to an oligo which is further modified with a bifunctional phosphoramidite followed by deprotection with diethylamine/CH2Cl2 and hydrazine to generate a attachment moiety having four hydrazide groups for binding a substrate. In (B) a reaction scheme similar to (A) is provided resulting in six hydrazide attachment moieties. In (C) the sequential use of two different branched phosphoramidites results in 16 hydrazide attachment moieties per macromolecule. In (D) a branched phosphoramidite is used in two steps to form a dendrimeric structure followed by a phosphoramidite and hydrazine treatment to result in 4 hydrazide attachment moieties per macromolecule.

1.3 Combined Approach:

A third approach for the synthesis of macromolecules with multiple reactive groups is the combination of the coupling of branching amidites and amidites with multiple reactive sites, as described above (FIGS. 8A–C).

1.4 Non-Terminal Attachment Moiety Phosphoramidites

Alternatively, multiple attachment moieties may be added to a macromolecule or oligo in a linear fashion by utilizing reagents which comprise both one or more protected or precursor attachment moieties as well as a protected alcohol moiety for the addition of further reactive phosphate reagents. For instance, modifying reagent building blocks containing in addition to the a protected hydrazide or hydrazide-precursor ester, a protected functional group (such as an dimethoxytrityl protected hydroxyl group), enable the continuation of the biomolecule synthesis after the coupling of the modifying building block. An exemplary phosphoramidite reagent useful in such methods is as well as the other hydrazide precursor ester reagents described generally above.

Although these reagents are very useful for adding multiple hydrazide precursor moieties to a macromolecule or oligo in a single synthesis step, hydrazine deprotection is not a standard procedure in oligo synthesis. Also, the in situ generation of hydrazides yields oligos having deprotected hydrazides. These are somewhat difficult to purify by the standard procedures used in oligo synthesis, which usually take advantage of the shift in retention time in reversed phase HPLC caused by non-polar protecting groups such as trityl, monomethoxytrityl, dimethoxytrityl, etc. Thus, reagent building blocks which can add multiple pre-formed hydrazides which are protected with suitable protecting groups are advantageous for use with standard synthesis procedures.

Phosphoramidite reagents useful for adding multiple protected hydrazides include

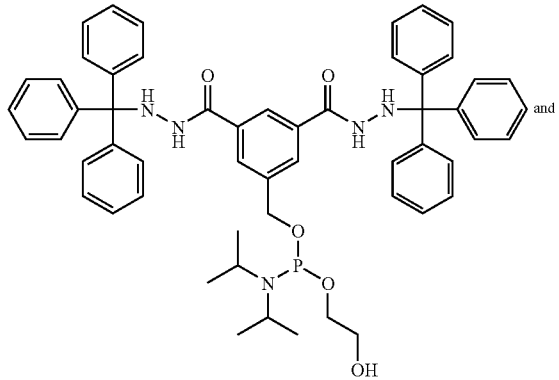

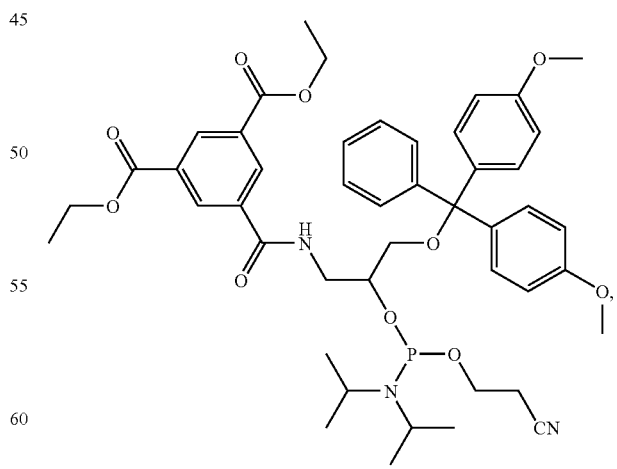

as well as the other protected alcohol reagents described generally above. This building block can be coupled consecutively to produce macromolecules with 2n hydrazides when coupled n times during the synthesis process. Further this type of building block reagent combines the approach of having a macromolecule or oligo with a non-polar protecting group for easy HPLC purification of the product with the approach of in situ generation of reactive hydrazide moieties by deprotecting the biomolecule with hydrazine after purification.

In addition to generating linear multi-hydrazide modifications, this type of reagent also allows the continuation of oligo synthesis. Thus, one may produce a macromolecule with two oligos on either side of a multi-hydrazide site for immobilization of the oligos to a substrate by additional rounds of standard oligo synthesis.

2.0 Hydrazides as Preferred Functional Groups for Use as Attachment Moieties

In particularly preferred embodiments, macromolecules are provided having one or more hydrazide moieties for attachment to a substrate surface through a covalent bond. These macromolecules, including oligos, may be coupled to a substrate or to other molecules using functional groups which react with hydrazides, such as NHS and Sulfo-NHS esters, and other moieties. As depicted in FIG. 18, a wide variety of reactions are available for hydrazide coupling.

In the present invention, the described hydrazide attachments provide a novel means whereby macromolecule attachment to a substrate may be carried out. The hydrazide coupling chemistry described provides resistance to dissociation of the tethered macromolecules from the substrate, which may be caused by the decomposition of the conjugate bond by extreme local environmental conditions associated with electronic addressing of an electronic microchip. Thus, the hydrazide chemistry and multiple attachment scheme of the present invention fulfills requirements for survivability in the environment of an electronic system, including a need for water solubility of the macromolecule, stability to aqueous conditions of the macromolecule and its coupling pair on the immobilizing substrate, and functionality to a pH of approximately pH 4.

2.1 Aliphatic and Aromatic Hydrazides

It should be noted that aliphatic and aromatic hydrazides have different reactivities regarding to the reactions for immobilization and conjugations. Thus, reagents for the addition of aromatic hydrazides as well as aliphatic are provided in the present invention, and may be advantageously used to increase the immobilized/conjugated macromolecule yield.

2.2 Methods for Hydrazide Coupling to Substrates

The methods by which hydrazide attachment moieties were added and utilized in the present invention are illustrated in the following examples. These examples show site specific covalent attachment of a macromolecule comprising an oligo in which attachment is accomplished by electronic concentration of a hydrazide-modified oligo onto an N-hydroxysuccinimidyl (NHS) modified polyacrylamide permeation layer above an electronically addressable microarray, or by physical deposition. The hydrazide moiety of the oligomer displaces the NHS ester forming a diacyl hydrazine linkage.

These examples therefore show 1.) Synthesis of novel protected hydrazide and hydrazide precursor phosphoramidites and successful incorporation of these amidites onto synthetic oligomers using standard synthetic procedures; 2.) Preparation of N-hydroxy- or N-hydroxysulfo-succinimidyl modified permeation layer; 3.) A two-layer permeation layer above the electronically addressable microarray in which the activated monomers are incorporated into only the top layer, 4) Coupling of hydrazide modifies oligos onto non-permeation layer substrates, such as glass slides, and 5) Several comparisons of various attachment moieties and conditions.

EXAMPLES

Unless otherwise indicated, all reactions were magnetically stirred. Reagents were obtained in analytical grade from Aldrich Chemical Company (Milwaukee Wis.) and solvents from Riedel. Column Chromatography is accomplished using silica gel 60 (Merck, 230–400 mesh). Melting points are uncorrected. IR Spectra are measured on a Perkin Elmer Paragon 1000 FT-IR equipped with a Graseby Specac 10500 ATR unit. $^1$H-NMR spectra were recorded at 500 MHz; $^{13}$C spectra at 125 MHz and $^{31}$P at 202 MHz with a Bruker DMX 500 spectrometer. $^1$H, $^{13}$C, $^{31}$P chemical shifts are reported in units of δ using TMS as internal standard, and coupling constants are reported in units of Hz. ESI Mass spectra are recorded on a Finnigan LCQ instrument in positive ionization mode. "Trace" refers to a concentration of 0.1 to 0.05%.

Example 1

Synthesis of Various Phosphoramidite Reagents for Adding Hydrazine Attachment Moieties to Macromolecules Experiment 1.1 Synthesis of N-Triphenylmethyl-6-hydroxycapronic acid hydrazide, compound 5, (FIG. 9A):

To a solution of 6.2 g (20 mmol) of tritylhydrazine hydrochloride in 200 ml of THF was added 2.22 g (22 mmol, 1.1 eq) of triethylamine. The solution was stirred at room temperature (rt) for 15 min, filtered, concentrated to afford 3, then treated with 2.29 g (20 mmol, 1 eq) of ε-caprolactone (4). The mixture is heated to 65° C. for 5 h the cooled to rt for 18 h. The precipitate was filtered and recrystallized from ethyl acetate to afford 3.55 g (45%) of a white powder 5: $^1$H-NMR 7.49–7.47 (m, 5H), 7.35–7.10 (m, 10H), 6.55 (d, J=7.52, 1H), 5.55 (d, J=7.25, 1H), 3.54 (t, J=6.45, 2H), 1.87 (t, J=7.25, 2H), 1.62 (bs, 1H), 1.57–1.34 (m, 4H), 1.27–1.11 (m, 2H).

Experiment 1.2 Synthesis of 6-[(2Cyanoethoxy)(diisopropylamino)phosphhanyloxy]-N'-tritylhexanohydrazide compund 1a, (FIG. 9A).

To a solution of 3.0 g (7.7 mmol) of N-triphenylmethyl-6-hydroxycapronic hydrazide (5) in 50 ml of dry dichloromethane at rt was slowly added 4.0 g (31 mmol, 4 eq) of N-ethyldiisopropyl amine and 2.01 g (8.5 mmol, 1.1 eq) of chloro(diisopropylamino)-β-cyanoethoxyphosphine (6) over 15 min. Upon complete addition, the reaction was stirred for 1 h, concentrated, and chromatographed (ethyl acetate/n-heptane 2/3 with trace triethylamine) to afford 3.19 g (70%) of 1a as a pale yellow foam.

$^1$H-NMR: 7.49–7.46 (m, 5H), 7.34–7.20 (m, 10H), 6.57 (d, J=7.2, 1H), 5.57 (d, J=7.5, 1H), 3.85–3.74 (m, 2H), 3.62–3.48 (m, 4H), 2.62–2.59 (m, 2H), 1.88–1.84 (m, 2H), 1.53–1.33 (m, 4H), 1.27–1.13 (m, 14H); $^{31}$P-NMR (CDCl$_3$): δ=147.97.

Figure 9B:
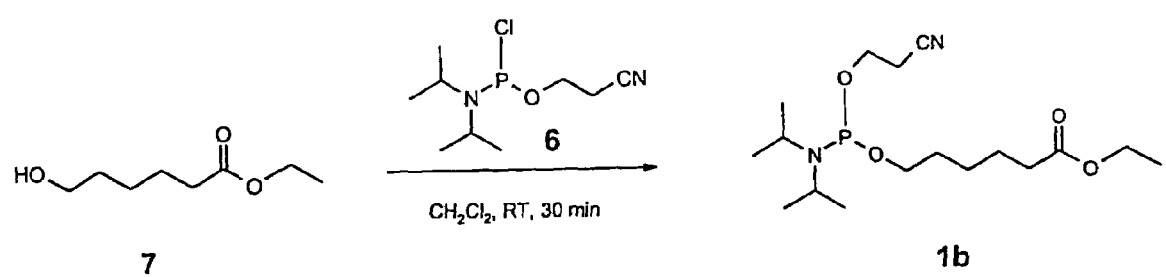
Figure 9C:
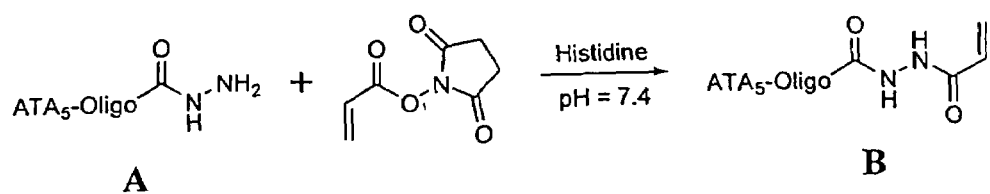

Experiment 1.3 Synthesis of Ethyl 6-[(2-cyanoethoxy) (diisopropylamino)phoshanyloxy]hexanoate compound 1b, (FIG. 9B, Scheme 2).

To a solution of 1.65 g (10 mmol) of ethyl 6-hydroxyhexanoate (7) in 30 ml of dichloromethane at rt are slowly added 5.17 g (40 mmol, 4 eq) of N-ethyldiisopropyl amine and 2.6 g (11 mmol, 1.1 eq) of 6 over 15 min. Upon complete addition, the reaction was further stirred for 15 min, concentrated, and chromatographed (ethyl acetate/n-heptane ¼ with trace triethylamine) to afford 2.47 g (69%) of 1b as clear oil: $^1$H-NMR 4.12 (q, J=7.25, 2H), 3.90–3.77 (m, 2H), 3.75–3.55 (m, 4H), 2.64 (t, J=6.44, 2H), 2.30 (t, J=7.25, 2H), 1.69–1.59 (m, 4H), 1.44–1.34 (m, 2H), 1.25 (t, J=7.25, 3H), 1.20–1.12 (m, 12H); $^{31}$P NMR 148.01.

Figure 6A:
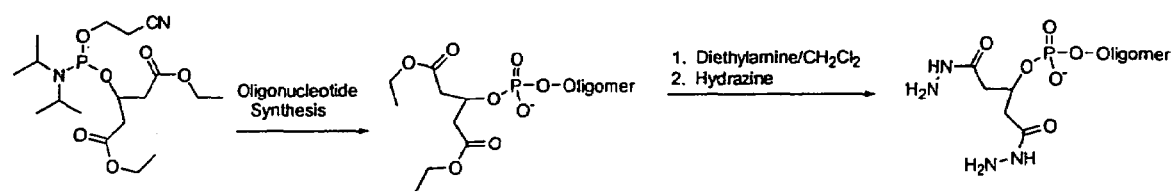
FIGS. 6A–C illustrate synthetic steps using phosphoramidites to produce macromolecules having multiple reactive sites. These moieties contain ester groups that are converted into hydrazides during the deprotection of the oligos with hydrazine.
Figure 6B:
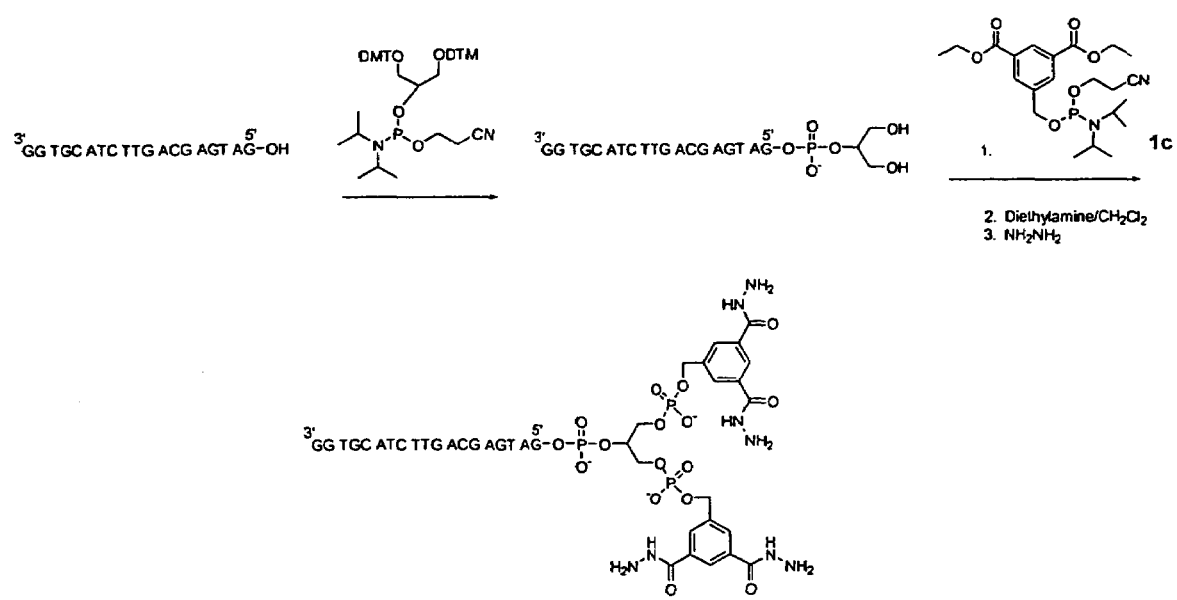
Figure 6C:
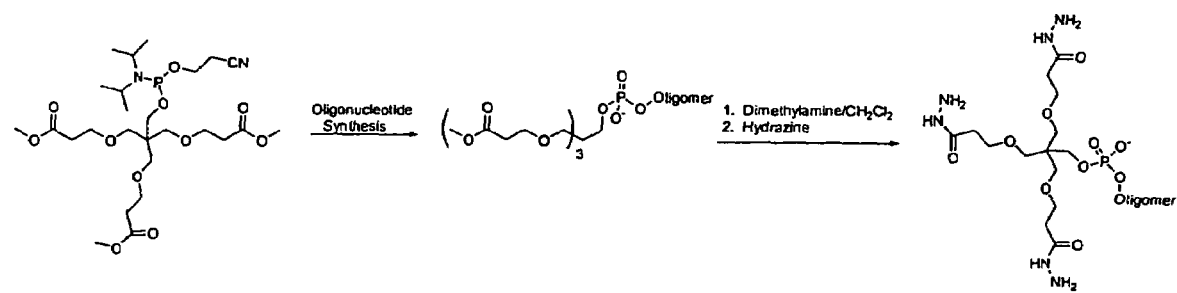
Figure 7:
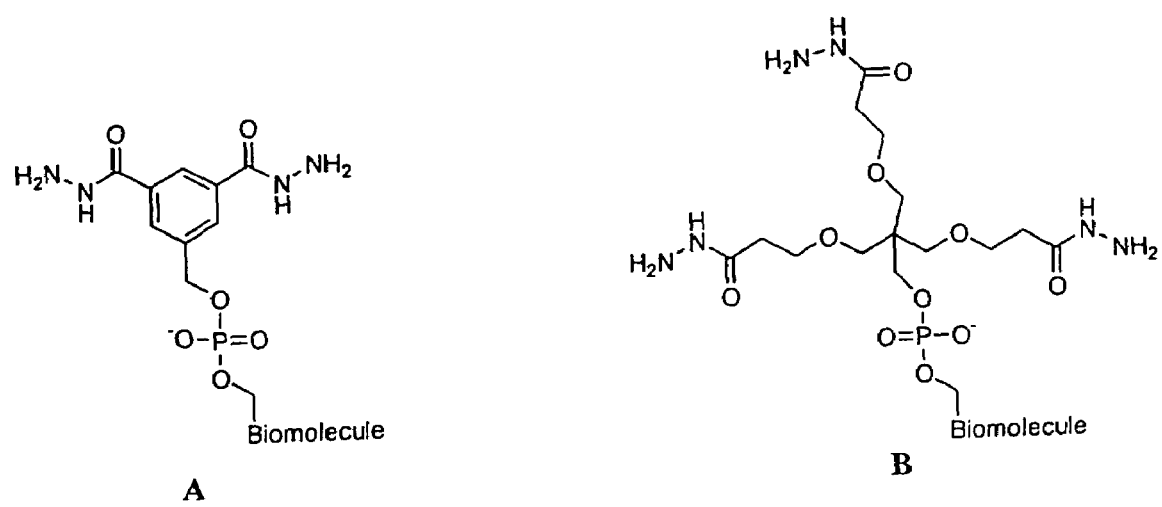
FIG. 7 shows chemical structures A and B comprising macromolecules having direct attachment of hydrazide moieties for use in immobilizing the macromolecule through a covalent bond to the substrate.

Experiment 1.4 Synthesis of: Diethyl 5-{[(2-cyanoethoxy)(diisopropylamino)phosphanyloxy]methyl}isophthalate compound 1c (FIG. 6B).

To a solution of 1.29 g (5 mmol) of diethyl 5-(hydroxymethyl)isophthalate in 20 ml of dry dichloromethane at rt are added 2.59 g (40 mmol, 4 eq) of N-ethyldiisopropyl amine and 1.3 g (11 mmol, 1.1 eq) of 2-cyanoethyl N,N-diisopropyl-chloro-phosphoramidite over 15 min. The mixture was concentrated, diluted with n-heptane/ethyl acetate\(3/2) and filtered. The filtrate was concentrated and chromatographed, eluted with n-heptane/ethyl acetate (4/1) and trace triethylamine to afford 1.6 g (70%) 1c as a colorless oil: $^1$H-NMR 8.59 (m, 1H), 8.21 (m, 2H), 4.87–4.75 (m, 2H), 4.41 (q, J=6.98 Hz, 4H), 3.95–3.80 (m, 2H), 3.74–3.61 (m, 2H), 2.66 (t, J (P, H)=6.45 Hz, 2H), 1.41 (t, J=6.00 Hz, 6H), 1.23–1.20 (m, 12H); $^{31}$P-NMR 149.94; $^{13}$C-NMR 165.8, 140.2, 132.1, 131.1, 129.7, 117.6, 64.7, 61.4, 58.6, 43.4, 24.7, 20.5, 14.4; HRMS 453.2156 ([M+H]$^+$ $C_{22}H_{34}N_2O_6P$ requires 453.21545).

Figure 8B:
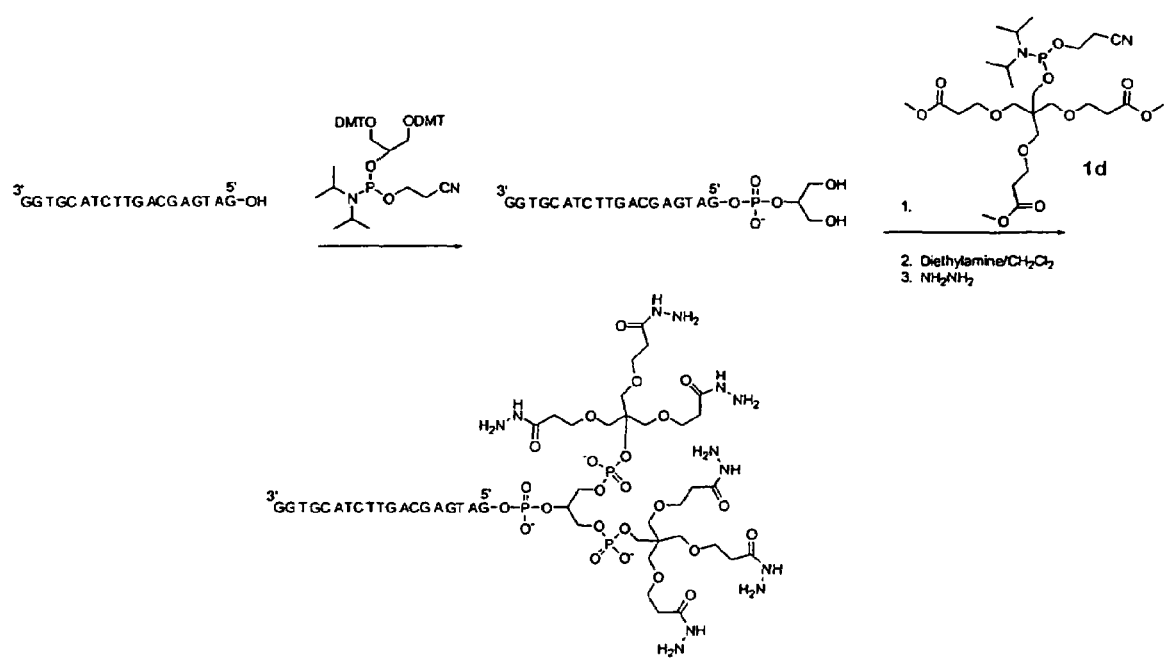
Figure 8C:
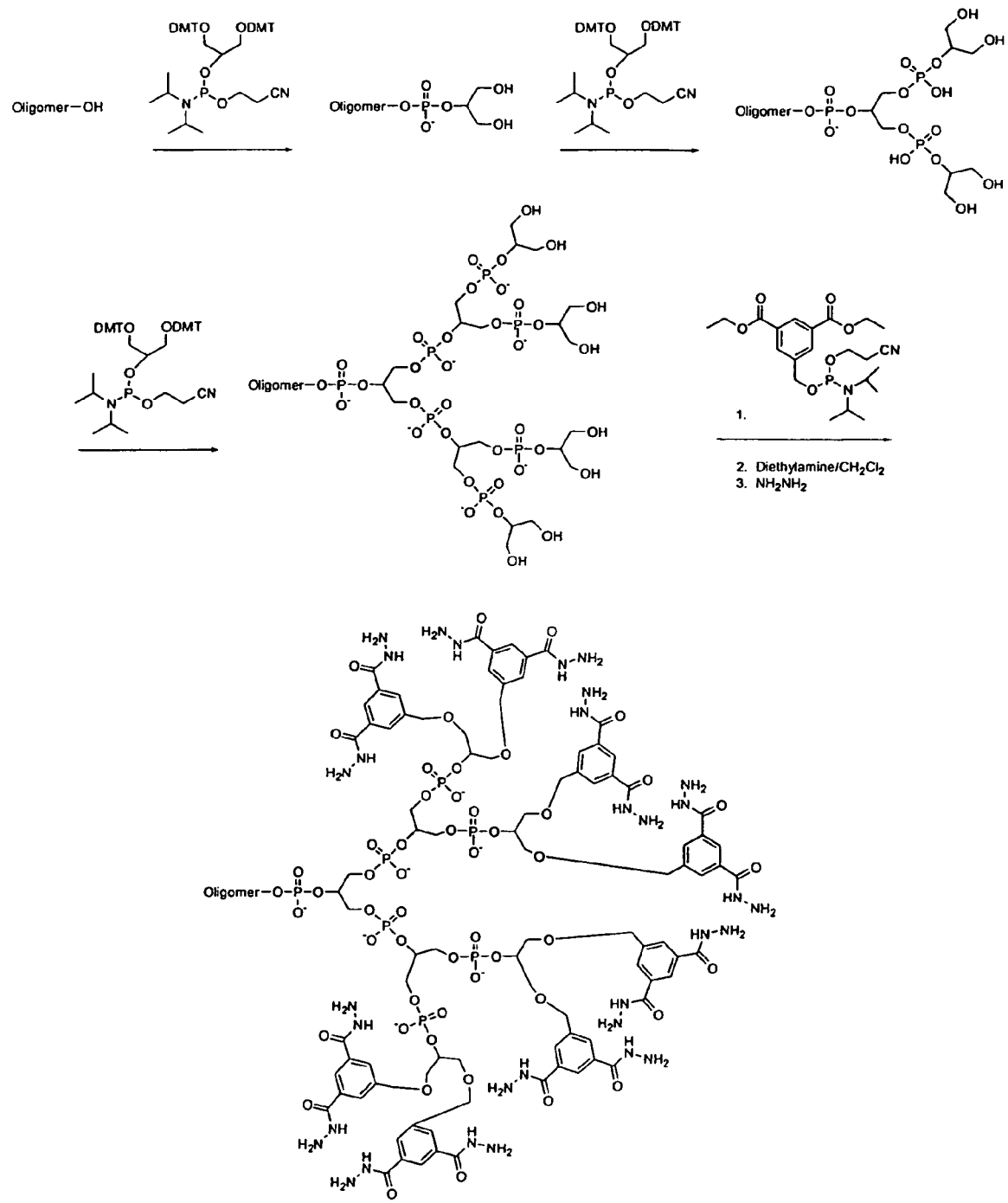
Figure 8D:
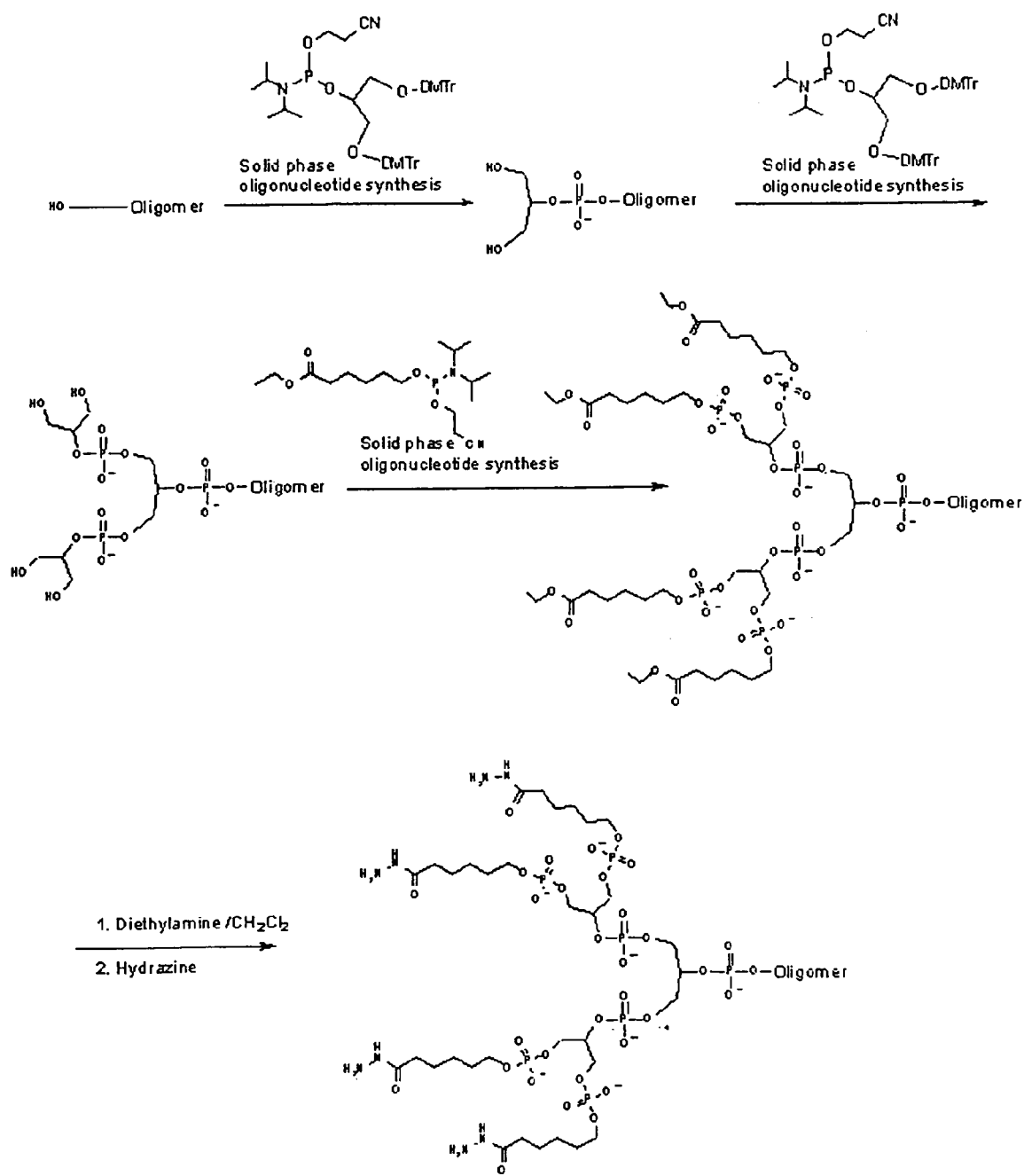

Experiment 1.5 Synthesis of Dimethyl 3,3'-(2-{[(2-cyanoethoxy)(diisopropylamino)phosphanyloxy]methyl}-2-{[2-(methoxycarbonyl)ethoxy]methyl}propane-1,3-diyl-bisoxy)dipropionate, compound 1d (FIG. 8B).

To a solution of 300 mg (0.760 mmol) of tris-2,2,2-{[(methoxycarbonyl)ethoxy]methyl}ethanol (Coutts, S.; Jones, D. S.; Livingston, D. A.; Yu, L. 1995, European patent application EP 0642798A2) in 2 ml dry dichloromethane are added two drops of a 0.4 M solution of 0.45 M 1H-tetrazole in dry acetonitrile and 274 mg (0.91 mmol; 1.1 eq) of 2-cyanoethyl N,N,N',N'-tetraisopropylphosphorodiamidite and stirred at rt until TLC shows complete consumption of the starting material (3 h). The mixture is concentrated and chromatographed (n-heptane/ethyl acetate 3/2 with trace triethylamine) to afford 240 mg (53%) of 1d as colorless oil: $^1$H-NMR: 3.88–3.71 (m, 2H), 3.68 (s, 9H), 3.65 (t, J=6.45 6H), 3.62–3.47 (m, 4H), 3.36 (s, 6H), 2.63 (t, J=7.25 Hz, 2H), 2.54 (t, J=6.45 Hz, 6H), 1.19–1.16 (m, 12H); $^{31}$P-NMR 148.6; HRMS: 595.2999 ([M+H]$^+$ $C_{26}H_{48}N_2O_{11}P$ requires 595.29957)

Figure 30A:
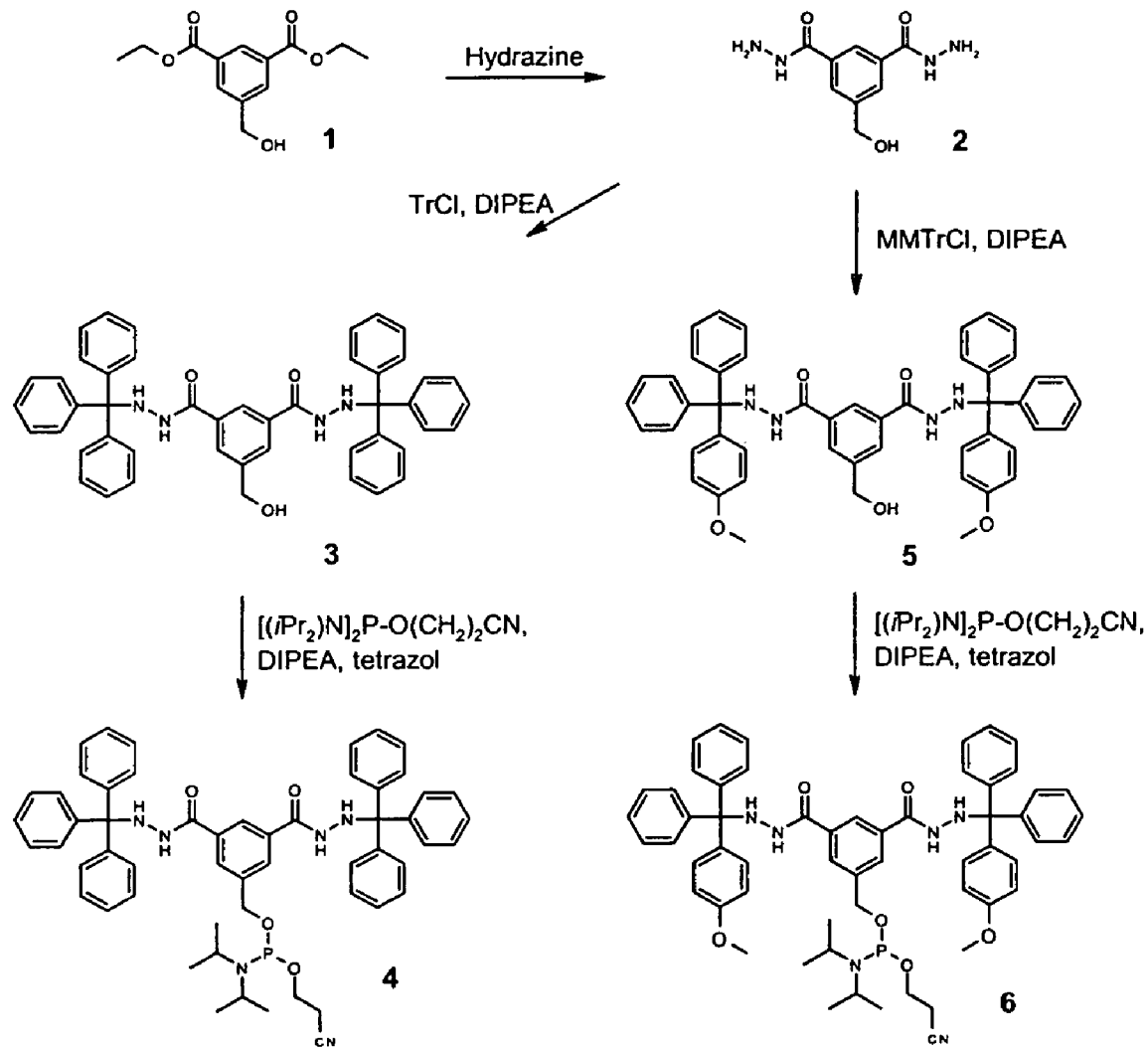
FIG. 30a shows a synthetic scheme for two phosphoramidite compounds comprising a pair of protected aromatic hydrazide moieties.

Experiment 1.6 Synthesis of 5-[(2-Cyanoethyl)(diisopropylamino)phosphanyloxymethyl]-isophthalic acid bis(N'-monomethoxytritylhydrazide) compound 6 (FIG. 30a).

Synthesis of 5-Hydroxymethylisophthalic Acid Dihydrazide 2

To a solution of 2.0 g (7.9 mmol) of diethyl 5-hydroxymethylisophtalate (1) in 30 ml of ethanol was added and 4.0 g (80 mmol) of hydrazine hydrate. After stirring 1.5 hours, an additional 4.0 g hydrazine hydrate was added and the mixture was allowed to stand overnight. The precipitate was filtered, washed twice with ethanol and dried under reduced pressure to yield 1.75 g (99%) of a white powdery 2: $^1$H-NMR (DMSO-d$_6$), 9.75 (bs, 2H), 8.11 (s, 1H), 7.89 (s, 2H), 5.36 (s, 1H), 4.57 (d, J=3.0 Hz), 4.51 (bs, 4H); $^{13}$C-NMR (DMSO-d$_6$) 165.6, 143.0, 133.4, 127.5, 124.1, 62.4.

5-Hydroxymethylisophthalic acid bis(N'-monomethoxytritylhydrazide) 5.

To a solution of 2.0 g (8.92 mmol) of dihydrazide 2 in 20 ml of DMF was slowly added 6.92 g (53.5 mmol, 6 eq.) of diisopropylethyl amine and 6.25 g (19.6 mmol, 2.2 eq.) of monomethoxytrityl chloride. The mixture was stirred 2.5 h, concentrated, diluted into 100 mL ethyl acetate, washed with 2×100 mL water and 2×100 mL saturated NaHCO$_3$. The organic phase was dried over sodium sulfate, filtered, concentrated and chromatographed eluded by gradient, (1/1 to 1/3 hexane/ethyl acetate with trace treithylamine) to afford 6.52 g (95%) of a white powdery 5: $^1$H-NMR: 7.50 (d, J=7.7 Hz, 8H), 7.39–7.36 (m, 6H), 7.26–7.23 (m, 10H), 7.20–7.17 (m, 4H), 6.79 (d, J=8.7 Hz, 4H), 5.79 (d, J=7.7 Hz, 2H), 4.40 (s, 2H), 3.74 (s, 6H)

5-[(2-Cyanoethyl)(diisopropylamino)phosphanyloxymethyl]-isophthalic acid bis(N'-monomethoxytritylhydrazide): 6.

To a solution of 1.0 g (1.3 mmol) of alcohol 5 in 15 mL dichloromethane, 1.5 mL of DMF and a few drops of diisopropylethylamine was added dropwise a solution containing 0.65 ml (3.9 mmol) diisopropylethylamine, 2.9 ml (1.1 mmol) of 0.45 M tetrazol and 0.51 g (1.69 mmol) of Bis-(diisopropylamino)-(2-cyanoethoxy)-phosphine in acetonitrile The mixture was stirred for 3.5 hours, 20 g de-acidified silica gel was added followed by solvent removal. The residue was chromatographed with gradient elution (1/1 to 1/2 hexane/ethyl acetate with trace triethylamine) to afford 0.59 g (47%) of white powdery 6: $^1$H-NMR 7.53–7.49 (m, 14H), 7.28–7.18 (m, 20H), 6.81 (d, J=8.7 Hz, 4H), 5.81 (d, J=8.1 Hz, 2H), 4.65–4.53 (m, 2H), 3.76 (m, 8H), 3.58 (m, 2H), 2.54 (t, J=6.4 Hz, 2H), 1.18 (d, J=6.7 Hz, 6H), 1.11 (d, J=6.7 Hz, 6H), $^{31}$P-NMR 149.6.

Experiment 1.7 Synthesis of 5-[(2-Cyanoethyl)(diisopropylamino)phosphanyloxymethyl]-isophthalic acid bis(N'-tritylhydrazide), compound 4 (FIG. 30a)

Synthesis of 5-Hydroxymethylisopthalic acid bis(N'-tritylhydrazide) 3.

To a solution of 2.0 g (8.92 mmol) of dihydrazide 2 in 20 ml of DMF was added 9.1 ml (53.5 mmol) of diisopropylamine and 5.6 g (19.6 mmol) of trityl chloride. The mixture was stirred for 2.5 hours, concentrated, and crystallized in 100 ml ethyl acetate. The product was filtered, washed with cold ethanol, dried under low vacuum at 40° C. for 18 h o yield 5.2 g (82%) of 3: $^1$H-NMR (DMSO-d$_6$,) 9.36 (d, J=7.4 Hz, 2H), 7.47–7.17 (m, 33H), 6.12 (d, J=7.4 Hz, 2H), 5.28 (t, J=5.7 Hz, 1H), 4.41 (d, J=5.7 Hz); $^{13}$C-NMR 165.4, 144.3, 142.5, 132.6, 128.5, 127.7, 126.8, 124.6, 73.4, 62.1.

Synthesis of 5-[(2-Cyanoethyl)(diisopropylamino)phosphanyloxymethyl]-isophthalic acid bis(N'-tritylhydrazide), 4.

To a solution of 1.3 ml (7.8 mmol) of diisopropylethylamine in 20 ml of dichloromethane was added 1.02 g (3.38 mmol) of bis-(diisopropylamino)-(2-cyanoethoxy)-phosphine followed by slow addition of a solution containing 1.84 g (2.6 mmol) of alcohol 3 and 5.8 ml (2.6 mmol) of 0.45 M tetrazol in acetonitrile/DMF (1/1) The mixture was stirred for 2 h, treated with 12 g of de-acidified silica gel, concentrated, and chromatographed with gradient elution (n-heptane, n-heptane/ethylacetate 2/3) to afford 0.36 g (16%) of a colorless oil, 4: $^1$H-NMR 7.53–7.46 (m, 14H), 7.28–7.16 (m, 26H), 5.85 (m, J=8.1 Hz, 2H), 4.62–4.53 (m, 2H), 3.79–3.73 (m, 2H), 3.61–3.56 (m, 2H), 2.52 (t, J=6.4 Hz), 1.17 (d, J=6.7 Hz, 6H), 1.11 (d, J=6.7 Hz); $^{31}$P-NMR 149.6

Figure 31A:
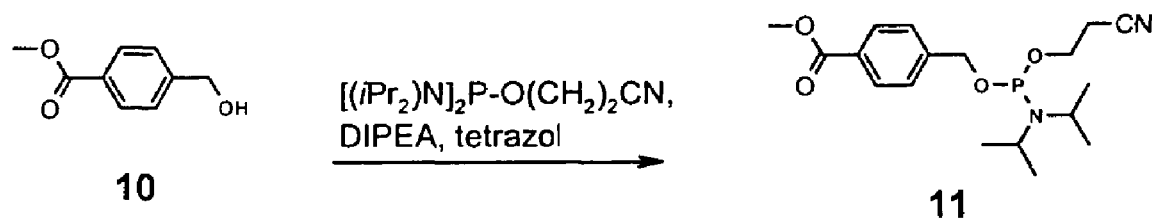
FIG. 31a shows a synthetic scheme for a phosphoramidite compound comprising a single aromatic hydrazide-precursor ester moiety.

Experiment 1.8 Synthesis of 4-[(2-Cyanoethyl)(diisopropylamino)phosphanyloxymethyl]-benzoic acid methyl ester, compound 11 (FIG. 31a)

To a solution of 3.73 g (22 mmol) of 4-hydroxymethylbenzoic acid methyl ester (10) and 0.16 g (2.2 mmol) of tetrazol in 50 ml of dichloromethane was added a solution of 7.4 g (24.6 mmol) of bis-(diisopropylamino)-(2-cyanoethoxy)-phosphine in 20 ml of dichloromethane over 20 minutes. Upon complete addition, the mixture was stirred for 1.5 hour at rt, concentrated, and chromatographed (heptane/ethyl acetate 4/1 with trace triethylamine) to afford 5.06 g (63%) of 11: 1H-NMR 8.1 (m, 2H), 7.5 (m, 2H), 4.8 (m, 2H), 3.9 (s, 3H), 3.8 (m, 2H), 3.7 (m, 2H), 1.1 (m, 12H), $^{31}$P-NMR 149.8

Figure 30B:
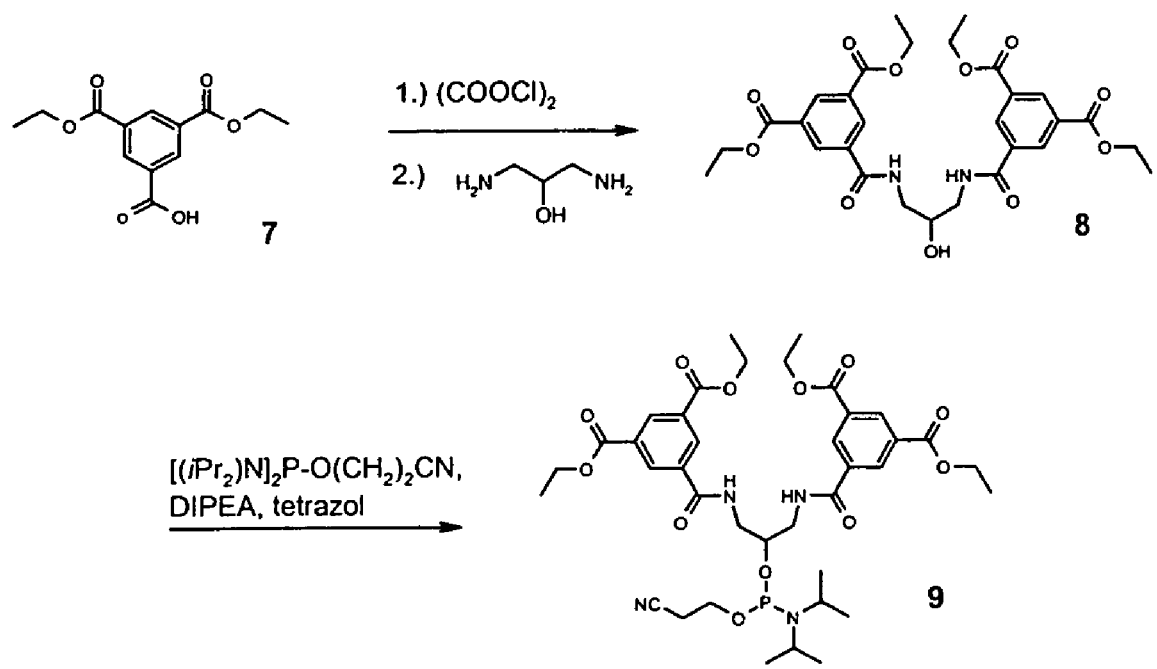
FIG. 30b shows a synthetic scheme for an amide-branched phosphoramidite compound comprising two pairs of aromatic hydrazide-precursor ester moieties.

Experiment 1.9 Synthesis of 1,3-Bis-[3',5'-bis(ethyloxy-carbonyl)phenylcarbonylamido]-2-[(2"-cyanoethyloxy)(diisopropylamino)-phosphanyloxy]-propane, compound 9 (FIG. 30b).

Synthesis of 1,3-Bis-[3',5'-bis(ethyloxycarbonyl)phenyl-carbonylamido]-propane-2-ol, 8.

To a solution of 9.0 g (34 mmol) of diethyl-1,3,5-benzene tricarboxylate (7) and two drops of DMF suspended in 100 ml toluene was slowly added 5.6 g (3.8 ml, 44 mmol) of oxalyl chloride. The mixture was stirred for 5.5 h, washed to neutrality with water, dried over sodium sulfate, filtered, concentrated and dried under reduced pressure to afford 9.6 g of crude acid chloride as a pale yellow oil.

The acid chloride was dissolved into 20 mL of chloroform and slowly added to a solution under argon at 0° C. of 1.43 g (15.7 mM) of 1,3-diamino-2-propanol and 6.6 ml (47.7 mmol) of triethylamine in 20 ml of chloroform and 5 ml of DMF. Upon complete addition, the mixture was warmed to rt, stirred 2.5 h, washed 2×50 mL dried over sodium sulfate, filtered and concentrated. The residue was mixed with 40 g of silica gel, evaporated to dryness and chromatographed with gradient elution (n-heptane/ethyl acetate 1/1 to ethyl acetate) to afford 4.2 g (37%) of white powdery 8: $^1$H-NMR 8.71 (t, J=1.6 Hz, 2H), 8.64 (d, J=1.6 Hz, 4H), 7.78 (m, 2H), 4.58 (m, 1H); 4.39 (q, J=7.0 Hz, 8H), 4.18 (m, 1H); 3.76–3.65 (m, 4H); 1.40 (t, J=7.0 Hz, 12H)

Synthesis of 1,3-Bis-[3',5'-bis(ethyloxycarbonyl)phenyl-carbonylamido]-2-[(2"-cyanoethyloxy)(diisopropylamino)-phosphanyloxy]-propane, compound 9

To a solution of 15.2 ml (6.82 mmol) of 0.45 M tetrazol in acetonitrile was added a solution of 2.65 g (3.57 ml, 20.5 mmol) of diisopropylethylamine and 2.67 g (8.87 mmol) Bis(diisopropylamino)-(2-cyanoethyloxy)phosphan in 5 ml of acetonitrile. The mixture was stirred for 15 minutes then added to a suspension of 4.0 g (6.28 mmol) alcohol 8 in 30 ml of dichloromethane and 5 ml of DMF. The mixture was stirred for 3 h, treated with 11 g of silica gel, concentrated and chromatographed with gradient elution (n-heptane/ethyl acetate 4/1 to 2/3) to yield 3.17 g (59%) of 9 as a pale yellow foam: $^1$H-NMR: 8.81 (m, 2H), 8.74 (d, J=1.6 Hz, 2H), 8.73 (d, J=1.6 Hz, 2H), 7.58 (m, 2H), 4.43 (q, 8.74 (q, J=7.0 Hz, 8H), 4.23 (m, 1H), 3.99 (m, 3H), 3.89 (m, 1H), 3.66 (m, 2H), 3.51 (m, 1H), 3.33 (m, 1H), 2.69 (m, 2H), 1.34 (t, J=7.0 Hz, 12H), 1.24 (d, J=6.7 Hz, 6H), 1.21 (d, J=6.7 Hz, 6H); $^{31}$P-NMR 151.0.

Figure 31B:
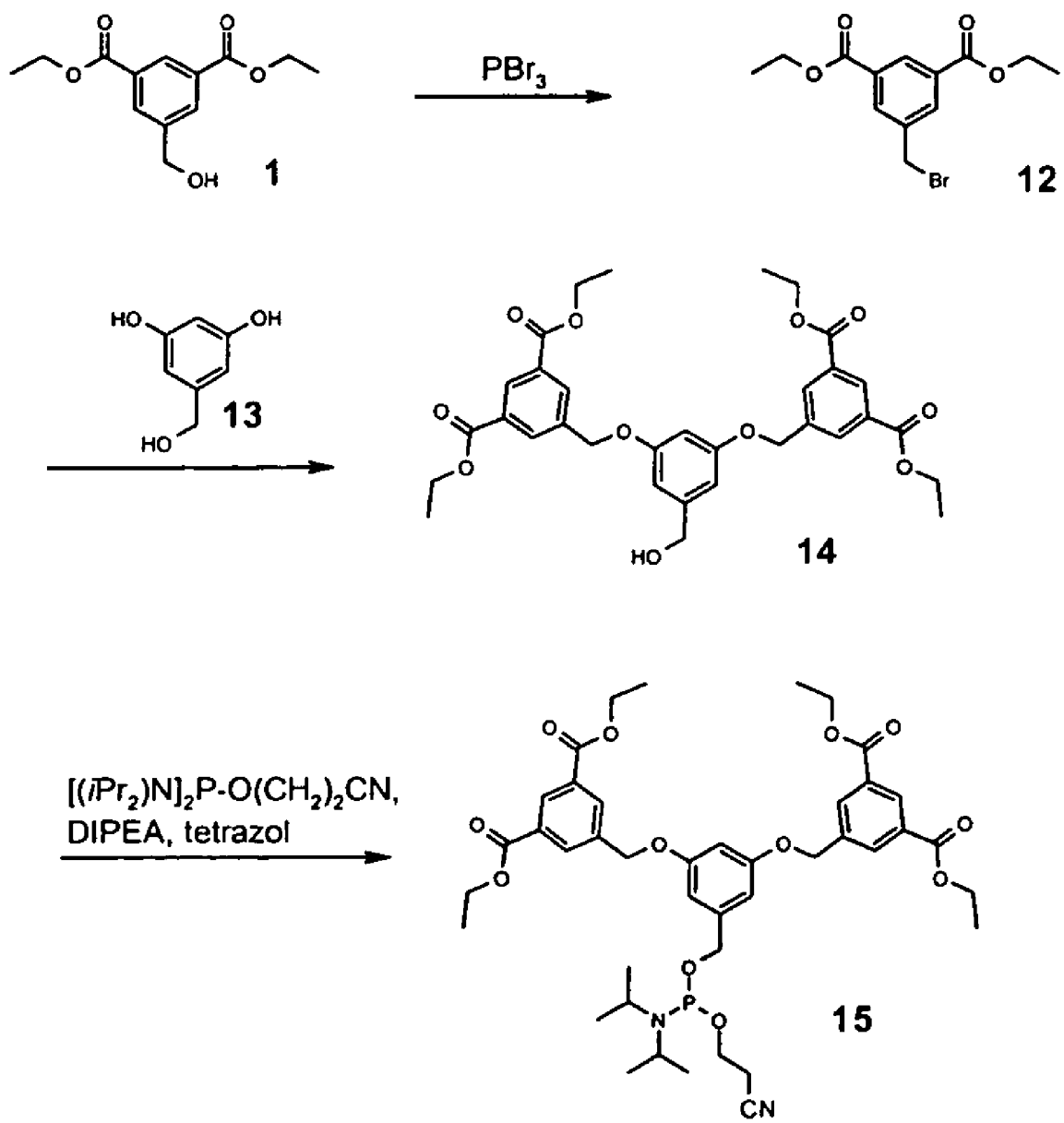
FIG. 31b shows a synthetic scheme for an ether-branched phosphoramidite compound comprising two pairs of protected aromatic hydrazide moieties.
Figure 31C:
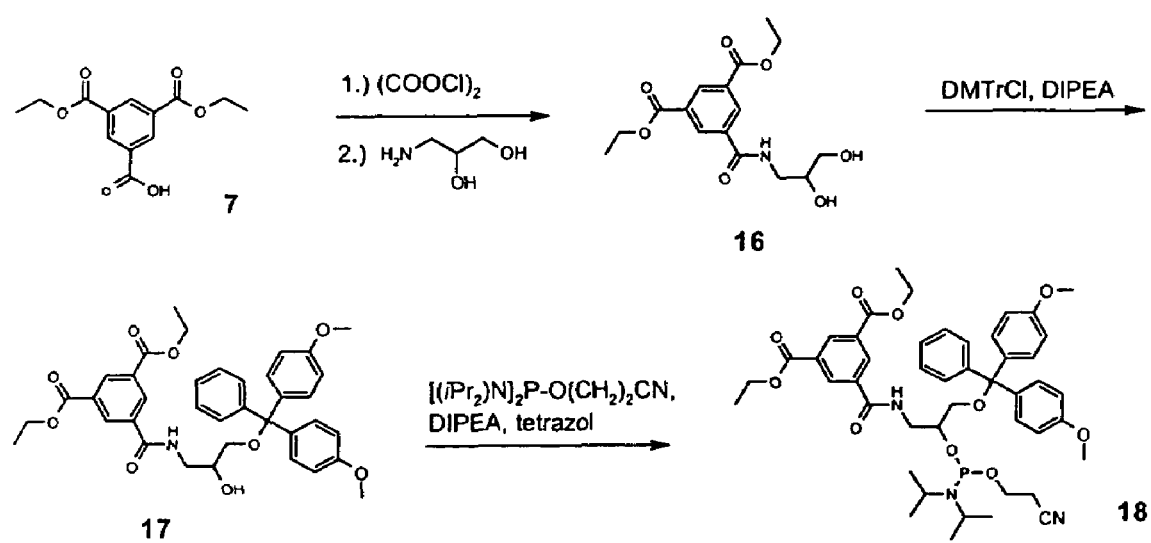
FIG. 31c shows a synthetic scheme for a phosphoramidite compound comprising a pair of aromatic hydrazide-precursor ester moieties and a protected alcohol moiety which may be utilized for further solid phase synthesis by standard phosphoramidite chemistry techniques.
Figure 31D:
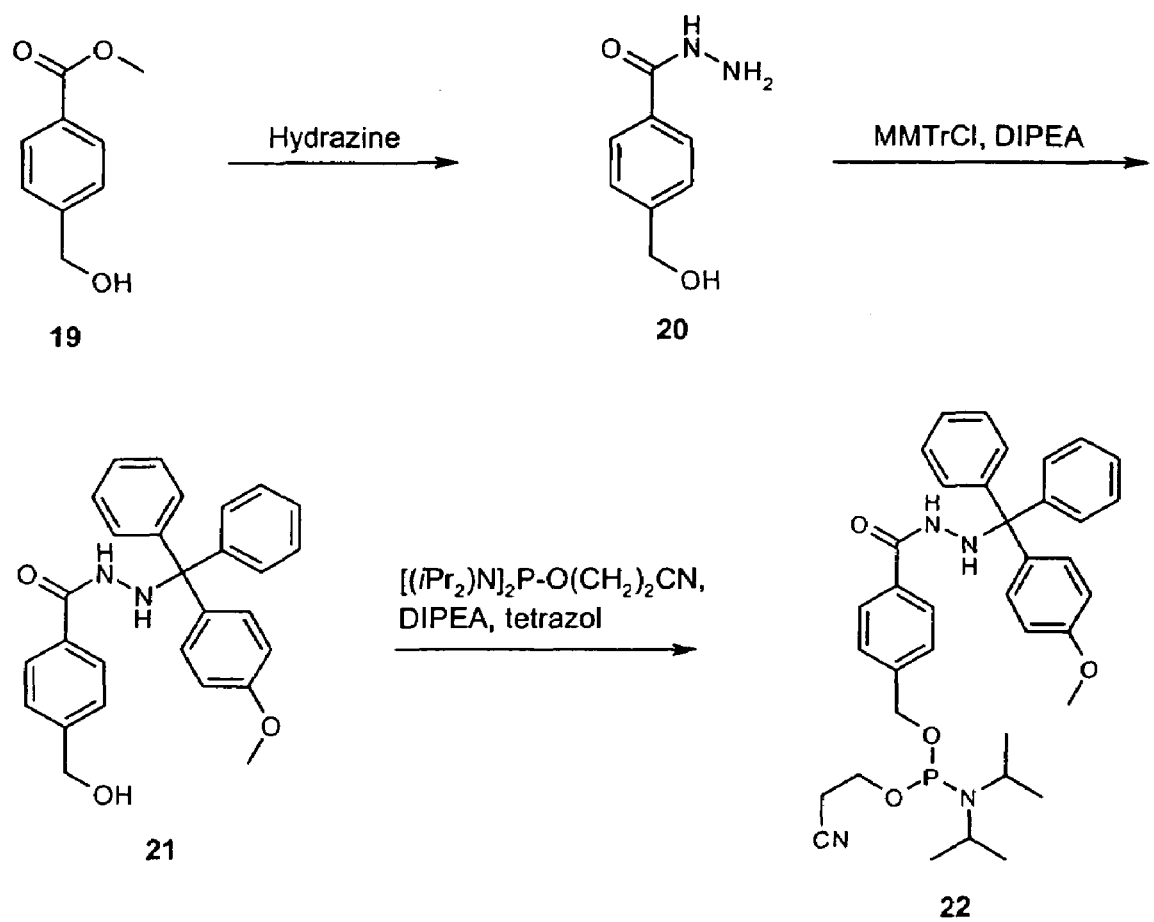
FIG. 31d shows a synthetic scheme for a phosphoramidite compound comprising a single aromatic protected hydrazide moiety.

Experiment 1.10 Synthesis of 4-[(2-Cyanoethyl)(diisopropylamino)phosphanyloxymethyl]-benzoic acid N'-monomethoxytritylhydrazide, compound 22 (FIG. 31d).

Synthesis of 4-Hydroxymethylbenzoic Acid Hydrazide, 20.

To a solution of 1.66 g (10.0 mmol) of methyl 4-hydroxymethylbenzoate (19) in 20 ml of ethanol was added 3.0 g (60 mmol) of hydrazine hydrate. The mixture was stirred for 2 h, an additional 3.0 g hydrazine hydrate was added and the mixture was allowed to stand overnight. The precipitate was filtered, washed twice with ethanol and dried in vacuo to yield 20 as a white powder. (Literature references for compound: Yaroshenko, V. V.; Grekov, A. P.; Tkach, V. P.; Yakovenko, A. G. Inst. Khim. Vysokomol. Soedin. *Sint. Fiz.-Khim. Polim.* 1975, 17 97; and Galiano, R.; Joaquin, A.; Soria, A. (Instituto de Investigacion y Desarrollo Quimico Biologico, S. A., Spain). Span. (1993), 24 pp. CODEN: SPXXAD ES 2039161 A1 19930816)

4-Hydroxymethylbenzoic acid N'-monomethoxytritylhydrazide, 21.

To a solution of 1.40 g (8.4 mmol) of hydrazide 20 in 20 ml of DMF was slowly added 4.95 g (38.4 mmol, 6 eq.) of diisopropylethyl amine and 5.58 g (18.5 mmol, 2.2 eq.) of monomethoxytriphenylmethyl chloride. The mixture was stirred for 2.5 h, concentrated, diluted with 100 ml of ethyl acetate, washed 2×100 mL of water, and 100 mL of saturated sodium bicarbonate. The organic layer was dried over sodium sulfate, filtered and chromatographed with gradient elution (hexane/ethyl acetate 1/1 to 1/3 with trace triethylamine) to afford white powdery 21.

4-[(2-Cyanoethyl)(diisopropylamino)phosphanyloxymethyl]-benzoic acid N'-monomethoxytritylhydrazide 22.

To a solution of 0.57 g (1.3 mmol) of alcohol 21 in a mixture of 10 ml of dichloromethane, 1.0 ml of DMF and trace diisopropylethylamine was slowly added a solution of 0.65 ml (3.9 mmol) of diisopropylethylamine in 3 ml of acetonitrile that had been treated with 3.0 ml (1.3 mmol) of 0.45 M of tetrazol and 0.55 g (1.66 mmol) of Bis-(diisopropylamino)-(2-cyanoethoxy)-phosphine in 5 mL of acetonitrile. The mixture was stirred for 3 h, 15 g de-acidified silica gel was added and the slurry was concentrated. The residue was chromatographed with gradient elution (hexane/ethyl acetate 1/1 to 1/2 with trace triethylamine) to afford 22 as a colorless powder.

Experiment 1.11 Synthesis of 1,3-Bis-[3',5'-bis(ethyloxycarbonyl)-benzyloxy]-5-[(2'-Cyanoethyl)(diisopropylamino)phosphanyloxymethyl]-benzene, compound 15 (FIG. 31b).

To a solution of 0.52 g (0.85 mmol) of alcohol 14 (literature prep: *J. Am. Chem. Soc.* 1996, 118, 8847) and 0.33 g (2.55 mmol) of diisopropylethylamine in in 5 ml of dichloromethane was added dropwise 0.23 g (0.93 mmol) of 2-cyanoethyl-N,N-diisopropyl-chloro-phosphoramidite The mixture was stirred at rt for 1 h and immediately chromatographed with gradient elution (heptane to heptane/ethylacetate 1/1) to afford 0.51 g (74%) of 15 as a pale yellow oil: $^1$H-NMR: 8.64 (m, 2H), 8.30 (m, 2H), 6.66 (m, 2H), 6.57 (m, 1H), 5.10 (m, 4H), 4.53–4.65 (m, 2H), 4.44 (m, 8H), 3.69–3.81 (m, 2H), 3.50–3.61 (m, 1H), 2.49 (m, 2H), 1.40 (m, 12H), 1.18 (d, J=6.7 Hz, 6H), 1.11 (d, J=6.7 Hz, 6H), $^{31}$P-NMR 147.8.

Example 2

Synthesis of Oligos Using Protected Hydrazide Phosphoramidites

General Synthesis of Oligos with Trityl/MMT/DMT Protected Hydrazide Amidites (e.g. Compounds 1a, 4, 6, 22):

Oligos (e.g., DNA, RNA, PNA, etc.) are synthesized using solid phase phosphoramidite chemistry on an automated oligo synthesizer. The phosphoramidite with the protected hydrazide is applied as 0.1M solution in acetonitrile and coupled at the desired location in the sequence using standard activated reagents and coupling times.

The CPG bound oligo (1 mmol) is placed in a 1.5 ml test tube and treated with 2.0 ml conc. NH$_4$OH. After 2 h at 55° C. the ammonia solution is removed and evaporated to dryness under reduced pressure. The residue is dissolved in 1 ml water and filtered through a 0.45 μm syringe filter. The trityl protected hydrazide oligo is purified by reverse phase HPLC, as described for the experiments. The fractions containing the trityl-on product were pooled and evaporated to dryness.

For the removal of the trityl protecting group the oligo is treated with 80% acetic acid for 30 min at RT. The acid is removed in vacuo, and the residue is dissolved in water then extracted twice with ethyl acetate. The aqueous layer is dried again and re-dissolved. Analytical HPLC usually shows a single product (is some cases as double peak) which can be employed for further reactions without purification. Alternatively HPLC purification can be performed using the solvent system described above.

For convenience, synthesized oligomers will be referred to as their oligomer number, e.g., O1. As described below, "dp" indicates a deprotected hydrazide phosphoramidite.

Experiment 2.1 Synthesis of Oligo O9: Hydrazide-15mer: (dp1a-TTT TTT TTT TTT TTT-3')

The synthesis and deprotection was performed as described with amidite compound 1a. The trityl protected hydrazide oligo was purified by reverse phase HPLC using a Merck LiChrospher RP 18, 10 µM, column (analytical: 4×250 mm, flow=1.0 ml/min; preparative: 10×250, flow=3.0 mL/min) using 0.1 M triethylammonium acetate pH=7.0 (TEAA) as buffer A and 75% acetonitrile in buffer A as buffer B. A gradient of 0% B to 100% B in 100 min was used for analytical and preparative separations. The trityl ON product elutes at 42.2 min under the conditions described. Oligo 9 elutes at 25.6 min (double peak). LRMS (ESI): M calc.: 4709.15, obs.: 4709.5.

Experiment 2.2 Oligo 10: Hydrazide 19mer: (dp-1a-dGA TGA GCA GTT CTA CGT GG-3')

The synthesis and deprotection was performed as described with amidite compound 1a. HPLC was performed as in experiment 2.1. The trityl ON product elutes at 41.5 min under the conditions described. Oligo 10 elutes at 25.1 min (single peak). HRMS (ESI): M calc.: 6092, obs.: 6092.

Experiment 2.3 Generation of Oligo 31 (dp-1a-TTT TTT TTT TTT TTT-Cy3)

The synthesis of the oligo was performed as described above, using compound 1a. A CPG support loaded with Cy3 dye was used to label the fluorophore at the 3' end of the oligo. The CPG bound oligo was treated as outlined above. The trityl protected hydrazide oligo is purified by reverse phase HPLC using a Phenomex Luna Phenyl hexyl RP 18, 10 µm, column (analytical: 4×250 mm, flow=1.0 ml/min; preparative: 10×250, flow=3.0 mL/min) using 0.1 M triethylammonium acetate pH=7.0 (TEAA) as buffer A and 95% acetonitrile in buffer. Gradient was 20% B . . . 100% B in 80 minutes. The hydrazide oligo elutes at 16.88 min. LRMS (ESI): M calc.: 5217, obs.: 5214.

Experiment 2.4 Generation of Oligo 32 (dp-6-ACA ACA ATT TGA AGC TTC TGT AAT TTT G-CY3)

The synthesis of the oligo was performed as described above, using compound 6. A CPG support loaded with Cy3 dye was used to label the fluorophore at the 3' end of the oligo. The CPG bound oligo was treated as outlined above. The trityl protected hydrazide oligo is purified by reverse phase HPLC using a Phenomex Luna Phenyl hexyl RP 18, 10 µm, column (analytical: 4×250 mm, flow=1.0 ml/min; preparative: 10×250, flow=3.0 mL/min) using 0.1 M triethylammonium acetate pH=7.0 (TEAA) as buffer A and 95% acetonitrile in buffer. Gradient was 0% B . . . 100% B in 100 minutes. The hydrazide oligo elutes at 36.58 min. LRMS (ESI): M calc.: 5439, with trityl, obs.: 5837.

Example 3

Synthesis of Oligos Using Hydrazide Ester Precursor Phosphoramidites

Figure 17:
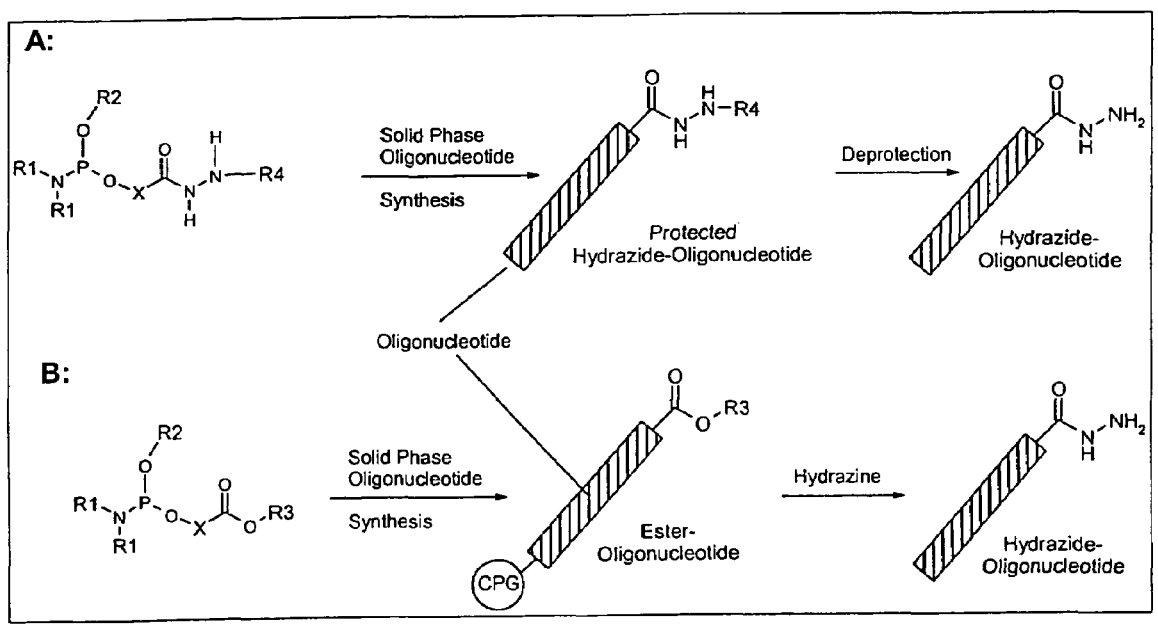
FIG. 17 shows the synthesis of a hydrazide modified oligo following two distinct protocols A and B. In A, a protected hydrazide phosphoramidite is used to modify the oligomer, which is then deprotected. In B, an ester phosphoramidite is used to modify the oligomer, which is then reacted with hydrazine.

General In Situ Generation of Hydrazide Functionality Synthesis of Oligos Using Phosphoramidites Containing Precursor Forms (e.g., Esters Such as Compound 1b FIG. 9B, Scheme 2; See also FIG. 17B):

Oligos are synthesized using solid phase phosphoramidite chemistry on an automated oligo synthesizer. The phosphoramidite with the precursor form of the hydrazide is applied as 0.1 M solution in acetonitrile and coupled at the desired location in the sequence using standard activating reagents and coupling times. The use of a phosphoramidite that contains a hydroxyl group labeled with an acid-labile protecting group as well as a hydrazide precursor allows the introduction of the hydrazide at any position of the oligo because the precursor form of the hydrazide is stabile to the conditions of the oligo synthesis while the reactive hydrazide is not formed until incubation with hydrazine.

The CPG bound oligo (1 mmol) is treated with a solution of 50 mg diethylamine in 3.5 mL dichloromethane. After incubation overnight (light exclusion) the supernatant is removed and the support bound oligo is washed several times with dichloromethane and dried in vacuo.

For the cleavage of the benzoyl and isobutyryl protecting groups the conversion of the ester at the 5'-end of the oligo to a hydrazide, and the cleavage of the oligo from the support (FIG. 17B), the CPG with the bound oligo is treated with 1 ml 24% hydrazine hydrate. After 18 h under constant agitation at 4° C. the reaction is complete. The isolation of the oligo from the hydrazine solution can be achieved by reversed phase extraction (e.g. Sep-Pak or HPLC).

A C18 Sep-Pak cartridge (0.5 g Waters, No. 20515) is activated by rinsing with 10 mL acetonitrile and then 10 mL 0.1 M triethylammonium bicarbonate buffer pH 7.0 (TEAB). The hydrazine solution is diluted with the 5-fold volume of TEAB and applied to the cartridge. After binding of the oligo to the Sep-Pak column the residual hydrazine is washed away with 10 mL TEAB. The oligo is then eluted from the column with TEAB/acetonitrile (1:2). Oligo containing fractions are pooled and evaporated to dryness. For the RP-HPLC characterization and purification of the product the same conditions as described in above2.1 or 2.3 can be applied.

As described below, "hz" indicates a hydrazine treated hydrazide precursor phosphoramidite.

Experiment 3.1 Generation of Oligo 11 (hz-1b-GA TGA GCA GTT CTA CGT GG-Cy3)

The synthesis of the oligo was performed as described previously, using compound 1b. A CPG support loaded with Cy3 dye was used to label the fluorophore at the 3' end of the oligo. The CPG bound oligo was treated as outlined above and the product was purified by RP-HPLC. The hydrazide oligo elutes at 31.8 min under the HPLC conditions described in Example 2.1. LRMS (ESI): M calc.: 6599.7, obs.: 6598±2.

For the following experiments, The CPG bound oligo (1 µmol) is treated with a solution of 50 mg diethylamine in 3.5 mL dichloromethane. After incubation overnight (in the dark exclusion) the supernatant is removed and the support bound oligo is washed several times with dichloromethane and dried in vacuo.

For the cleavage of the benzoyl and isobutyryl protecting groups the conversion of the Hydrazide precursors (e.g. esters) to an hydrazide, and the cleavage of the oligo from the support the CPG with the bound oligo, is treated with 1 ml 24% hydrazine hydrate. After 18 h under constant agitation at 4° C. the reaction is complete. The isolation of the oligo from the hydrazine solution can be achieved by reversed phase extraction (e.g. Sep-Pak or HPLC).

A C18 Sep-Pak cartridge (0.5 g Waters, No. 20515) is activated by rinsing with 10 mL acetonitrile and then 10 mL 0.1 M triethylammonium bicarbonate buffer pH 7.0 (TEAB). The hydrazine solution is diluted with the 5-fold volume of TEAB and applied to the cartridge. After binding of the oligo to the Sep-Pak column the residual hydrazine is washed away with 10 mL TEAB. The oligo is then eluted from the column with TEAB/acetonitrile (1:2). Oligo containing fractions are pooled and evaporated to dryness. For the RP-HPLC characterization and purification of the product the same conditions as described in example 2.3 were applied Experiment 3.2 Generation of Oligo 33 (hz-11-TTT TTT TTT TTT TTT-Cy3)

The synthesis of the oligo was performed as described above, using compound 11. A CPG support loaded with Cy3 dye was used to label the fluorophore at the 3' end of the oligo. The CPG bound oligo was treated as outlined above. RP-HPLC was carried out at a gradient of 10% B . . . 70% B in 60 minutes. The hydrazide oligo elutes at 26.60 min. LRMS (ESI): M calc.: 5236, obs.: 5234.

Experiment 3.3 Generation of Oligo 34 (hz-1c-TTT TTT TTT TTT TTT-Cy3)

The synthesis of the oligo was performed as described above, using compound 1c. A CPG support loaded with Cy3 dye was used to label the fluorophore at the 3' end of the oligo. The CPG bound oligo was treated as outlined above. RP-HPLC was carried out at a gradient of 25% B . . . 70% B in 45 minutes. The hydrazide oligo elutes at 16.87 min. LRMS (ESI): M calc.: 5295, obs.: 5293.

Experiment 3.4 Generation of Oligo 37 (hz-9-TTT TTT TTT TTT TTT-Cy3)

The synthesis of the oligo was performed as described above, using compound 9. A CPG support loaded with Cy3 dye was used to label the fluorophore at the 3' end of the oligo. The CPG bound oligo was treated as outlined above. RP-HPLC was carried out at a gradient of 25% B . . . 0.70% B in 45 minutes. The hydrazide oligo elutes at 11.15 min. LRMS (ESI): M calc.: 5601, obs.: 5599.

Experiment 3.5 Generation of Oligo 38 (hz-9-ACA ACA ATT TGA AGC TTC TGT AAT TTT G-Cy3)

The synthesis of the oligo was performed as described above, using compound 9. A CPG support loaded with Cy3 dye was used to label the fluorophore at the 3' end of the oligo. The CPG bound oligo was treated as outlined above. RP-HPLC was carried out at a gradient of 10% B . . . 70% B in 60 minutes. The hydrazide oligo elutes at 23.55 min. LRMS (ESI): M calc.: 9677, obs.: 9674.

Experiment 3.6 Generation of Oligo 39 (hz-15-TTT-TTT TTT TTT TTT TTT-Cy3)

The synthesis of the oligo was performed as described above, using compound 15. A CPG support loaded with Cy3 dye was used to label the fluorophore at the 3' end of the oligo. The CPG bound oligo was treated as outlined above. RP-HPLC was carried out at a gradient of 25% B . . . 70% B in 45 minutes. The hydrazide oligo elutes at 16.87 min. LRMS (ESI): M calc.: 5295, obs.: 5293.

Example 4

Preparation of Branching Structure Attachment Moieties for Nucleic Acid Oligos

General Synthesis of Branching Oligos.

For the introduction of multiple hydrazides into oligos, branching phosphoramidites, phosphoramidites having more than one ester group which are converted into hydrazides, as well as a combination of both approaches were used. Hydrazide precursor phosphoramidites are converted to hydrazides as described in Example 3. This flexible strategy allows the synthesis of oligos carrying defined numbers between one and up to several (~40) hydrazides. The experiments below in Example 5 describe the process for p-RNA oligos and are applicable to other oligos such as DNA.

Experiment 4.1 Generation of Oligo 35 (hz-(1c)$_2$SBA-TTT TTT TTT TTT TTT-Cy3)

The synthesis of the oligo was performed as described in the general procedure above, using compound 1c as the hydrazide precursor, and a synthetic branching amidite (SBA), compound 4 in table 2, was used as a branching building block. A CPG support loaded with Cy3 dye was used to label the fluorophore at the 3' end of the oligo. The CPG bound oligo was treated as outlined above. RP-HPLC was carried out at a gradient of 20% B . . . 100% B in 80 minutes. The hydrazide oligo elutes at 16.57 min. LRMS (ESI): M calc.: 5733, obs.: 5732.

Experiment 4.2 Generation of Oligo 36 (hz-(1c)$_2$SBA-ACA ACA ATT TGA AGC TTC TGT AAT TTT G-Cy3)

The synthesis of the oligo was performed as described in the general procedure above, using compound 1c as the hydrazide precursor, and a synthetic branching amidite (SBA), compound of entry 4 in table 2, was used as a branching building block. A CPG support loaded with Cy3 dye was used to label the fluorophore at the 3' end of the oligo. The CPG bound oligo was treated as outlined above. RP-HPLC was carried out at a gradient of 20% B . . . 100% B in 80 minutes. The hydrazide oligo elutes at 13.43 min. LRMS (ESI): M calc.: 9809, obs.: 9807.

Example 5

Production of pRNA Oligos with Branched and Unbranched Attachment Moieties

Experiment 5.1 Synthesis of p-RNA Oligos

The synthesis of p-RNA oligos is performed as described in: Miculka, C.; Windhab, N.; Brandstetter, T. Burdinski, G; PCT patent application No. WO 99/15540 (1999) with the following exceptions and modifications: Phosphoramidites of pentopyranosyl nucleosides are dried in vacuo over KOH and dissolved in dry acetonitrile to give a 0.1 M solution. This solution is dried over freshly activated molecular sieve (3 Å) for 3 h and then applied for solid phase oligo synthesis on a PE Biosystems Expedite 8905 DNA synthesizer. Other phosphoramidites are dissolved at 0.1 M in dry acetonitrile and used without further treatment. For p-RNA oligos carrying a Cy3 dye at the 2'-end a CPG support custom loaded with monomethoxytrityl protected Cy3 (CAS: 182873-80-9, AP-Biotech, Freiburg, Germany) a 0.1 M solution of anhydrous pyridinium hydrochloride in dry acetonitrile is used as activator. The detritylation time for pentopyranosyl nucleosides is increased to 10 minutes and the coupling time is increased to 25 minutes. All other reagents and solutions and procedures are according to the recommendation of the instrument manufacturer.

Experiment 5.2 Deprotection of p-RNA Oligos:

For the cleavage of the β-cyanoethyl protecting groups the oligo is treated with a 1.5% (w/v) solution of diethylamine in dichloromethane overnight at RT (light exclusion). The supernatant is removed and the support bound oligo is washed several times with dichloromethane and dried in vacuo.

For the cleavage of the benzoyl and isobutyryl protecting groups, the conversion of the esters at the 5'-end of the oligo to hydrazides, and the cleavage of the oligo from the support, the CPG with the bound oligo is treated with 1 ml 24% hydrazine hydrate. After 18 h under constant agitation at 4° C. the reaction is complete. The isolation of the oligo from the hydrazine solution can be achieved by reversed phase extraction (e.g. Sep-Pak or HPLC).

A C18 Sep-Pak cartridge (0.5 g Waters, No. 20515) is activated by rinsing with 10 mL acetonitrile and then 10 mL 0.1 M triethylammonium bicarbonate buffer pH 7.0 (TEAB). The hydrazine solution is diluted with the 5-fold volume of TEAB and applied to the cartridge. After binding of the oligo to the Sep-Pak column the residual hydrazine is washed away with 10 mL TEAB. The oligo is then eluted from the column with TEAB/acetonitrile (1:2). Oligo containing fractions are pooled and evaporated to dryness. The characterization and purification of the products is achieved by reverse phase HPLC using a Merck LiChrospher RP 18, 10 µM, column (analytical: 4×250 mm, flow=1.0 ml/min; preparative: 10×250, flow=3.0 mL/min) using 0.1 M triethylammonium acetate pH=7.0 (TEAA) as buffer A and 75% acetonitrile in buffer A as buffer B. A gradient of 0% B to 100% B in 100 min (HPLC method A) or 30 min (HPLC method B) is used for analytical and preparative separations.

Experiment 5.2.1 Oligo 12: Cy3 Labeled p-RNA Oligo with 1 Hydrazide: p-RNA Olio 4'-hz-1b-TAG GCA TT (Cy3)-2'

The synthesis and deprotection was performed as described with amidite compound 1b.

Experiment 5.2.2 Oligo 13: Cy3 Labeled p-RNA Oligo with 3 Hydrazides: p-RNA Oligo 4'-hz-1d-TAG GCA TT (Cy3)-2'

The synthesis and deprotection was performed as described with amidite compound 1d. The product elutes at 37.9 min (HPLC method A) under the conditions described. LRMS (ESI): M calc.: 3516.6, obs.: 3515.

Experiment 5.2.3 Oigo 14: Cy3 Labeled p-RNA Oligo with 4 Hydrazides: p-RNA Oligo 4'-hz-(1c)$_2$ (SBA) TAG GCA TT (Cy3)-2'

The synthesis and deprotection was performed as described with amidite compound 1c and with symmetric branching phosphoramidite (SBA; Clontech, No. 5252-2). The product elutes at 37.3 min (HPLC method A) under the conditions described. LRMS (MALDI): M calc.: 3784.7, obs.: 3784

Experiment 5.2.4 Oligo 15: Cy3 Labeled p-RNA Oligo with 8 Hydrazides: p-RNA Oligo 4'-hz-(1c)$_4$ (SBA)$_2$ (SBA) TAG GCA TT (Cy3)-2'

The synthesis and deprotection was performed as described with amidite compound 1c and with symmetric branching phosphoramidite (SBA; Clontech, No. 5252-2). The product elutes at 36.9 min (HPLC method A) under the conditions described. LRMS (MALDI): M calc.: 4661.1, obs.: 4464

Experiment 5.2.5 Oligo 16: Cy3 Labeled p-RNA Oligo with Spacer and 8 Hydrazides: p-RNA Oligo 4'-hz-(1c)$_4$ (SBA)$_2$ (SBA) (S18) TAG GCA TT (Cy3)-2'

The synthesis and deprotection was performed as described with amidite compound 1c and with symmetric branching phosphoramidite (SBA; Clontech, No. 5252-2) and Spacer 18 (S18, Glen research No. 10-1918-02). The product elutes at 38.7 min (HPLC method A) under the conditions described.

Experiment 5.2.6 Oligo 17: Cy3 Labeled p-RNA Oligo with 16 Hydrazides: p-RNA Oligo 4'-(1c)$_8$ (SBA)$_4$ (SBA)$_2$ (SBA) TAG GCA TT (Cy3)-2'

The synthesis and deprotection was performed as described with amidite compound 1c and with symmetric branching phosphoramidite (SBA; Clontech, No. 5252-2). The product elutes at 38.7 min (HPLC method A) under the conditions described.

Experiment 5.2.7 Oligo 18: p-RNA Oligo with 4 Hydrazides (Without Cy3 Dye): p-RNA Oligo 4'-(1c)$_2$ (SBA) TAG GCA TT-2'

The synthesis and deprotection was performed as described with amidite compound 1c. The product elutes at 12.75 min (HPLC method B) under the conditions described. LRMS (ESI): M calc.: 3275.1, obs.: 3275.4.

Experiment 5.3 Oligo 26: Preparation of a Monohydrazide pRNA Using a Protected Hydrazide Phosphoramidite: pRNA Oligo 4'-dp-6-AGA CGT AGA G-Cy3-2'

For the cleavage of the β-cyanoethyl protecting groups the oligo was treated with a 1.5% (w/v) solution of diethylamine in dichloromethane overnight at RT (light exclusion). The supernatant was removed and the support bound oligonucleotide was washed several times with dichloromethane and dried in vacuo.

For the cleavage of the benzoyl and isobutyryl protecting groups and the cleavage of the oligo from the support, the CPG with the bound oligo was treated with 1 ml 24% hydrazine hydrate. After 18 h under constant agitation at 4° C. the reaction was complete. The isolation of the oligo from the hydrazine solution was achieved by reversed phase extraction (e.g. Sep-Pak or HPLC).

A C18 Sep-Pak cartridge (0.5 g Waters, No. 20515) was activated by rinsing with 10 mL acetonitrile and then 10 mL 0.1 M triethylammonium bicarbonate buffer pH 7.0 (TEAB). The hydrazine solution was diluted with the 5-fold volume of TEAB and applied to the cartridge. After binding of the oligo to the Sep-Pak column the residual hydrazine was washed away with 10 mL TEAB. The oligo was then eluted from the column with TEAB/acetonitrile (1:2). Oligo containing fractions are pooled and evaporated to dryness. The characterization and purification of the products was achieved by reverse phase HPLC using a Phenomex Luna Phenyl Hexyl RP 18, 10 µM, column (analytical: 4×250 mm, flow=1.0 ml/min; preparative: 10×250, flow=3.0 mL/min) using 0.1 M triethylammonium acetate pH=7.0 (TEAA) as buffer A and 75% acetonitrile in buffer A as buffer B.

For the removal of the trityl protecting group the oligo was treated with 80% acetic acid for 30 min at RT. The acid was removed in vacuo, and the residue was dissolved in water then extracted twice with ethyl acetate. The aqueous layer was dried again and re-dissolved. Analytical HPLC usually shows a single product (is some cases as double peak) which can be employed for further reactions without purification. Using a gradient of 20% B . . . 100% B in 80 minutes, the product elutes at 16.83 min. LRMS (ESI): M calc.: 4055, obs.: 4053.

Example 6

Conversion of Hydrazide Oligos to Boronate Oligos

General Procedure for the Conversion of Hydrazide Oligos into Boronate Oligos 50 nmol hydrazide oligo are dissolved in 200 µL 10 mM ammonium acetate buffer pH 4.0 and 15 equivalents of 4-Formylphenlyboronic acid (Aldrich No. C43, 196-6; CAS: 87199-17-5) per hydrazide are added. For an oligo containing 4 hydrazides for example 30 µL of a 0.1 M solution of 4-Formylphenlyboronic acid in DMSO (3 µmol) are used. The mixture is incubated at RT for 1 h, 20 equivalents NaCNBH$_3$ per 4-Formylphenlyboronic acid are added and incubation is continued for one other hour at RT. For example for the oligo with 4 hydrazides 150 μL (150 μmol) of a 1 M solution of NaCNBH$_3$ in 10 mM ammonium acetate buffer pH 4.0 (6.3 mg dissolved in 1 mL) are necessary.

The removal of excess 4-Formylphenlyboronic acid and Sodium Cyanoborohydride are removed by means of HPLC, gel filtration (Pharmacia PD 10 columns), or solid phase extraction (Merck LiChrolute columns). For boronate modified oligos it is crucial to use an endcapped HPLC column. Typical conditions are 5 μm Phenomenex Luna Phenyl Hexyl columns (analytical: 4.6×250 mm, flow=1.0 ml/min; preparative: 10×250, flow=3.0 mL/min) using 0.1 M triethylammonium acetate pH=7.0 (TEAA) as buffer A and 75% acetonitrile in buffer A as buffer B. A gradient of 0% B to 100% B in 100 min (HPLC method A) or 30 min (HPLC method B) is used for analytical and preparative separations. Product containing fractions are pooled and evaporated to dryness.

Experiment 6.1 Oligo 19: p-RNA Oligo with 1 Boronate: p-RNA Oligo 4'-(PBA) TAG GCA TT (Cy3)-2'

The synthesis and deprotection was performed as described in the general protocol using oligo 12 as starting material.

Experiment 6.2 Oligo 20: p-RNA Oligo with 3 Boronates: p-RNA Oligo 4'-(PBA)$_3$ TAG GCA TT (Cy3)-2'

The synthesis and deprotection was performed as described in the general protocol using oligo 13 as starting material.

Experiment 6.3 Oligo 21: p-RNA Oligo with 4 Boronates: p-RNA Oligo 4'-(PBA)$_4$ (SBA) TAG GCA TT (Cy3)-2'

The synthesis and deprotection was performed as described in the general protocol using oligo 14 as starting material.

Experiment 6.4 Oligo 22: p-RNA Oligo with 8 Boronates: p-RNA Oligo 4'-(PBA)$_8$ (SBA)$_2$ (SBA) TAG GCA TT (Cy3)-2'

The synthesis and deprotection was performed as described in the general protocol using oligo 15 as starting material. The product elutes at 46.3 min (HPLC method A) under the conditions described.

Experiment 6.5 Oligo 23: p-RNA Oligo with Spacer 18 and 8 Boronates: p-RNA Oligo 4'-(PBA)$_8$ (SBA)$_2$ (SBA) TAG GCA TT (Cy3)-2'

The synthesis and deprotection was performed as described in the general protocol using oligo 16 as starting material.

Experiment 6.6 Oligo 24: p-RNA Oligo with 16 Boronates: p-RNA Oligo 4'-(PBA$_{16}$ (SBA)$_4$ (SBA)$_2$ (SBA) TAG GCA TT (Cy3)-2'

The synthesis and deprotection was performed as described in the general protocol using oligo 17 as starting material. The product elutes at 49.0 min (HPLC method A) under the conditions described.

Experiment 6.7 Oligo 25: p-RNA Oligo with 1 Boronate: p-RNA Oligo 4'(PBA)-TAG GCA TT (Cy3)-2'

The synthesis and deprotection was performed as described in the general protocol using oligo 18 as starting material.

Example 7

HPLC Analysis

Upon completion of the synthesis of hydrazide oligos, the first set of experiments examined the solution reaction kinetics of a hydrazide labeled oligo with an NHS or Sulfo-NHS ester. To a solution of 5 uL of 132 uM hydrazide ATA5 in 30 uL of 50 mM histidine was added 5 uL of 10 mM NHS acrylate. The solution was stirred at RT for a short period of time then injected into an HPLC system. The HPLC trace of the compounds in the solution indicated the quantities of hydrazide ATA5 and N'acrylo-ATA5 dihydrazide present in the reaction mixture for a given reaction time. The retention times of the starting ATA5 hydrazide and the modified ATA5 hydrazide were distinct and separable.

Figure 10:
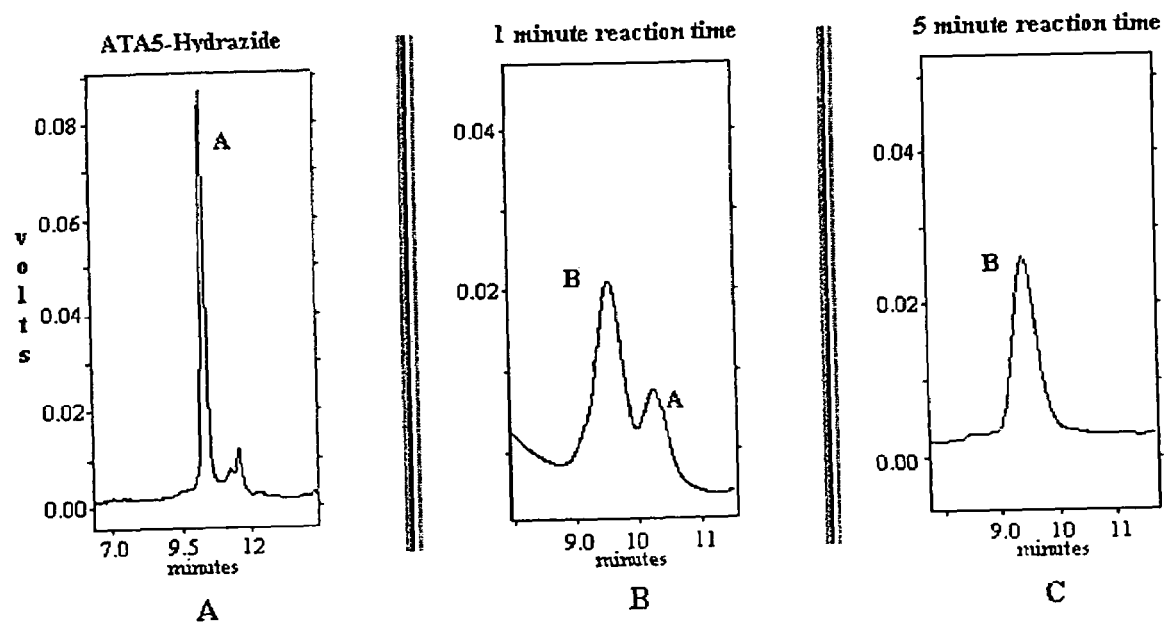
FIGS. 10A–C are graphs of three separate HPLC traces of the reaction mixture for coupling hydrazide-labeled oligo to an activated ester monomer such as that shown in Scheme 3 of FIG. 9.

FIGS. 10A–C show three separate traces of the reaction mixture. The first trace (A) was obtained from an unmodified ATA5 hydrazide (A), and the third trace (C) represents a completely modified ATA5 hydrazide (B) after a reaction time of 5 minutes with NHS acrylate. The middle trace (B) represents an incomplete modification captured 1 minute into the reaction. Given the approximate consumption of ATA5 hydrazide, a pseudo-first order reaction rate of 1200 $M^{-}s^{-1}$ is determined.

Figure 11:
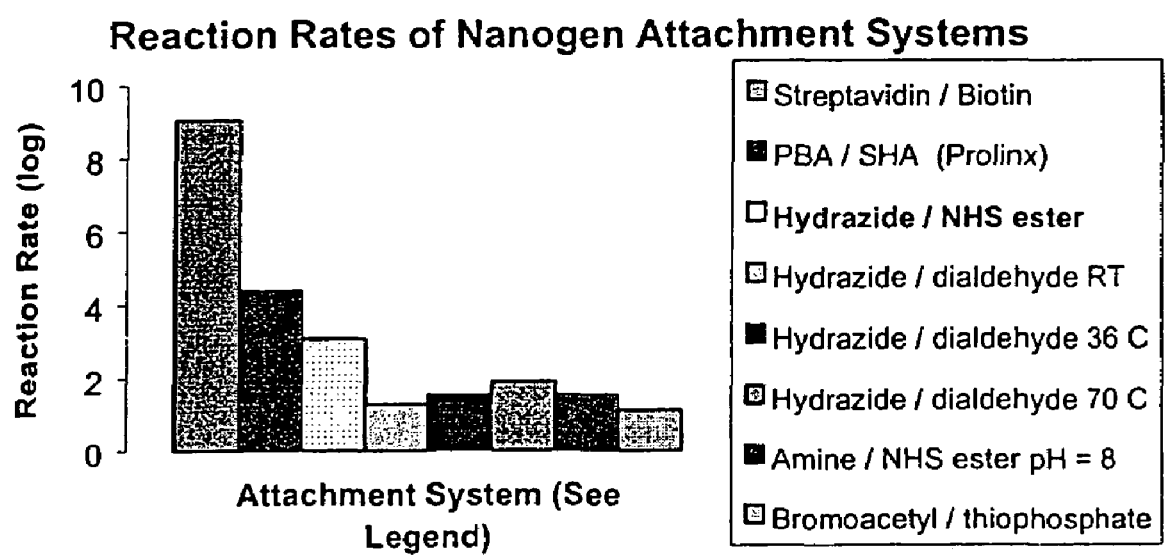
FIG. 11 is a graph that shows reaction rates for attachment of multi-labeled macromolecules. The hydrazide/N-hydroxysuccinimidyl (NHS) ester binding occurred at a rate measurably above that of other covalent binding systems, including the amine/NHS ester binding system, and near to that of two noncovalent systems.

Comparison of this rate to other attachment systems utilized is shown in FIG. 11. The reaction rate for an NHS ester with a hydrazide in an aqueous environment represents an exceptionally efficient reaction. Furthermore, the pH of the reaction was altered to determine the pH dependence of the hydrazide modification. Experiments were carried out with a buffering system of 50 mM histidine adjusted with HCl to pH=6, 5.5, 5.0, 4.5, and 4. The transformation continued down to pH=4.5. However, at pH=4, the hydrazide oligo was unaffected, constituting no transformation and therefore a pH lower limit of approximately 4.5.

Example 8

Attachment of Hydrazide Oligos to Electronically Addressable Microchip Devices

General Electronically Addressable Microchip Preparation:

Microarray containing electronically addressable microchips [Nanogen, Inc., La Jolla, Calif.] are plasma cleaned 5 minutes under Argon. The 25 site 1 cm by 1 cm chips are then silanized using vapor phase deposition. To the center of the microarray is added 0.10 uL of a 20% (by mass) solution of 9:1 (molar ratio) acrylamide/bisacrylamide in 1:1 DMSO/H$_2$O with 0.3% Daracur 4265 as a UV initiator. The chip is placed into a microreaction molding system to which the microarray site is pressed to a UV window containing a square 4 μm cavity, 3 mm on a side. The solution is irradiated for 20 sec with UV light, removed from the molding system, rinsed with water and air dried. The well forms a square hydrogel layer over the microarray. Excess polymerization, beyond the parameters of the mold, is removed.

To the existing permeation layer is added 0.80 μL of a solution containing 20% (by mass) monomer concentration of NHS or Sulfo-NHS/Am/Bis 10/83/7 (molar ratio) and allowed to saturate the existing polymer for 1 minute. The chip is loaded onto the microreaction molding system and polymerized as above with a circular mold with a diameter of 4.6 mm and a well depth of 5 μm. This second mold completely encompasses and extends beyond the existing square layer. Attachment of the second layer is accomplished through intercalation of polymer chains and bind silane. The chips are washed with water and dried with compressed air and subsequently tested in the following experiments.

Experiment 8.1: Activated Ester Concentration and Labeled Capture Address.

To chips modified with the two fold permeation layer as described above containing 0, 1, 2 and 4% Sulfo-NHS was electronically loaded 500 hydrazide-T12-BTR (Bodipy Texas Red) as a specific labeled capture while 50 mM nM biotin-T12-BTR was used as a nonspecific labeled capture. All solutions were buffered in 50 mM histidine. Captures were addressed at a current of 500 nA/pad for 120 seconds, 4 pads at a time. Each chip was washed with 1% SDS, 0.2×STE and soaked in 1% SDS for 20 minutes. The chips were imaged for 1 second and the average MFI values were recorded.

Figure 12:
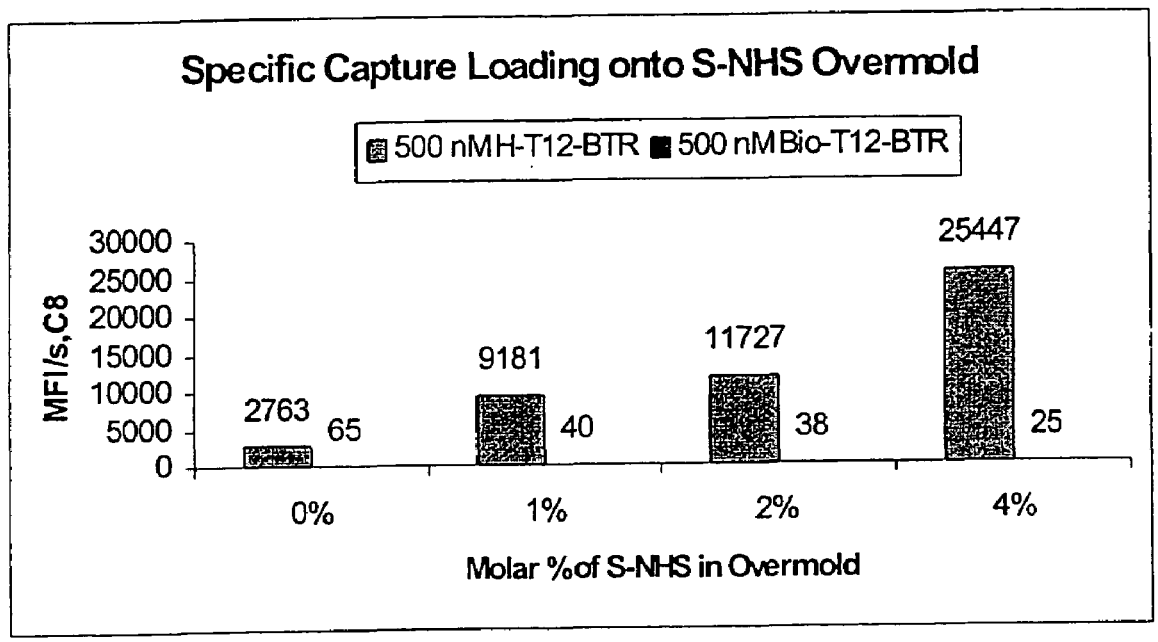
FIG. 12 is a graph that shows that covalent attachment of the labeled hydrazide oligo is dependent on the amount of activated ester in the substrate surface.

As can be seen by in FIG. 12, the covalent attachment of the labeled hydrazide oligo is dependent on the amount of activated ester in the permeation layer and increases as the concentration increases. The nonspecific attachment of a biotin labeled oligo is also quite low, averaging 40 MFI/s for the experiment.

Experiment 8.2: Electronic Conditions and Permeation Layer Attachment:

To chips modified with the two fold permeation layer as described above containing 10% NHS or Sulfo-NHS was electronically loaded 500 and 5 nM hydrazide-T12-BTR as a specific labeled capture. 500 mM nM biotin-T12-BTR was used as a nonspecific labeled capture. All solutions were buffered in 50 mM histidine. Captures were addressed at currents of 400, 500, 600, 700 and 800 nA/pad for 120 seconds, 3 pads at a time. Nonspecific captures were loaded at 800 nA/pad. Each chip was washed with 1% SDS, 0.2×STE and soaked in 1% SDS for 20 minutes. The chips were imaged for 1 second and the average MFI values were recorded.

Figure 13:
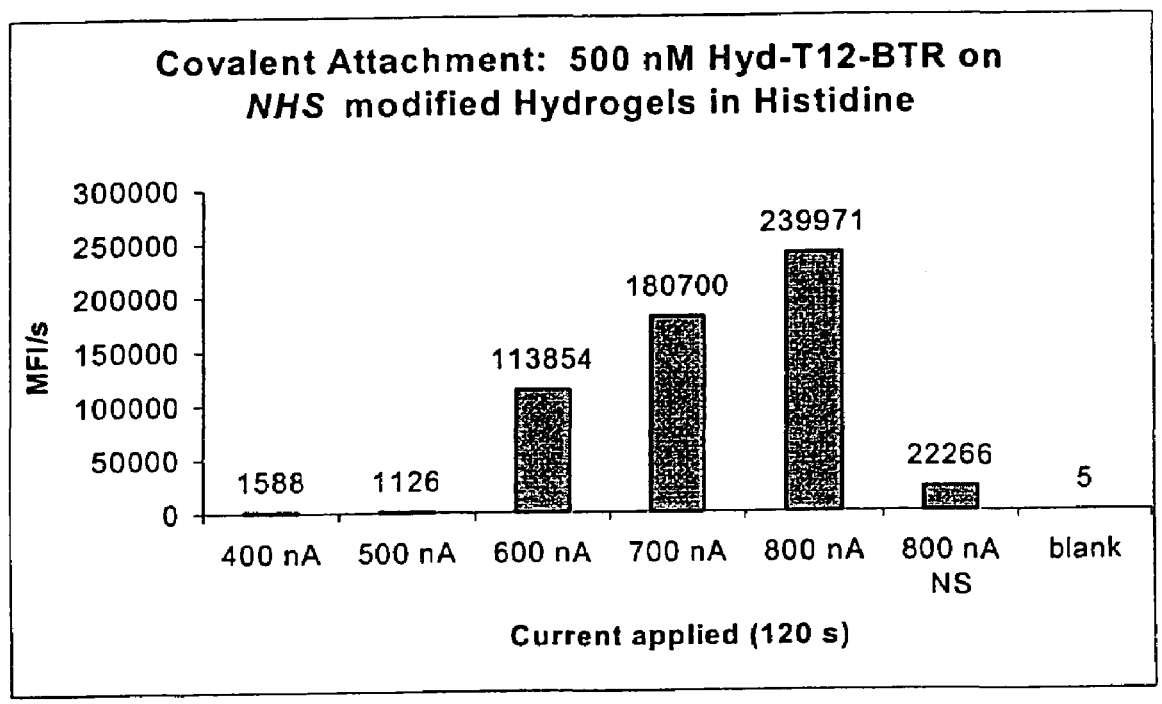
FIGS. 13 and 14 are graphs showing the proficiency of covalent attachment for either NHS or N-hydroxy-sulfosuccinimidyl (Sulfo-NHS) ester modified substrate surfaces respectively. The graphs show the specific and nonspecific fluorescent intensity from labeled oligomers attached to the electrodes over a range of applied currents.
Figure 14:
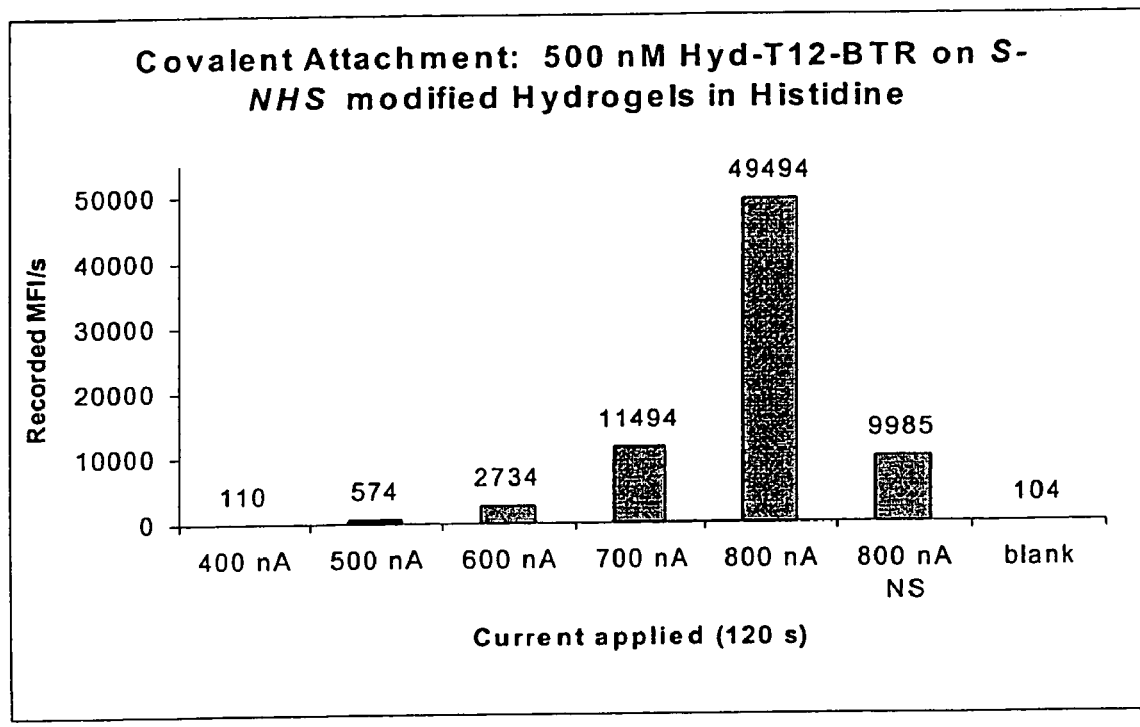

As can be seen by in FIG. 13, attachment of a specific capture to the NHS modified permeation layer dramatically increases at 600 nA, while Sulfo-NHS modified hydrogels required a slightly higher current for maximum attachment (FIG. 14).

Experiment 8.3: Effect of Multiple Attachment Moieties on the Oligos

To chips modified with the two fold permeation layer as described above containing 10% NHS were loaded Cy3 labeled ATA5 oligos containing 1, 2, 4, or 8 hydrazide moieties. The four oligomers were electronically addressed at 500 nM with a current of either 700 or 800 nA/pad for 120 s, buffered in 50 mM histidine. Upon completion, the chips were washed and the binding levels were measured.

Figure 15:
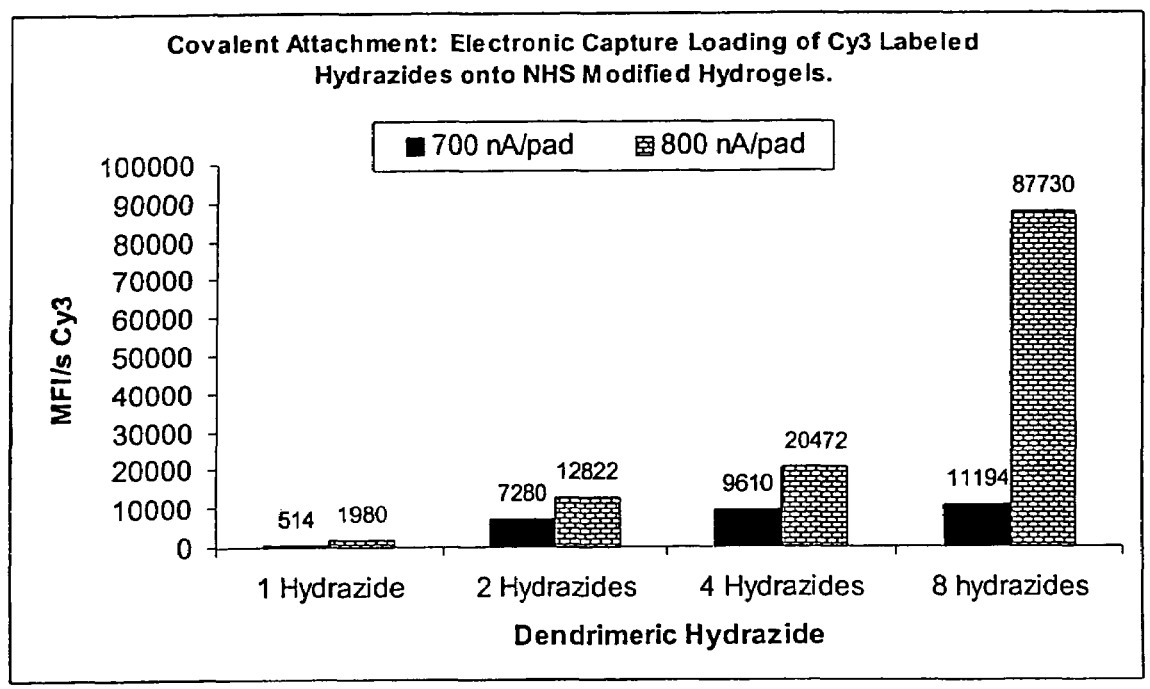
FIG. 15 is a graph that shows that multiple binding of hydrazide moieties provides higher level of detection of the macromolecule on the substrate.

The recorded MFI/s values are displayed in FIG. 15. A comparison the number of hydrazide moieties available for attachment per oligomer given equal currents indicates an increased binding level with the increase in the number of hydrazides on the oligomer.

Experiment 8.4: Reverse Dot-blot Electronic Hybridization

To chips modified with the two fold permeation layer as described above containing 15% NHS was loaded an octahydrazide ATA5 oligomer with a Cy3 label as a specific capture. The specific capture was loaded at 500 nM with a current of either 600 or 700 nA/pad for 120 s, buffered in 50 mM histidine. Electronic Hybridization was carried out with 5 nM RCA5-T12-Cy5 as a specific target while a solution of 5 nM RCA4-Cy5 was used as a nonspecific target. The targets were loaded at 400 nA/pad for 60 seconds, the chips were washed according to the standard protocol and imaged.

Figure 16:
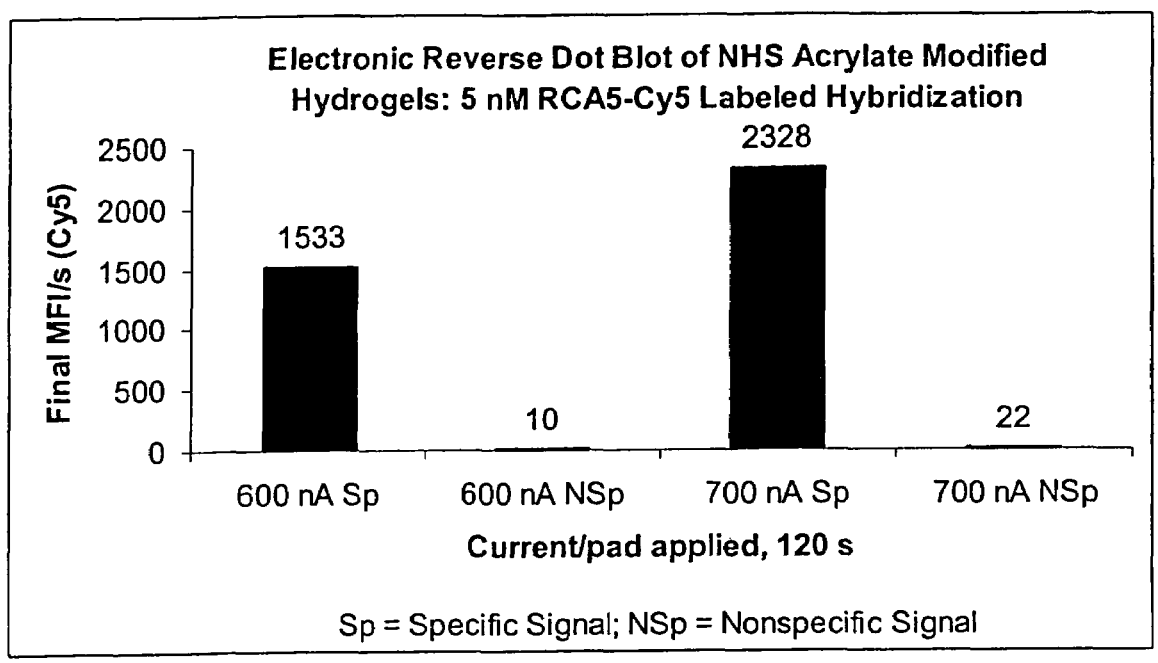
FIG. 16 is a graph that shows results of an electronic reverse dot blot in which hybridization was completed only on those sites containing a hydrazide-modified oligo (ATA5). The capture probes were specifically bound to an activated-ester-containing substrate under appropriate electronic conditions. The nonspecific captures without a hydrazide do not react with the activated ester and are therefore unavailable for hybridization.

The data presented in FIG. 16 clearly indicates the hybridization of the specific target preferentially to the nonspecific target. It should also be noted that in agreement with data reported above, the increase in current, from 600 to 700 nA for the electronic loading of the capture results in an increase in the hybridization.

Example 9

Synthesis of Macromolecules having Noncovalent Attachment Moieties

Figure 4:
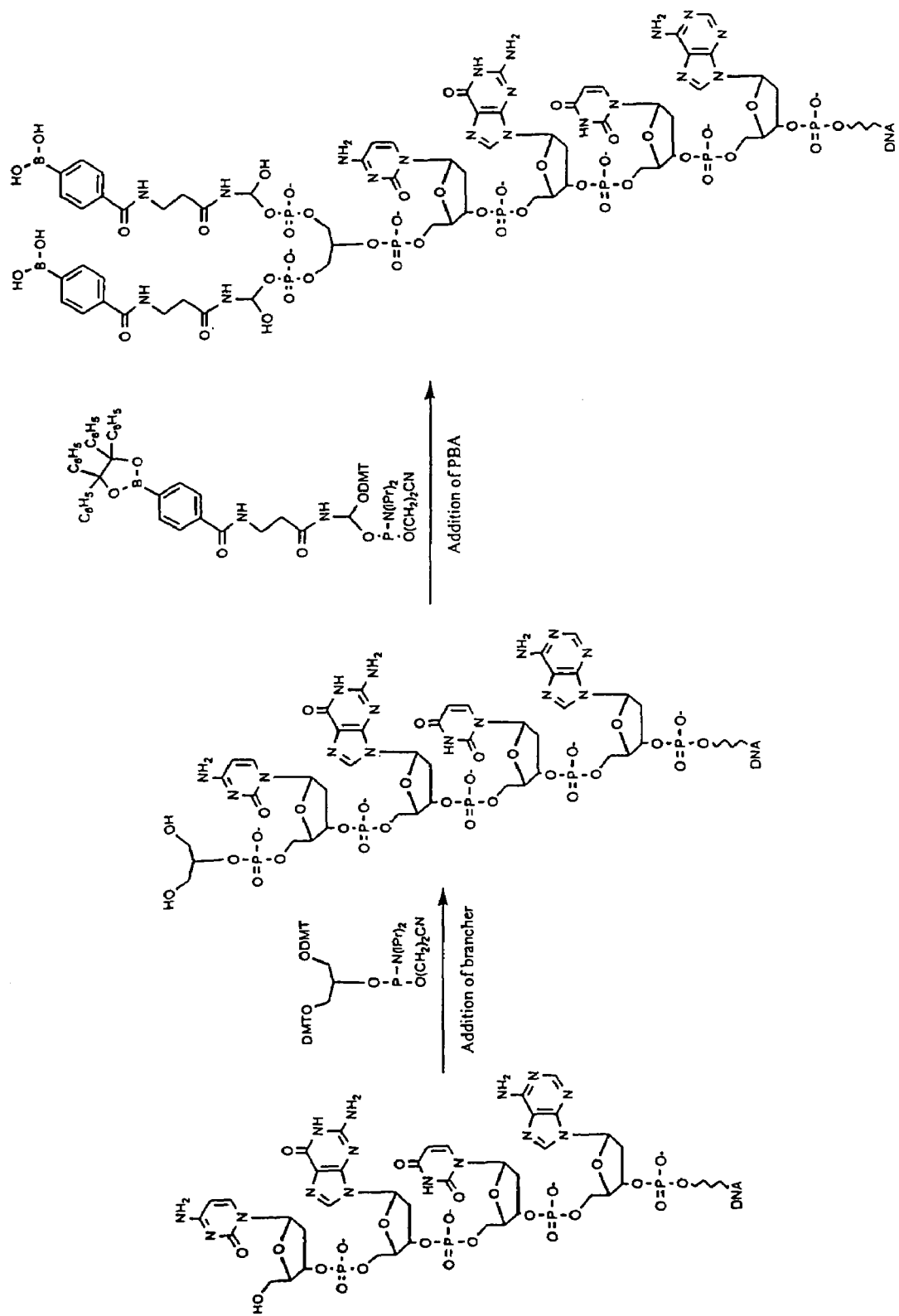
FIG. 4 shows a series of chemical steps to produce a structure having a dendrimeric structure containing phenyl boronic acid (PBA) attachment moieties.
Figure 5A:
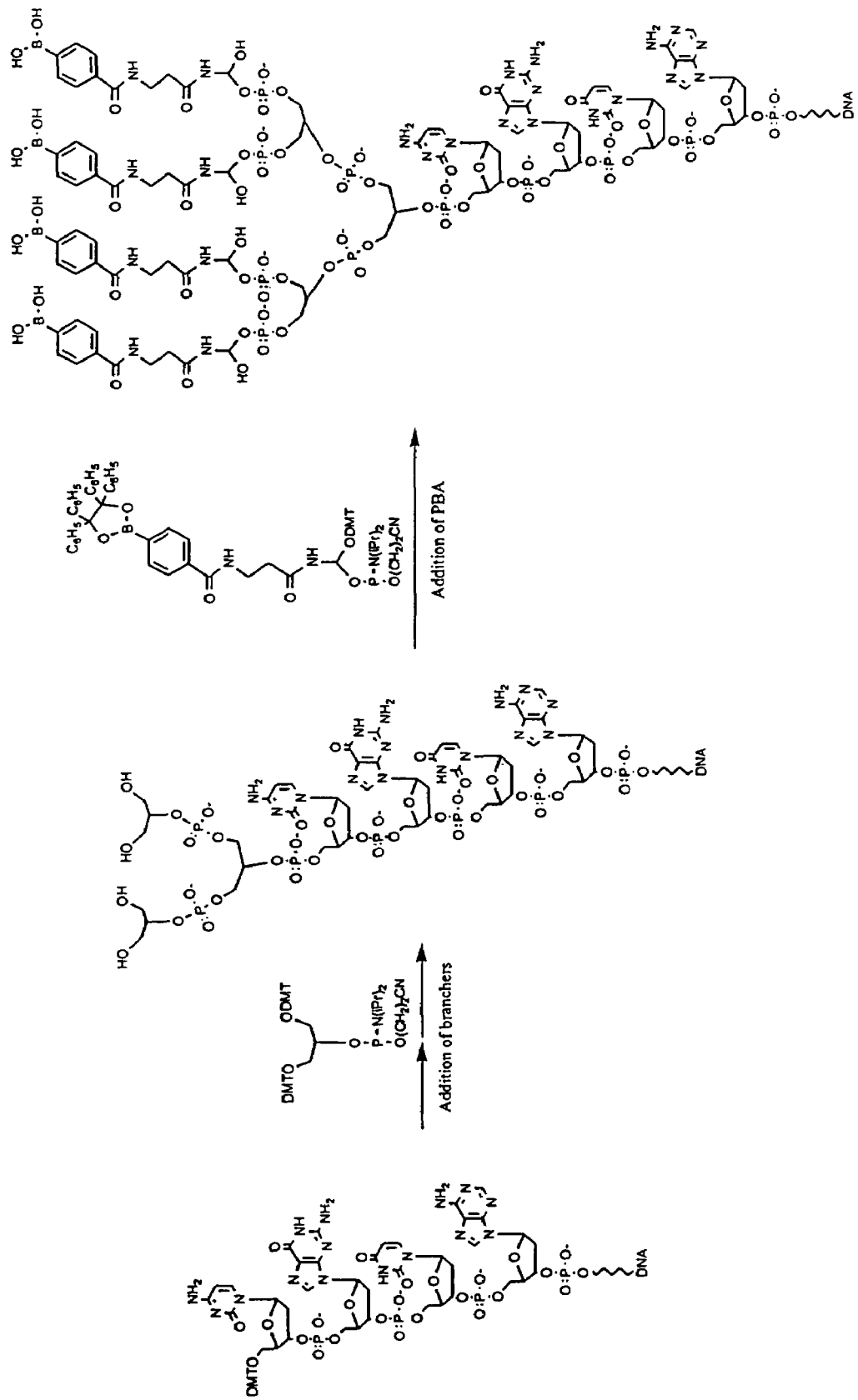
FIGS. 5A and B show a series of chemical steps to produce chemical structures comprising oligo macromolecules having either four (A) or eight (B) attachment moieties for noncovalent binding of the macromolecule to a substrate surface.
Figure 5B:
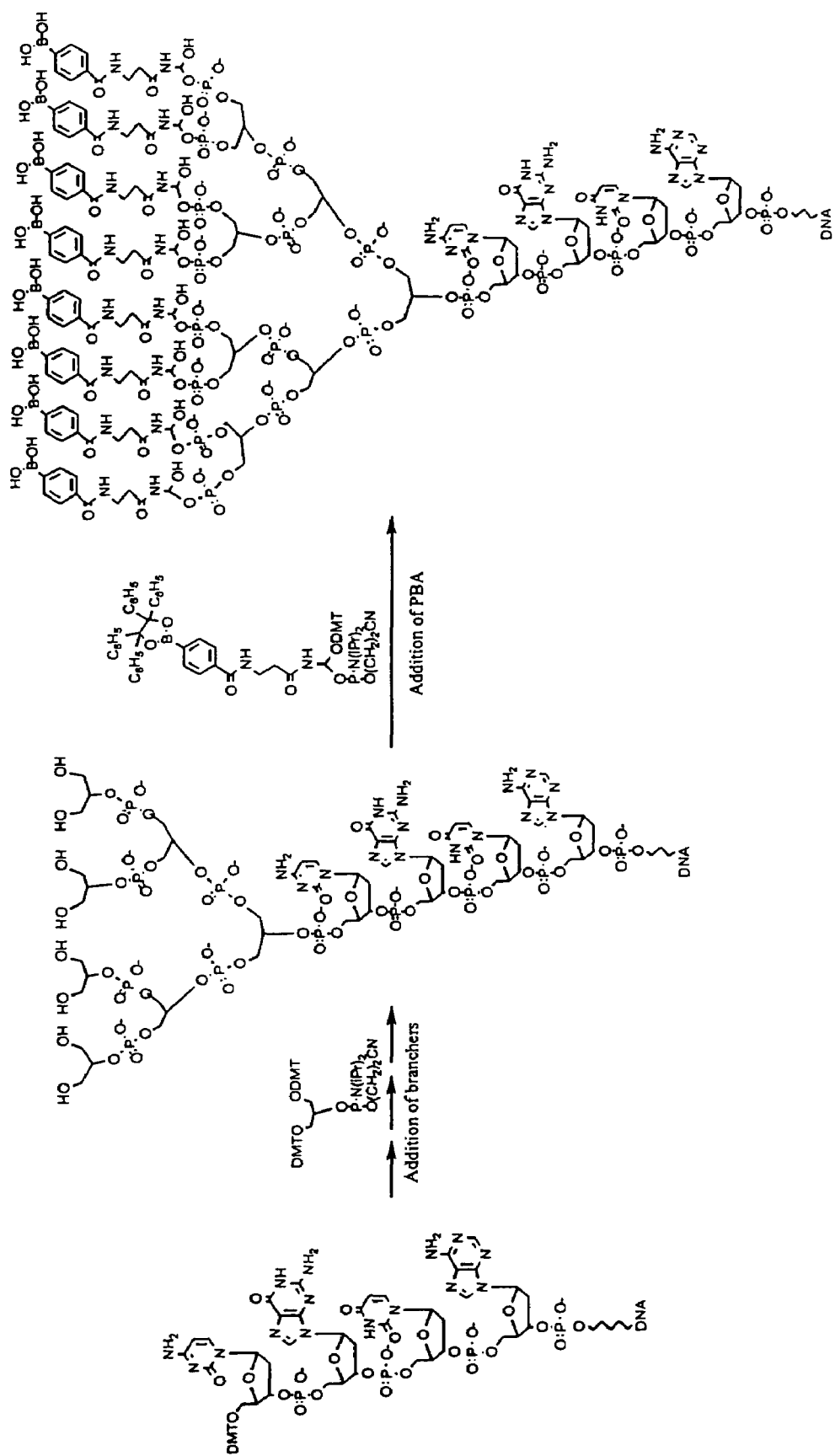

FIGS. 4 and 5A and B depict the syntheses of oligos containing multiple attachment moieties. In FIG. 4, oligo synthesis is depicted wherein there is added a single branched phosphoramidite containing two PBAs. FIGS. 5A and B show two branches with four PBAs, and three branches with eight PBAs, respectively. Syntheses as depicted were carried out on an ABI394 DNA Synthesizer. The stepwise coupling yield of branched phosphoramidite was similar to the regular nucleotide phosphoramidites, about 96–98%. The PBA phosphoramidite was applied at the last step. The cleaving of oligos from the solid support and the removal of protecting groups were the same as the handling of regular oligos as is well known to those of skill in the art. See above Example 6 for an alternative process of in-situ generation of PBA moieties from hydrazide moieties on the oligos.

The PBA-containing branched oligos were purified and analyzed by HPLC. The HPLC of PBA-containing oligo showed a broader peak than that of a regular oligo.

Experiment 9.1: Electronic Loading of Oligos Via Noncovalent Attachment Moieties.

20 nM non-branched and branched PBA-containing ATA5 capture probes were loaded on hydrogel substrates electronically. The capture probes were loaded in 50 mM histidine, 10 pads at a time for 120 seconds. 20 nM RCA5-BTR was loaded passively for 5 minutes. The substrates were washed and imaged. Analysis showed that both branched and unbranched capture probes were immobilized to the permeation layer, as desired.

Experiment 9.2: Stability of Electronically Loaded Macromolecules with Non-covalent Attachment Moieties.

Figure 21:
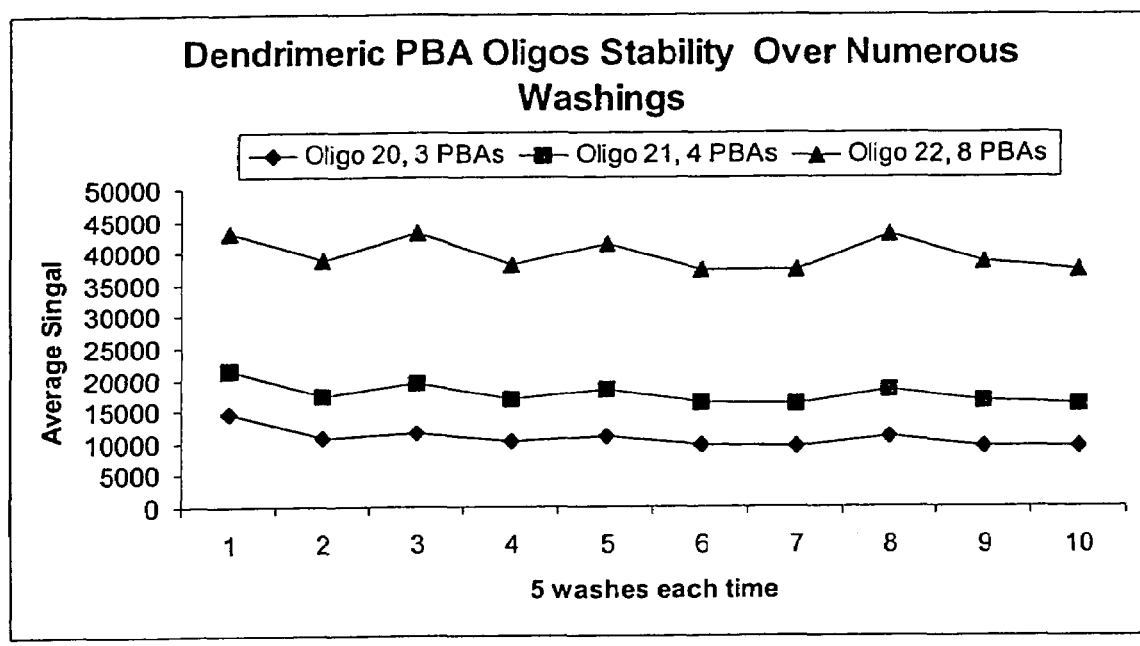
FIG. 21 shows the recorded mean fluorescent intensity (MFI) values for oligomers labeled with 3, 4, and 8 phenylboronic acids per oligo. The attached oligomers were subjected to vigorous washing conditions to monitor the stability of the attachment system.

Oligos 20, 21 and 22 (p-RNAs containing 3, 4, and 8 PBA attachment sites) were electronically addressed to SHA modified hydrogel chips. Upon completion, initial images were recorded after a standard washing procedure previously described. The chip arrays were then subject to regular irrigation with repeated rinsing with 10 uL of 50 mM histidine. Images were recorded after 5 washings. The results shown in FIG. 21 contain 2 features. Primarily the recorded signals for the higher order dendrimers which have a higher number of attachment sites per oligo is distinctly higher. Also, the signal is quite stable over a period of 25 wash cycles illustrating the improved stability of the use of dendrimeric attachment systems. Oligo 22 has lost approximately 14% of its initial signal while oligos 20 and 21 have decreased 25 and 35% respectively.

Example 6

Covalent Attachment by Multiple Hydrazone Formation

Oligos modified with a single amine or hydrazide may be electronically loaded onto aldehyde modified hydrogels. The interaction of an aldehyde with an amine or hydrazide results in the formation of an imine (carbon with a double bond to nitrogen) or a hydrazone respectively. These reactions are reversible under aqueous conditions and require further reduction with NaBH$_3$CN to form a stable irreversible covalent attachment. Indeed, electronic concentration of an oligomer containing a single hydrazide resulted in attachment of the oligomer to the surface via hydrazone formation. Elimination of the reduction step resulted in a relatively easily hydrolyzed and unstable linkage in which the bound oligo diffused away within a time period relevant to many uses of the array.

Figure 22:
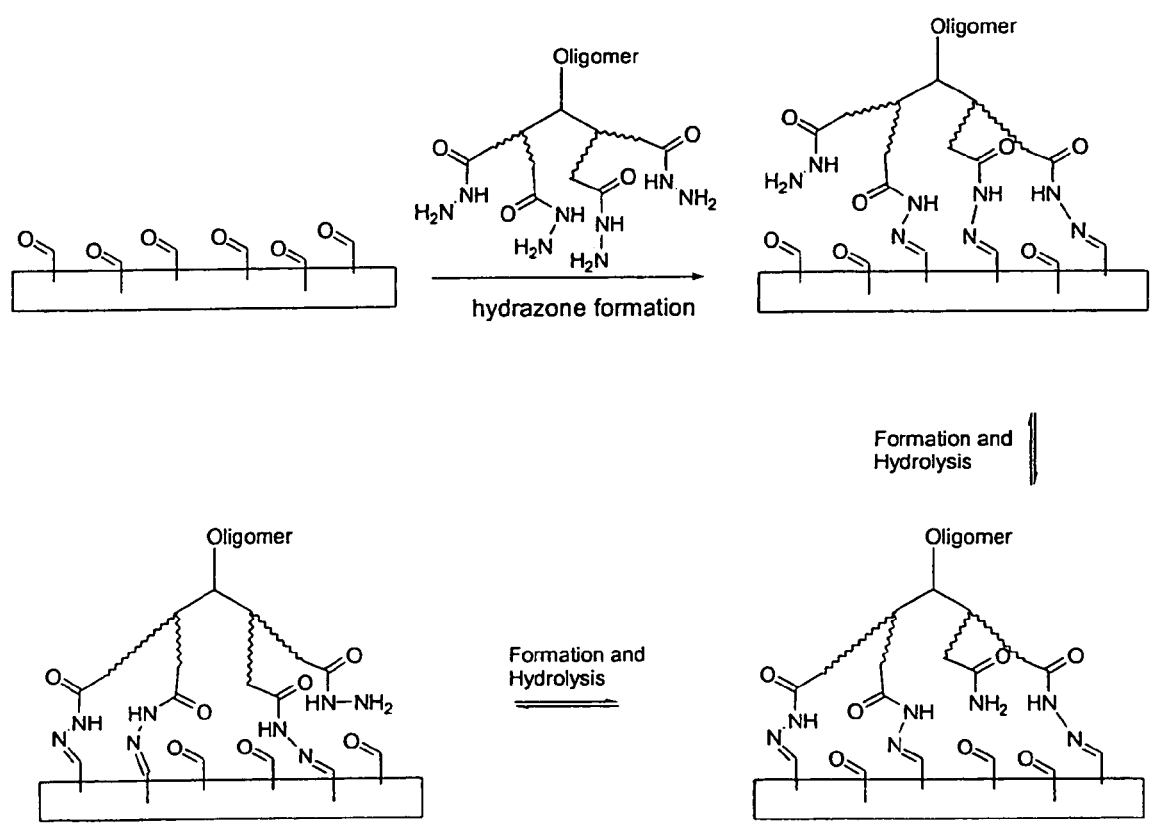
FIG. 22 shows a schematic illustrating the dynamic equilibrium and stability of dendrimeric hydrazides onto an aldehyde rich permeation layer. The oligomer, displayed with four hydrazide moieties, is electronically loaded onto an aldehyde rich permeation layer resulting in multiple hydrazone linkages. In this particular example, the linkages individually are susceptible to hydrolysis. The stability gained with the use of multiple attachment sites allows for hydrolysis of some hydrazones while others remain intact. The hydrazide, tethered through neighboring hydrazone attachment sites, is incapable of diffusion and is therefore retained within the aldehyde rich permeation layer capable of re-establishing the linkage.

The use of dendrimeric hydrazides provides a means of covalent attachment through a somewhat unstable linkage which does not require further reduction; provided there are a sufficient number of hydrazones formed per oligo. The reversible hydrazone formation can occur with some linkage sites while others remain intact (FIG. 22). The hydrazide is incapable of diffusion, and trapped within an aldehyde rich environment, can readily reform. This equilibrium takes advantage of the increased number of attachment sites per oligo and, provided all linkages do not hydrolyze at once, is contemplated to provide a stable attachment system. Aldehyde rich permeation layers can be prepared directly, as in glyoxyl agarose, or can be obtained from an acetal modified permeation layer. In the latter, the acetal moiety is readily hydrolyzed in the presence of acid to afford an aldehyde. The acetal serves as a protecting group, preserving the aldehyde functionality until activation is desired. Hydrolysis can be completed with exposure to an acidic solution for 1 hr or subjected to a mild electronic current buffered in a dilute salt solution. The latter method provides site specific hydrolysis by taking advantage of the acid generated at the cathode.

Experiment 9.1: Dendrimeric Hydrazide Oligomers Attached to Glyoxyl Agarose.

Figure 23:
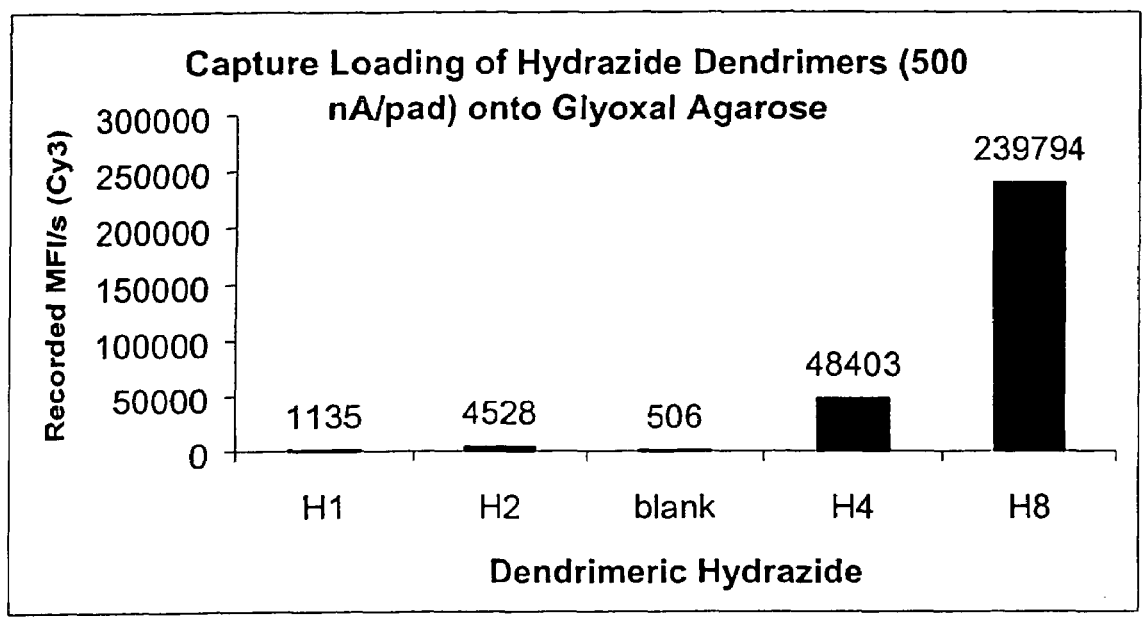
FIG. 23 is a graph showing the attachment of dendrimeric oligomers of 1, 2, 4, and 8 hydrazides onto glyoxal agarose permeation layers coupled via hydrazone linkage(s).

Standard 25 site chips were spin coated with glyoxyl agarose (FMC, Princeton, N.J.)). 500 nM Hydrazide Cy3 labeled oligos containing 1, 2, 4, and 8 hydrazides were electronically loaded at 500 nA/pad for 2 minutes each, buffered in 50 mM histidine. The chips were washed according to established procedure and imaged. The recorded MFI/s values are displayed in FIG. 23. The oligos with one or two hydrazides were quite unstable and as expected afforded little detectable fluorescence above background noise. The oligos with a higher number of hydrazides are capable of forming a stable covalent attachment with aldehyde-modified surfaces.

Experiment 9.2: Dendrimeric Hydrazide Oligomers Attached to Acetal Modified Hydrogels: Deprotection and Covalent Attachment.

25 array site electronically addressable microchips were modified with a single layer hydrogel composed of acrylamide, bisacrylamide and vinyl acetal in a 15:2:3 ratio. Selected sites were activated at a current of 300 nA/pad for 2 minutes in a 50 mM NaCl solution to hydrolyze the acetal functionality exposing the aldehydes. Dendrimeric hydrazide oligomers containing 8 hydrazides per oligo were electronically loaded at 500 nA/pad for 2 minutes buffered in 50 mM histidine to pads which had been activated and to those that had not. A nonspecific oligo was also electronically loaded onto both acetal and aldehyde modified sites. After a standard wash cycle, the chips were imaged. The recorded MFI/s data is displayed in FIG. 24.

Figure 24:
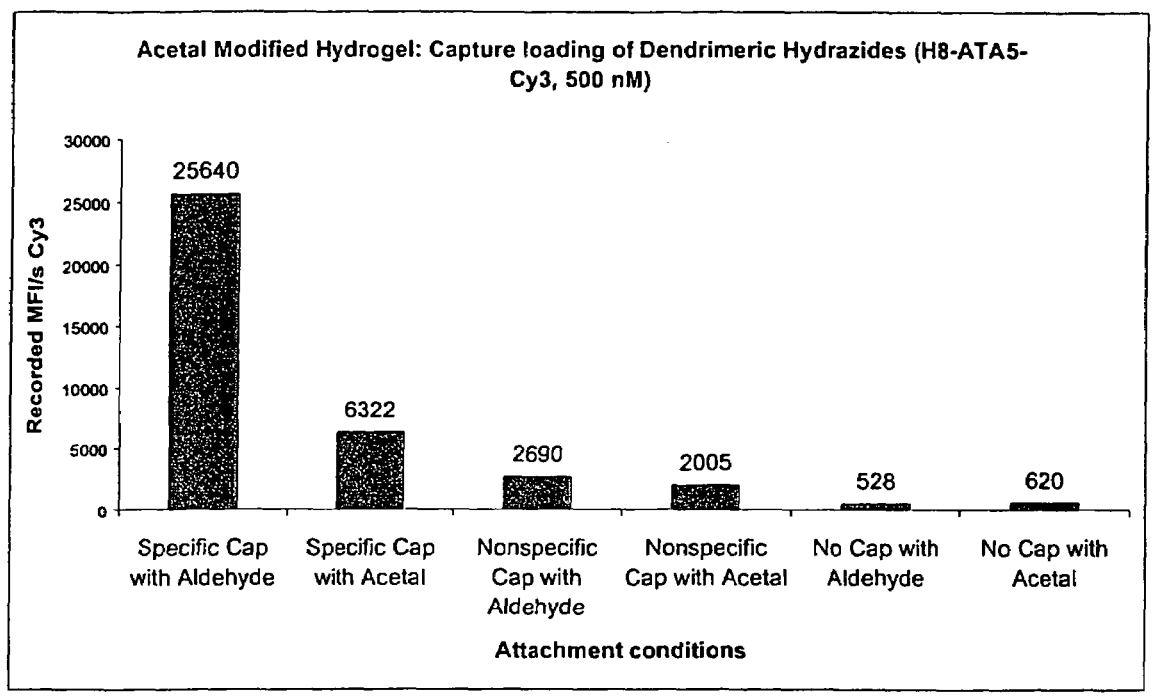
FIG. 24 is a graph showing the attachment of dendrimeric oligomers onto an acetal modified hydrogel. The acetal moieties require hydrolysis with acid to generate aldehydes for covalent attachment capabilities.

As can be seen in FIG. 24, pads which had been electronically activated, then loaded electronically with a dendrimeric labeled oligomer exhibit the highest fluorescence signal. Interestingly, those pads which were not pre-addressed, remaining as acetals also indicate some attachment of hydrazide modified oligomers. Presumably, the electronic current applied to concentrate the oligomer generated enough acid to surpass the buffering capacity of histidine locally and was therefore able to hydrolyze a significant quantity of acetal moieties.

Example 10

Use of Hydrazide-Modified Oligos in Non-substrate Surface Coupling Reactions: Labeling, etc.

Figure 19:
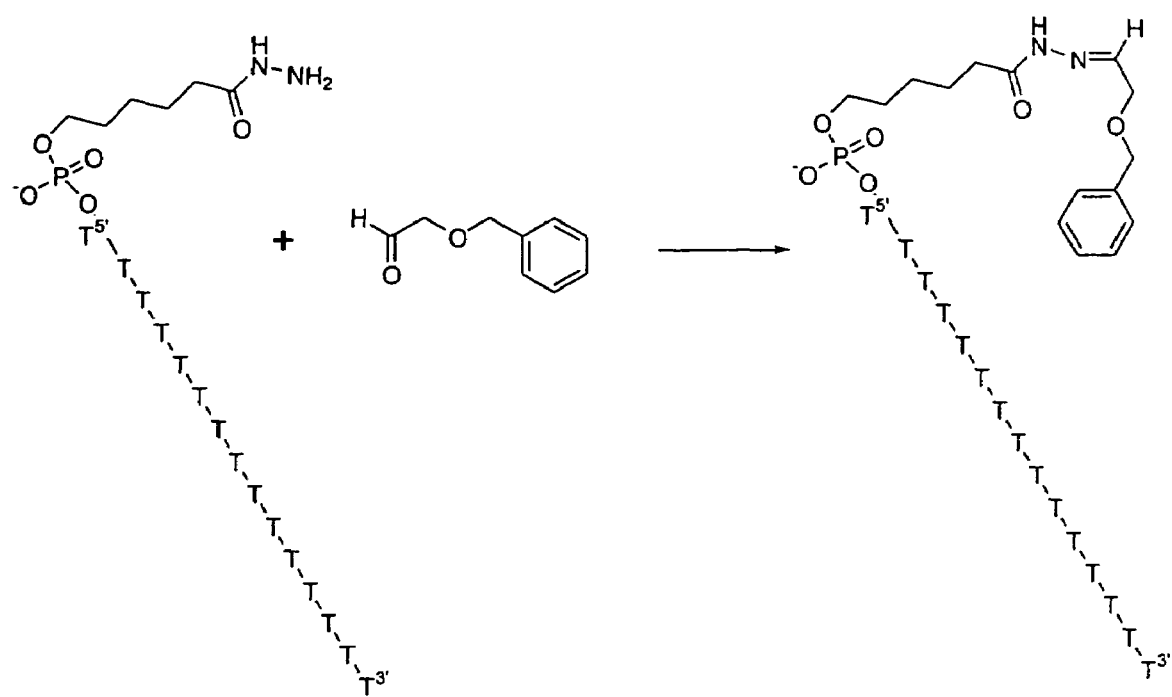
FIGS. 19 and 20 are examples of hydrazide oligomers condensing with aldehydes.

Experiment 10.1 Reaction of Hydrazide-15mer 9 with Benzyloxy Acetaldehyde; FIG. 19.

10 μmol Hydrazide Oligo 9 were dissolved in 60 μL 10 mM ammonium acetate buffer (pH 4.0). 1 drop benzyloxyacetaldehyde (CAS: 6065-87-3; C9H10O2 [150.1760] Aldrich No. 38,218-3) was added and the mixture was allowed to stand at RT for 1 h. The solvent and excess of aldehyde was removed in vacuo and the product was analyzed by HPLC (Column: Merck LiChrospher RP 18, 10 μM, 4×250 mm; Buffer A=0.1 M triethylammonium acetate pH=7.0, Buffer B=75% acetonitrile in buffer A; Flow=1.0 mL/min; Gradient: 0% B to 100% B in 100 min). The retention time of the product is 30, 7 min, oligo 9 elutes at 25.5 min.

Figure 20:
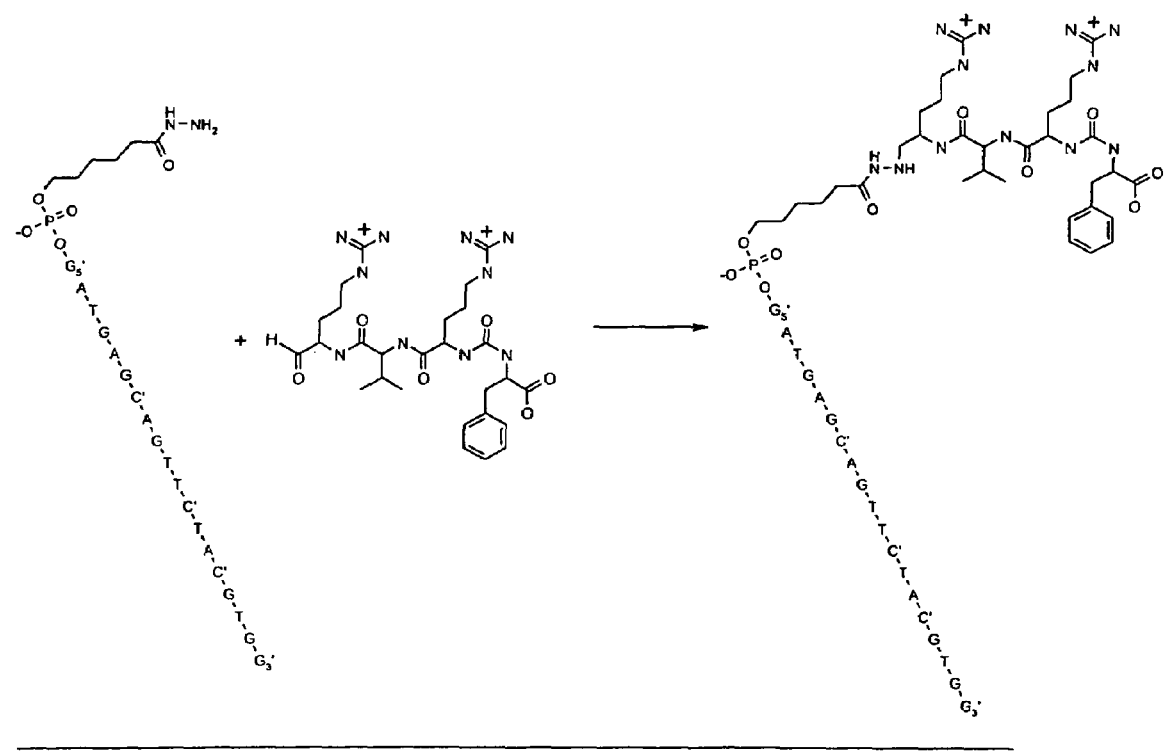

Experiment 10.2 Conjugation Reaction of Oligo 10 with a Peptide, FIG. 20.

4.4 nmol Oligo 10 were dissolved in 60 μL 10 mM ammonium acetate buffer (pH 4.0). 44 nmol (10 eq.) antipain hydrochloride (CAS: 37682-72-7; C27H44N10O6.2 HCl; [677.6304]; Calbio No. F 178220) in 15 μL buffer were added and agitated 3 h at RT. The intermediate product was reduced with NaBH$_3$CN (100 eq.) for 1 h at RT. The product was isolated by HPLC (Column: Merck LiChrospher RP 18, 10 μM, 4×250 mm; Buffer A=0.1 M triethylammonium acetate pH=7.0, Buffer B=75% acetonitrile in buffer A; Flow=1.0 mL/min; Gradient: 10% B to 85% B in 60 min). The retention time of the product (oligo peptide conjugate) is 16.5 min, oligo 10 elutes at 13.9 min. MS (ESI): calc: 6680.6; obs.: 6679.6)

Example 11

Passive Application of Hydrazide Modified Macromolecules on Slide Surfaces

For the binding of hydrazide modified oligos to commercially available slides a series of p-RNA oligos containing 1 to 16 hydrazides were used. Along with oligos 12, 13, and 14, oligomers with 3 and 6 hydrazides, prepared from 1d, were used. Additionally, an amine terminated oligomer (prepared with 5' Amino Modifier C6; Glenn Research) and an oligo without modification are used as nonspecific controls. All oligomers are labeled with Cy3 at the 2' end and retain the same nucleotide sequence.

Experiment 11.1: Attachment to Surmodics 3D Link™ Amine Binding Slides.

Figure 25:
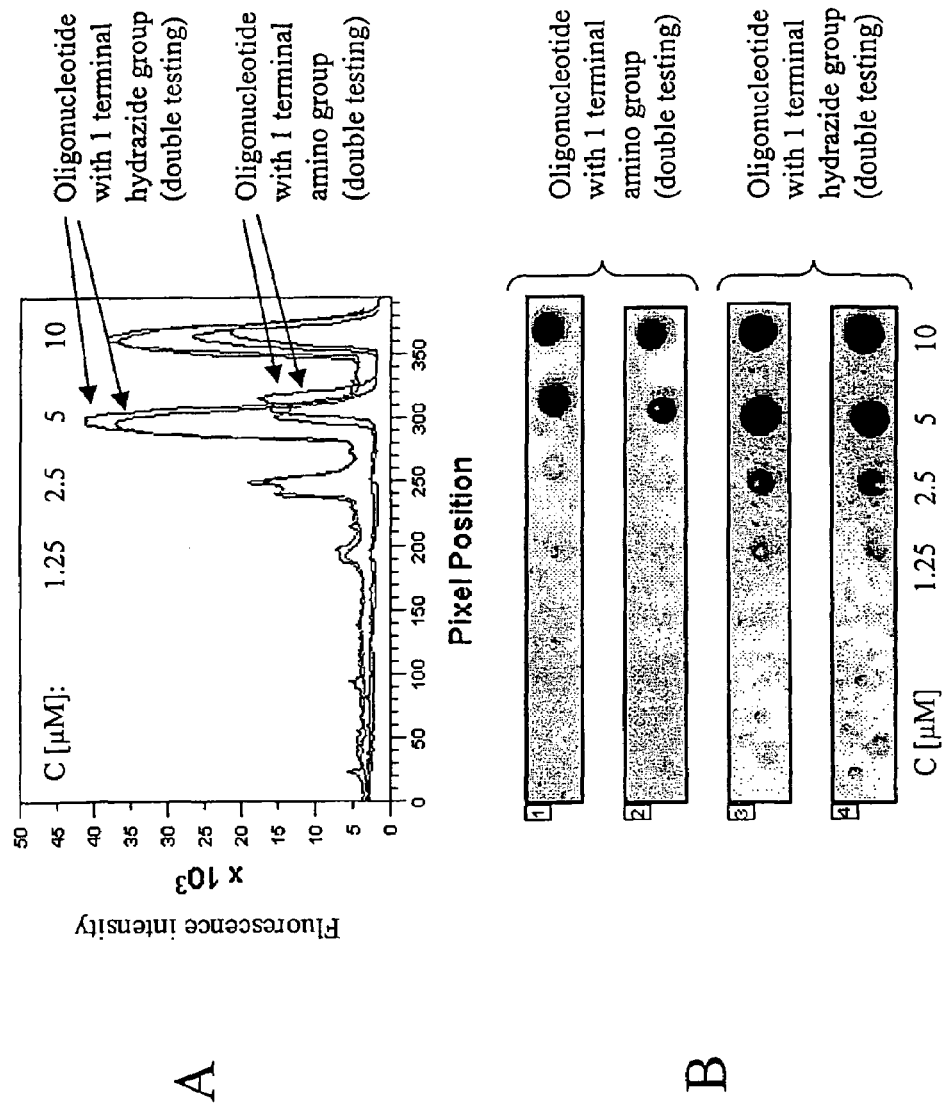
FIG. 25 illustrates the use and improved binding of hydrazide oligomers on Surmodics 3D Link™ Amine Binding Slides at various concentrations.

Oligos are dissolved in 3D Link™ print buffer (Surmodics, Inc, Eden Prairie, Minn.) at pH=8.5 with concentrations ranging between 10 μM and 100 nM. From each solution, 0.5 μL was applied directly to the slide surface and incubated at room temp. in a sealed chamber above a saturated NaCl solution overnight in the dark. The slides were then treated for 15 min at 50° C. with 3D Link™ blocking buffer to block unreacted surface sites. The slides were washed twice with water followed by a 30 min wash with 0.2% SDS at 50° C. and finally two water washings, then allowed to air dry. The fluorescence detection was preformed on a Pharmacis scanner with 20 second integration times. Images as well as intensity profiles are displayed in FIG. 25.

The nonspecific oligo afforded a signal between 10×10³ and 25×10³ relative units at 10 µM. The signal compares in intensity with that observed for an oligo containing a single amino group. In contrast, the hydrazide modified oligo affords a much higher loading of 35–40×10³ fluorescence units. Further, the hydrazide modified oligo has a higher fluorescence signal at lower concentrations, with a lower limit of detection of 1.25 µM, as compared to the amine modified oligomer which has a lower detection limit of 5 µM.

Experiment 11.2: Attachment to SuperAldehyde Slides.

Oligos were dissolved in either Surmodics 3D Link™ print buffer at pH=8.5 with concentrations ranging from 10 µM to 100 nM or in 10 mM ammonium acetate buffer at pH=4.0. From each solution, 0.5 µM are applied to the surface of SuperAldehyde slides (Telechem International, Inc Sunnyvale, Calif.) and allowed to incubate overnight at rt. The slides were then treated twice with 0.2% SDS and washed 4 times with water (2 min each). The surface was then treated with a solution of 0.3% $NaBH_3CN$ in PBS buffer, pH=7, with 133 mL ethanol to eliminate bubbling. This was followed by three 1 min washings with 0.2% SDS and water. Fluorescence detection was preformed on a Pharmacis scanner with 20 s integration times. Images as well as intensity profiles are displayed in FIG. 26.

Figure 26:
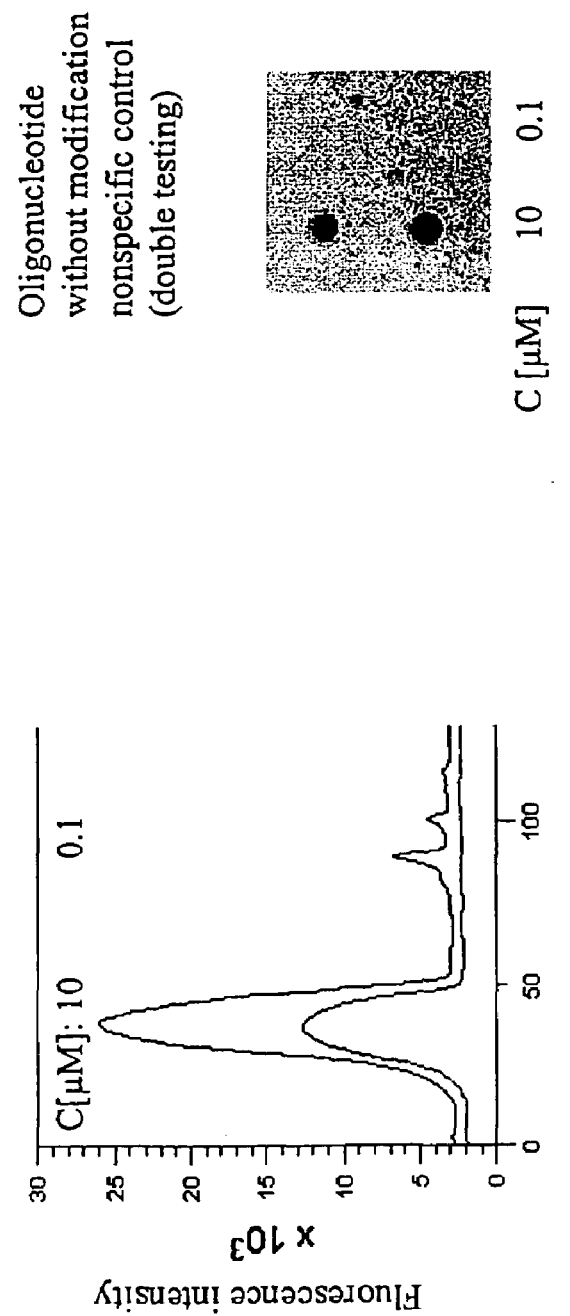
FIG. 26 displays the nonspecific attachment binding levels to the Surmodics slide used in FIG. 25.
Figure 27:
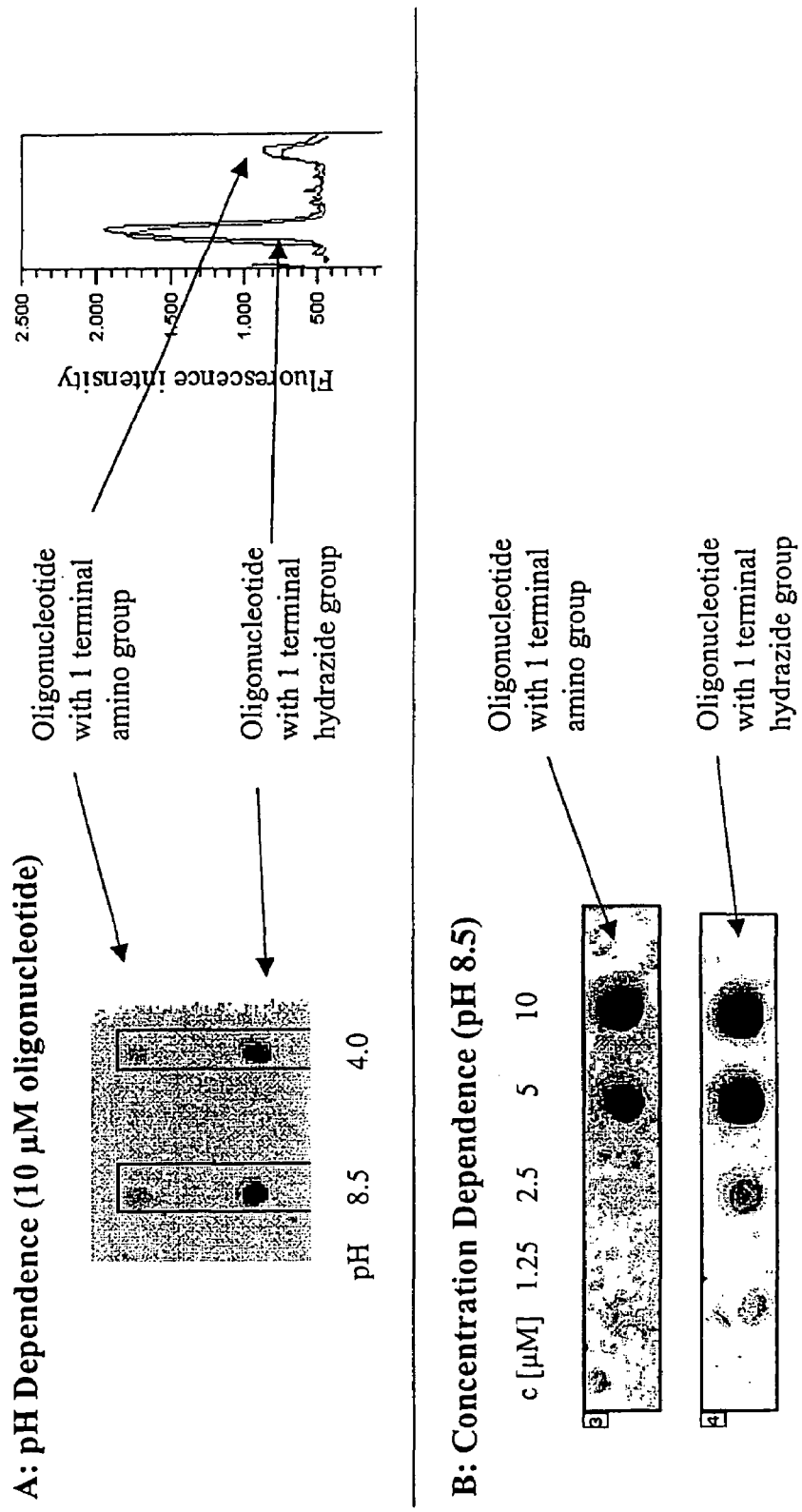
FIG. 27A shows the applicable pH range in which the hydrazide oligomers are capable of successful immobilization to a solid support.
FIG. 27B displays the improved sensitivity of a hydrazide oligomer over a standard amine modified oligomer being detectable at lower concentrations.
Figure 28:
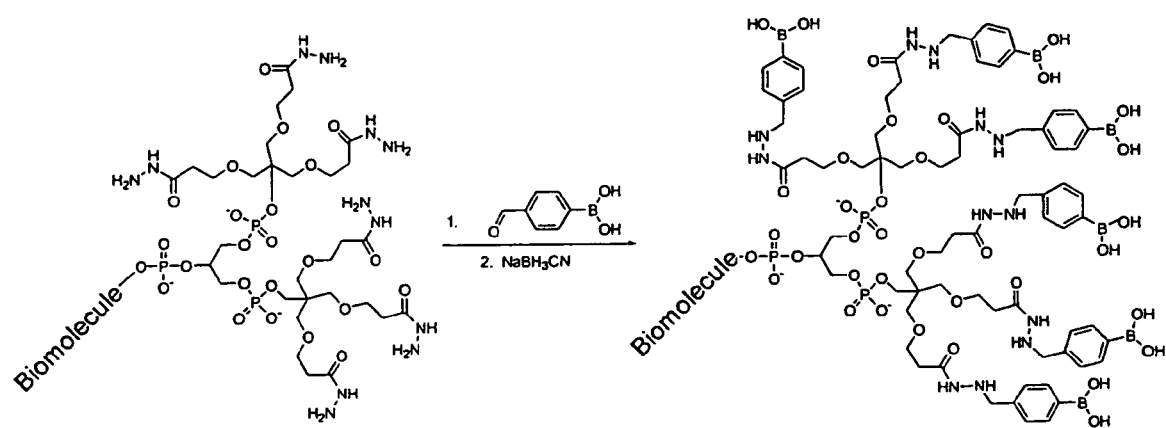
FIG. 28 illustrates one example of how a branched or unbranched hydrazide modified oligomer can be easily modified to an alternative attachment system. In this particular example a branched oligomer with six hydrazides is modified with p-formylphenylboronic acid to afford a branched PBA attachment probe.

As can be seen if FIG. 26, at both pH=8.5 and 4.0 the hydrazide oligo affords a much higher signal intensity as compared to the amine terminated oligomer and is unaffected by the change in pH. Furthermore, given the same concentrations, the hydrazide modified oligomer affords much higher signal intensity than the amine modified oligomers. The amine oligos are no longer detectable below 2.5 µM while the hydrazide oligomers are detected as low as 1.25 µM.

Example 12

Comparison of Hydrazine and Amine Attachment Moieties on Active Ester Surfaces

Figure 29:
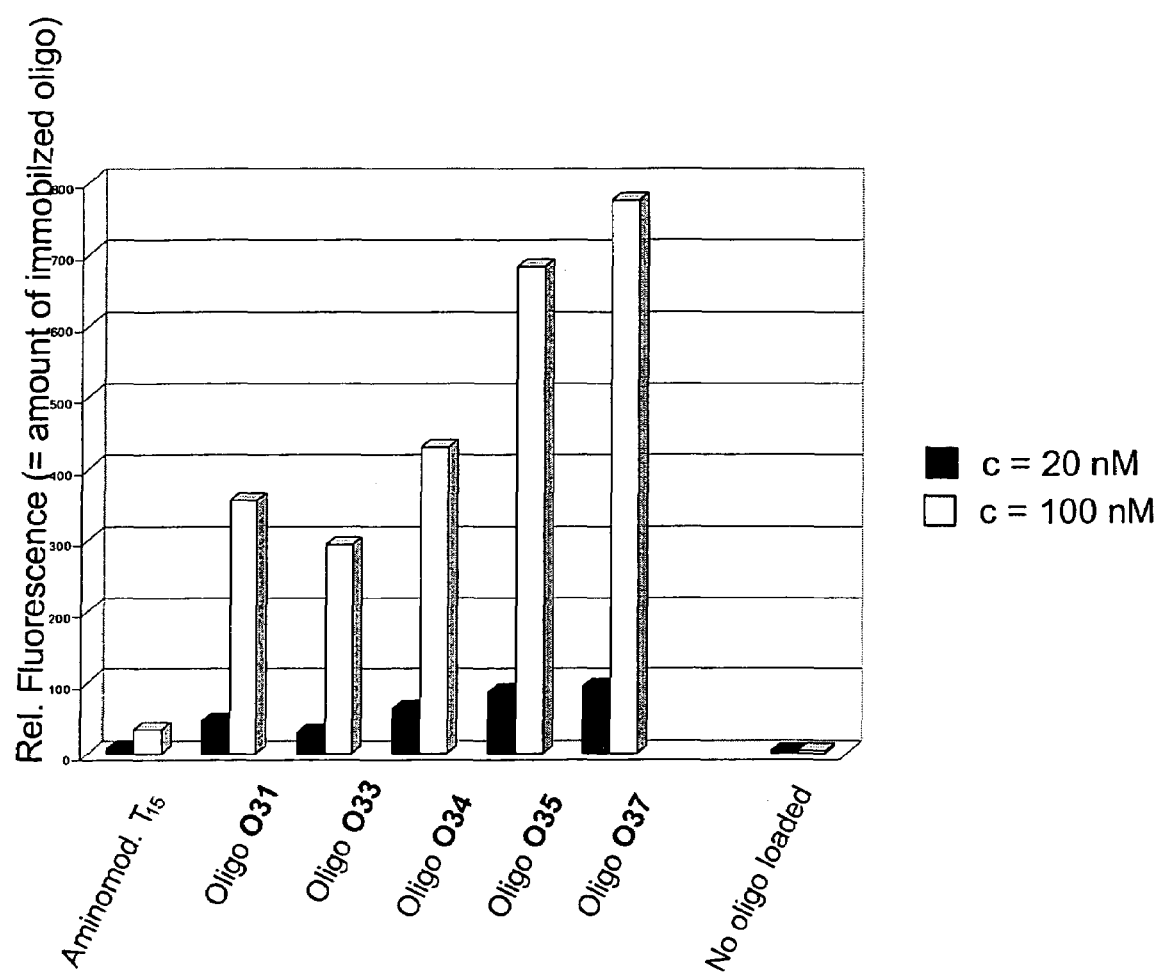
FIG. 29 shows graphically a comparison of the attachment of several hydrazide-modified oligos (specifically -$T_{15}$-Cy3 oligos) to NHS active ester hydrogels on a bioelectronic array device (NanoChip™ Cartridge). Note that the single hydrazide modified oligo O31 produced >7 times more immobilized oligo than the amino-modified oligo at both concentrations used, and the tetra-hydrazide modified oligos O35 and O37 produced about 12–15 times as much immobilized oligo as the amino-modified oligo.

For comparison, a amino-C6-modified and Cy3 labeled oligonucleotide $T_{15}$ (5'-AminoC6-TTT TTT TTT TTT TTT Cy3) was purchased from Biospring GmbH, Frankfurt/Main, Germany. Using this oligo, and the following oligos, 20 µM and 100 µM solutions in 50 mM histidine buffer were made and filtered through a Millipore ULTRAFREE-MC 0.22 µm filter unit: O31, O33, O34, O35, O37, O39. These resulting solutions were addressed on an active ester NHS permeation layer Nanogen Chip by addressing two pads simultaneously for each probe for 180 s at 2.2V. Cy3 fluorescence was recorded at low gain for 64 µs. The signals from simultaneously addressed pads were averaged. This data is shown in FIG. 29. Problems with the purification of Oligo O39 in this experiment and the gradual degradation of the active ester in the permeation layer made this data point incomparable with the other data, so it was omitted from the graph. However, O39 still demonstrated binding comparable to the single hydrazide-modified oligos at its unknown effective concentration.

The resulting data demonstrate that all hydrazide modifications have superior performance over amino modified oligonucleotides in terms of immobilization on active ester surfaces. Thus, even single-hydrazide oligos demonstrate improved performance over the currently widely-used amino modified oligos.

Furthermore, oligo 37, which has been made with the novel amidite compound 9, which allows the introduction of four hydrazide groups in one synthesis step, shows similar behavior to oligo 35 in terms of immobilization.

The foregoing is intended to be illustrative of the embodiments of the present invention, and are not intended to limit the invention in any way. Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included herein. All publications and patent applications are herein incorporated by reference to the same extent as if each individual publication or patent application was specifically and individually indicated to be incorporated by reference.

We claim:

1. A compound of the general formula:

$P_r$—O-$L_a$-Bz-(CONHNH-$P_{Ga}$)$_m$ wherein:

Bz is a benzene ring, $L_a$ is a branched or unbranched hydrocarbon of 1 to 12 carbons, arid $L_a$ may optionally include 1 to 4 ether or amide linkages between the carbons;

$P_r$ is a phosphorous bearing reactive group selected from the group consisting of

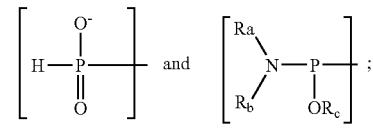

$R_a$ and $R_b$ are branched or unbranched hydrocarbons with 1 to 12 carbons;

$R_c$ is selected from the group consisting of 2-cyanoethyl, allyl, methyl, ethyl, and other alkyl moieties;

each $P_{Ga}$ is, independently, any suitable hydrazide protecting group; and m is 1, 2, or 3.

2. The compound of claim 1 wherein each $P_{Ga}$ is, independently, selected from the group consisting of trityl, methyltrityl, monomethoxytrityl, and dimethoxytrityl.

3. The compound of claim 1 wherein $L_a$ is $(CH_2)_n$, wherein n is an integer between 1 and 12.

4. The compound of claim 1, wherein $R_a$ and $R_b$ are isopropyl and $R_c$ is 2-cyanoethyl.

5. The compound of claim 1 with the general formula:

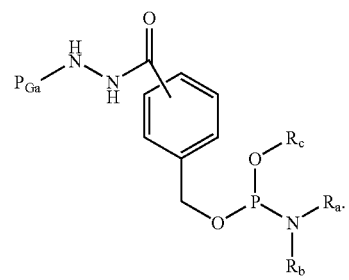

6. The compound of claim 1 with the general formula:

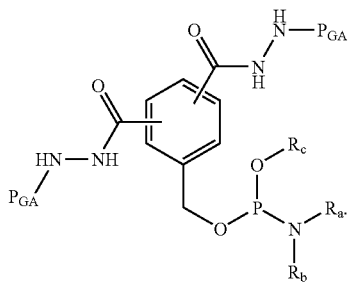

7. The compound of claim 1, wherein $P_r$—O-$L_a$-Bz-(CONHNH-$P_{Ga}$)$_m$ is selected from the group consisting of 5-[(2-Cyanoethyl)(diisopropylamino)phosphanyloxymethyl]-isophthalic acid bis(N'-monomethoxytritylhydrazide), 5-[(2-Cyanoethyl)(diisopropylamino)phosphanyloxymethyl]-isophthalic acid bis(N'-tritylhydrazide), and 4-[(2-Cyanoethyl)(diisopropylamino)phosphanyloxymethyl]-benzoic acid N'-monomethoxytritylhydrazide.

8. The compound of claim 1 wherein each $P_{Ga}$ is mnomethoxytrityl.

9. The compound of claim 1 wherein m is 1.

10. The compound of claim 1 wherein m is 2.

11. The compound of claim 1 wherein $P_r$ is

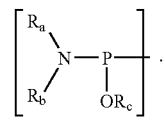

12. The compound of claim 1 wherein $R_a$ and $R_b$ are independently selected from the group consisting of methyl, ethyl, propyl, isopropyl, butyl, isobutyl, and t-butyl.

13. The compound of claim 1 wherein $R_c$ is 2-cyanoethyl.

* * * * *